(12) United States Patent
Liu et al.

(10) Patent No.: US 8,536,128 B2
(45) Date of Patent: *Sep. 17, 2013

(54) GRANULIN/EPITHELIN PRECURSOR (GEP), A CHONDROGENIC GROWTH FACTOR AND TARGET IN CARTILAGE DISORDERS

(75) Inventors: Chuanju Liu, Orange, CT (US); Sally Frenkel, Flushing, NY (US)

(73) Assignee: New York University, New York, NY (US)

( * ) Notice: Subject to any disclaimer, the term of this patent is extended or adjusted under 35 U.S.C. 154(b) by 62 days.

This patent is subject to a terminal disclaimer.

(21) Appl. No.: 12/932,876

(22) Filed: Mar. 8, 2011

(65) Prior Publication Data

US 2012/0230942 A1    Sep. 13, 2012

Related U.S. Application Data

(62) Division of application No. 12/012,521, filed on Jan. 31, 2008, now Pat. No. 7,928,068.

(60) Provisional application No. 60/898,544, filed on Jan. 31, 2007.

(51) Int. Cl.
| | | |
|---|---|---|
| *A61K 38/16* | (2006.01) | |
| *A61K 38/17* | (2006.01) | |
| *A61K 38/18* | (2006.01) | |
| *A61K 38/19* | (2006.01) | |
| *A61K 38/20* | (2006.01) | |

(52) U.S. Cl.
USPC ......... 514/16.7; 514/17.1; 514/21.2; 514/8.8; 514/8.9; 514/9.1; 424/85.2; 424/93.1; 424/93.7

(58) Field of Classification Search
None
See application file for complete search history.

(56) References Cited

U.S. PATENT DOCUMENTS 7,427,595 B1 *   9/2008   Zhu et al. ................... 514/1.1
7,928,068 B2 *   4/2011   Liu et al. .................. 514/17.1

FOREIGN PATENT DOCUMENTS

| WO | WO 03/016475 A2 * | 2/2003 |
| WO | WO2004/045547 | 6/2004 |
| WO | WO2005/000207 | 1/2005 |
| WO | WO2005/106019 | 11/2005 |
| WO | WO2006/044566 | 4/2006 |

OTHER PUBLICATIONS

Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Tokuriki et al., 2009, Curr. Opin. Struc. Biol. 19:596-604.*
Anakwe, O.O. et al, (1990), Acrosome biogeneiss begins during meiosis: evidence from the synthesis and distribution of an acrosomal glycoprotein, acrogranin, during guinea pig spermatogenesis, Biol Reprod, 42(2):317-328.

Baba, T. et al. (1993), Acrogranin, an acrosomal cyseine-rich glycoprotein, is the precursor of the growth-modulating peptides, granulins, and epithelins, and is expressed in somatic as well as male germ cells, Mol Reprod Dev, 34)3):233-243.
Bateman, A. et al. (1990) Granulins, a novel class of peptide from leukocytes, Biochem Biophys Res Commun, 173(3):1161-1168.
Chen, F.H. et al (2005) J Biol Chem 280(38):32655-32661.
Daniel, R. et al. (2000), Cellular localization of gene expression for progranulin, J. Histochem Cytochem, 48(7):999-1009.
Davidson, B. et al., (2004), Granulin-epithelin precursor is a novel prognostic markers in epithelial ovarian carcinoma, Cancer, 100(10):2139-2147.
DiCesare, P. et al (1994b), Cartilage oligomeric matrix protein (COMP) is an abundant component of tendon. FEBS Lett 354(2):237-240.
DiCesare, P. et al (1996), Increased degradation and altered tissue distribution of cartilage oligomeric matrix protein in human rheumatoid and osteoarthritic cartilage, J Ortho Res 14:946-955.
DiCesare, P. et al (1997), Expression of cartilage oligomeric matrix protein by human synovium, FEBS Lett 412(1):249-252.
DiCesare, P. et al (2000), Expression of cartilage oligomeric matrix protein (COMP) by embryonic and adult osteoblasts, J Orthop Res 18(5):713-720.
Feng, J.Q. et al (2010), Granulin epithelin precursor: a bone morphogenic protein 2-inducible growth factor that activates Erk ½ signaling and JunB transcription factor in chondrogenesis, FASEB Journal, 24:1879-1892.
Gonzalez, E.M. et al (2003), A novel interaction between perlecan protein core and progranulin: potential effects on tumor growth, J Biol Chem, 278(40):38113-38116.
He, Z. et al (2003), Progranulin (granulin-epithelin precursor, PC-cell-derived growth factor, acrogranin) mediates tissue repair and tumorigenesis, J. Mol Med, 81(10):600-612.
He, Z. et al (2003), Progranulin is a mediator of the wound response, Nat Med, 9(2):225-229.
Hedbom, E. et al (1992), Cartilage matrix proteins. An acidic oligomeric protein (COMP) detected only in cartilage, J Biol Chem 267(9):6132-6136.

(Continued)

*Primary Examiner* — Elizabeth C Kemmerer

(74) *Attorney, Agent, or Firm* — Foley & Lardner LLP

(57) ABSTRACT

The present invention relates to the expression and regulating growth factors in chondrocytes and developing cartilage, particularly granulin-epithelin precursor (GEP). The invention relates to the modulation and manipulation of these growth factors, GEP, and/or the molecules they interact with, for instance COMP, in cartilage disorders, including arthritis. Assays and screening methods for the determination of the expression and activity of GEP, or of GEP-COMP, are provided, including for screening for the presence or extent of cartilage or arthritic disease and for identifying modulators or compounds/agents for treatment or prevention of cartilage or arthritic diseases.

4 Claims, 31 Drawing Sheets

(56) References Cited

OTHER PUBLICATIONS

Hogue, M. et al. (2003), The growth factor granulin interacts with with cyclin T1 and modulates P-TEFb-dependent transcription, Mol Cell Biol 23(5):1688-1702.

Hogue, M. et al. (2005), Granulin and granulin repeats interact with the Tat.P-TEFb complex and inhibit Tat transactivation, J Biol Chem, 280(14):13648-13657.

Hrabal, R. et al. (1996), The hairpin stack fold, a novel protein architecture for a new family of protein growth factors, Nat Struct Biol, 3(9):747-752.

Jones, M.B. et al, (2003), The granulin-epithelin precursor: a putative new growth factor for ovarian cancer, Gynecol Oncol, 88(1 Pt 2):S136-139.

Justen, H.P. et al (2000), Differential gene expression in synovium of rheumatoid arthritis and osteoarthritis, Mol Cell Biol Res Commun; 3(3):165-172.

Kipnes, J. et al (2003), Effect of cartilage oligomeric matrix protein on mesenchymal chondrogenesis in vitro. Osteoarthritis Cartilage, 11(6):442-454.

Koelling, S. et al. (2006), Cartilage oligomeric matrix protein is involved in human limb development and in the pathogenesis of osteoarthritis, Arthritis Res Ther 8(3): R56.

Kuhne, S.A. et al (1998), Persistent high serum levels of cartilage oligomeric matrix protein in a subgroup of patents with traumatic knee injury, Rheumatol Int. 18:21-25.

Lu, R. et al (2000), Inhibition of PC cell—derived growth factor (PCDGF, epithelin/granulin precursor) expression by antisense PCDGF cDNA transfection inhibits tumorigenicity of the human breast carcinoma cell line MDA-MB-468, Proc Natl Acad, 97(8):3993-3998.

Morgelin, M. et al (1992), Proteoglycans from the swarm rat chondrosarcoma. Structure of the aggregates extracted with associative and dissociative solvents as revealed by electron microscopy, J Biol Chem, 267(20):14275-14284.

Neidhart, M. et al (1997), Small fragments of cartilage oligomeric matrix protein in synovial fluid and serum as markers for cartilage degradation, Br J Rheumatol 36(11):1151-1160.

Saxne, T. et al (1992), Cartilage oligomeric matrix protein: a novel marker of cartilage turnover detectable in synovial fluid and blood, Br J Rheumatol 31(9):583-591.

Shoyab, M. et al (1990), Epithelins 1 and 2: isolation and characterization of two cysteine-rich growth-modulating proteins, Proc Natl Acad Sci U.S.A. 87(20):7912-7916.

Thornburg, N. et al (2004), Identification of Epstein-Barr virus RK-BARK0-interacting proteins and characterization of expression pattern, J Virol 78(23):12848-12856.

Wang, W. et al, (2003), PC cell-derived growth factor (granulin precursor) expression and action in human multiple myeloma, Clin Cancer Res, 9(6):2221-2228.

Wright, W.E. et al (1989), Myogenin, a factor regulating myogenesis, has a domain homologous to MyoD, Cell, 56(4):607-617.

Xia, X et al (1998), Identification of cell surface binding sites for PC-cell-derived growth factor, PCDGF, (epithelin/granulin precursor) on epithelial cells and fibroblasts, Biochem Biophys Res Commun, 245(2):539-543.

Xu, S.Q. et al. (1998), The granulin/epithelin precursor abrogates the requirement for the insulin-like growth factor 1 receptor for growth in vitro, J Biol Chem, 273(32):20078-20083.

Zanocco-Marani, T. et al. (1999), Biological activities and signaling pathways of the granulin/epithelin precursor, Cancer Res., 59(20):5331-5340.

Zhang, H. et al. (1998), Inhibition tumorigenicity of the PC cell line by transfection with antisense cDNA for PC cell-derived growth factor (PCDGF, epithelin/granulin precursor), Proc Natl Acad Sci U.S.A., 95(24):14202-14207.

Zhou, J. et al, (1993), Purification of an autocrine growth factor homologous with mouse epithelin precursor from a highly tumorigenic cell line, J. Bio. Chem., 268(15):10863-10869.

Zhu, J. et al, (2002), Conversion of proepithelin to epithelins: roles of SLPI and elastase in host defense and wound repair, Cell, 111(6):867-878.

Hunziker, EB, "Growth-factor-induced healing of partial-thickness defects in adult articular cartilage," Osteoarthritis Cartilage, 9(1), (Jan. 2001), pp. 22-32.

Indrawattana, N. et al., "Growth factor combination for chondrogenic induction from human mesenchymal stem cell," Biochem Biophys Res Commun, 320(3), (2004), pp. 914-919.

Joyce, Michael E. et al., "Transforming Growth Factor-β and the Initiation of Chondrogenesis and Osteogenesis in the Rat Femur," The Journal of Cell Biology, vol. 110, (Jun. 1990), pp. 2195-2207.

Kato, Yukio et al., "Sulfated Proteoglycan Synthesis by Confluent Cultures of Rabbit Costal Chondrocytes Grown in the Presence of Fibroblast Growth Factor," The Journal of Cell Biology, vol. 100, (Feb. 1985), pp. 477-485.

Olney, R.C. et al., "Growth factor regulation of human growth plate chondrocyte proliferation in vitro," Biochem Biophys Res Commun, 317(4), (2004), pp. 1171-1182.

Ornitz, D.M. et al., "FGF signaling pathways in endochondral and intramembranous bone development and human genetic disease," Genes Dev, 16(12), (2002), pp. 1446-1465.

Osborn, KD et al., "Growth factor stimulation of adult articular cartilage," J Orthop Res, 7, (1989), pp. 35-42.

Pei, M. et al., "Growth factors for sequential cellular de- and re-differentiation in tissue engineering," Biochem Biophys Res Commun, 294(1), (2002), pp. 149-154.

Sumner, DR et al., "Enhancement of bone ingrowth by transforming growth factor-beta," J Bone Joint Surg Am, 77, (1995), pp. 1135-1147.

Veilleux, N. et al., "Effects of FGF-2 and IGF-1 on adult canine articular chondrocytes in type II collagen-glycosaminoglycan scaffolds in vitro," Osteoarthritis Cartilage, 13(4), (2005), pp. 278-286.

* cited by examiner

FIGURE 20

```
-1807   ggcacagact agtactaggt cctcagcagg ccaggtgtct tatccgctgt
-1757   ctgggtctgc tctagctcca ggcttagaac ccctgccaca cgactccaca  Smad3
-1707   gctcggttgg cacccttttcc ctcctccgac ttctgctgcc tcgagcttgg
-1657   ttagccatcc cctgcccct gcctcatcct cagctccagt tccttgctca
-1607   ggctgcagca gtctccatcc cctgtgcaga cactgccgtt cctccacggc
-1557   ccagtatcag gctttccctg ggcctctcct ctctcctggc ccatctccca
-1507   tcatccatct ctgcctggcc caggcccttt ggcaccaagc aggctgactc
-1457   ttgtcactgg ctaatctgtt ctgtggtaca ttttctctcc tcaccctccc
-1407   atatcaattc ctcgaaggca gggccgatct ggagactagg aagccacttc
-1357   tctttcgaca gcccccacca cagcccagcc cgtgccaggc acccagcagc  AML1/CBFA2
-1307   tcctgaagcc cactggcatt gaacatggca ttcaatccct gccaagcctg
-1257   cccttcccat ctggtttccc agggctcttc ccaacacctc ctcctccacc
-1207   tgccagttaa aatcttccca gactcagctc aaggagatgc tcctaaggtg
-1157   gaatgaaatc tcttcttccc cacctggaga caatctactt cctctcccta
-1107   cacctggcaa ctggcgcaca accttgtatc ttaaattaga ttcagcctga
-1057   gactgtctcc caccaatccc tgctccctgt cctgctgagc accttgagga
-1007   aagggctttg gggctgttta tctttgtcct ggaaaccatc cttcaactca
-957    ctctggggcc tgcctagcat gtcaaccgag tttggagaat agggcagaat
-907    agggcaggac aggacaggac aagacagggc aggataggat aggagcgagc  Smad4
-857    cagctcagta gctcacattt gtaatcccag cgccttgggg ggctgcggta
-807    ggagaatcgc tttgggagca ggagttgcag gccgcagtga gctatgatca
-757    gcttgggcga ctgagcgaga ccctgtctct aaaacaaaca cacaagtccg
-707    ggcgcggtgg ctcatgcctg taatcttagc actttgggag gccgaggtgg
-657    gcggatcacg aggtcaagaa atcgagacca tcctggccaa catggtgaaa
-607    ccccgtctct actaaaaata caaaaattag ctgggcgtgg tggtgcgcgc  E2F
-557    ctgtagtccc agctactcgg gaggctgagg caggagaatc gcttgaaccc
-507    gggaggcaga ggttgcagtg agccgagatc gtgccactgc actccagcct
-457    ggcgacagag tgagactccg tctcagaaca aacaaacaaa aggatagaaa
-407    ggcgagcaca aatattccca attcataaca ctccctcgca ctgtcaatgc
-357    cccagacacg cgctatcatc tctagcaaac tcccccaggc gcctgcagga  NF-κB
-307    tgggttaagg aaggcgacga gcaccagctg ccctgctggg gctgtcccga
-257    cgtcacatga ttctccaatc acatgatccc tagaaatggg gtgtggggcg
-207    agaggaagca gggaggagag tgatttgagt agaaaagaaa cacagcattc
-157    caggctggcc ccacctctat attgataagt agccaatggg agcgggtagc
-107    cctgatccct ggccaatgga aactgaggta ggcgggtcat cgcgctgggg
-57     tctgtagtct gagcgctacc cggttgctgc tgcccaagga ccgcggagtc
-7      ggacgcaggt aggagagcgg ccgcgcagac ctctcgcctg ctcctgccca
        e1  i1
43      ggggccgcc agggccatgt gagcttgagg ttcccctgga gtctcagccg
93      gagacaacag aagaaccgct tactgaaact ccttgggggt tctgatacac
```

FIGURE 21
A.
B.
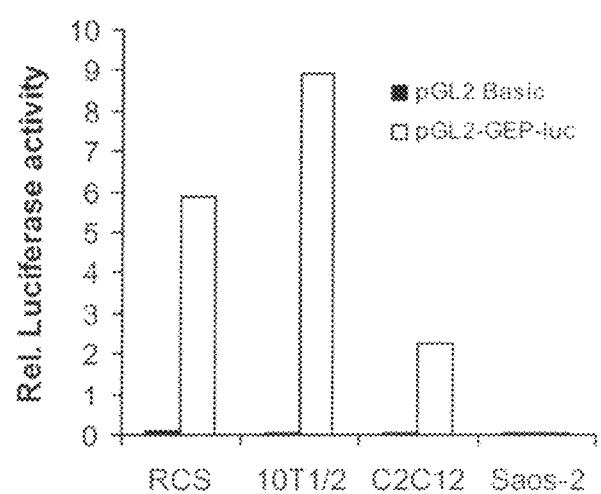

FIGURE 23
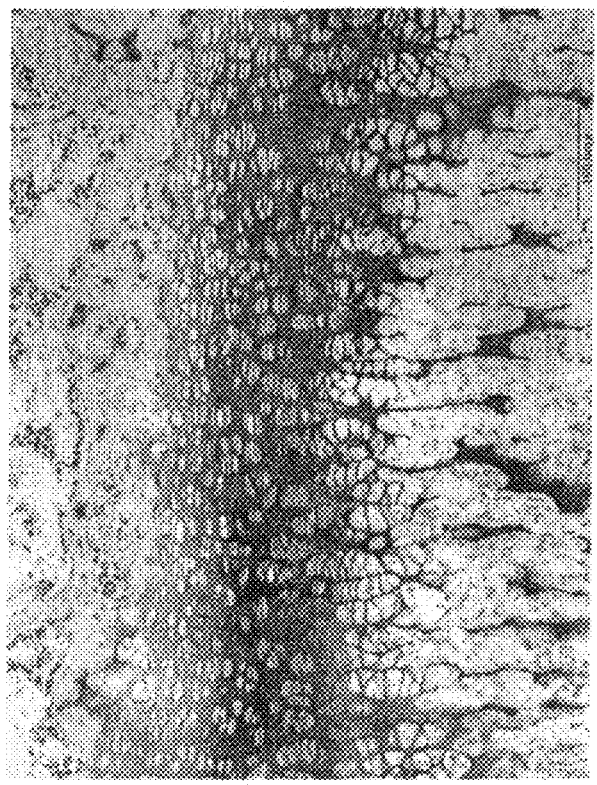
KD
WT

FIGURE 25
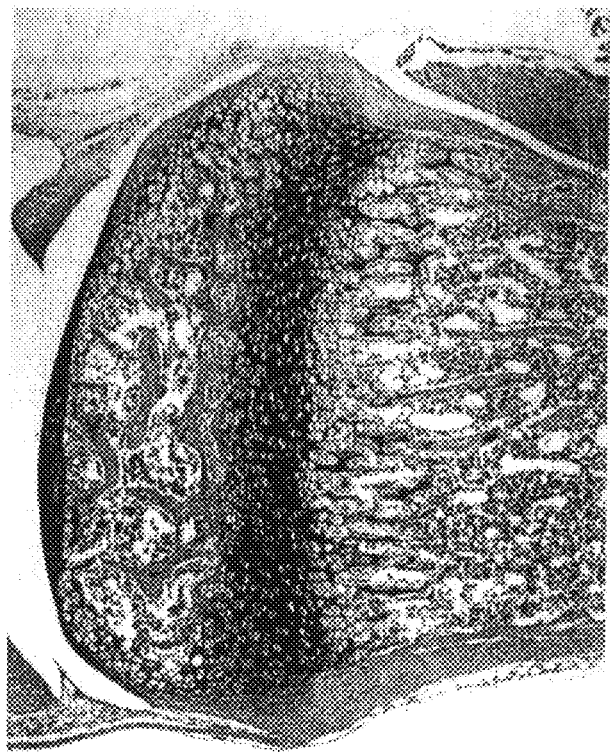
KD
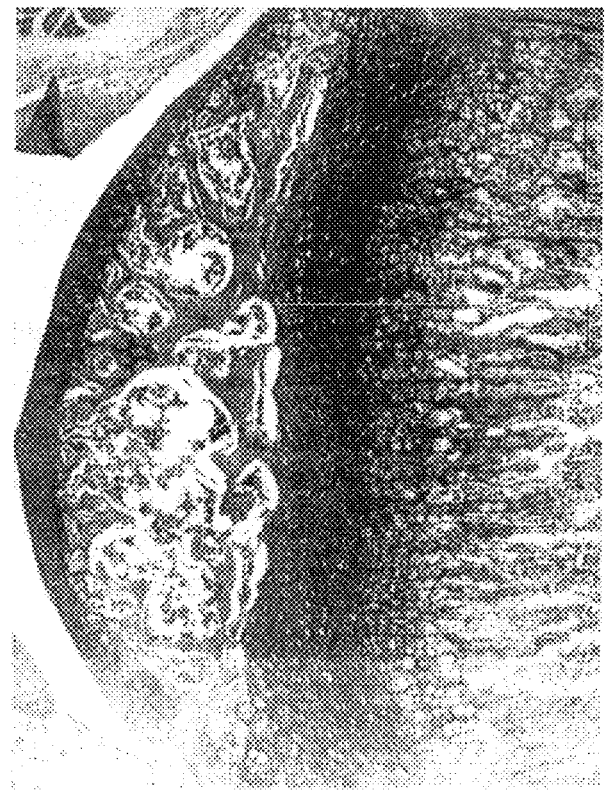
WT

GRANULIN/EPITHELIN PRECURSOR (GEP), A CHONDROGENIC GROWTH FACTOR AND TARGET IN CARTILAGE DISORDERS

CROSS REFERENCE TO RELATED APPLICATIONS

This application is a divisional of copending U.S. application Ser. No. 12/012,521, filed Jan. 31, 2008, now U.S. Pat. No. 7,928,068, of which the instant application claims the benefit of the filing date pursuant to 35 U.S.C. § 120, and which claims priority to U.S. Provisional Patent Application 60/898,544, filed Jan. 31, 2007 and the benefit of the filing date pursuant to 35 U.S.C. § 119. All of the above-identified applications are incorporated herein by reference in their entirety.

GOVERNMENTAL SUPPORT

The research leading to the present invention was supported, at least in part, by a grant from the NIH, research Grant Nos. AR052022 and AR050620. Accordingly, the Government may have certain rights in the invention.

FIELD OF THE INVENTION

The present invention relates generally to the expression and regulation of growth factors in chondrocytes and developing cartilage. The invention relates to the modulation and manipulation of these growth factors and/or the molecules they interact with in cartilage disorders, including arthritis.

BACKGROUND OF THE INVENTION

Chondrogenesis is the earliest well-orchestrated and controlled phase of skeletal development, involving mesenchymal cell recruitment and migration, condensation of progenitors, chondrocyte proliferation and differentiation, and maturation. This process is controlled exquisitely by cellular interactions with the growth factors, surrounding matrix proteins and other environmental factors that mediate cellular signaling pathways and transcription of specific genes in a temporal-spatial manner [1-3]. Production of and response to different growth factors are observed at all times and autocrine and paracrine cell stimulations are key elements of the process [4, 5]. Particularly relevant is the role of the TGF-beta superfamily, and more specifically of the BMP subfamily. Other factors include retinoids, FGFs, GH, and IGFs [6-8]. The growing evidences demonstrated that complicated cellular signaling language and informational content of chondrogenesis lie, not in an individual growth factor, but in the entire set of growth factors and others signals to which a cell is exposed[4, 5, 9]. The ways in which growth factors exert their combinatorial effects are becoming clearer as the molecular mechanisms of growth factors actions are being investigated. Gene- and cell-based therapy of growth factors for cartilage disorders are under intensive study. The isolation of the growth factor(s) that regulating chondrogenesis is therefore of great importance from both a pathophysiological and a therapeutic standpoint.

Granulin/epithelin precursor (GEP), a previously unrecognized growth factor in cartilage, was identified, for the first time, to be a novel chondrogenic factor based on the following findings: GEP is highly expressed in the chondrocytes in various differential stages of growth plate; GEP co-localizes with COMP, a major component of cartilage, in the primary adult chondrocyte and these two proteins bind to each other; GEP, whose level is strongly upregulated by both chondrogenic growth factors (BMP-2 and TGF-beta) and proinflammatory cytokines TNF-alpha, promoted proliferation and chondrocyte differentiation from stem cells; and GEP affects chondrocyte functions.

In the progression of arthritis, synovium, cartilage and bone are each sites of increased growth factor, cytokine, and inflammatory mediator production that are believed to contribute to disease pathogenesis[10, 11]. Although both bone and synovium have important roles in the pathogenesis of arthritis[10, 12], most effort in disease modifying treatments has focused on molecular events within articular cartilage. Arthritic chondrocytes undergo a series of complex changes, including hypertrophy, proliferation, catabolic alteration and, ultimately, death. The regulation of these phenotypic changes at different stages of disease is also under intensive study, with focus on the biomechanical and biochemical signals that regulate each of these discrete chondrocyte responses[11, 13]. Chondrocytes themselves are featured protagonists in this cascade of change, not only the target of external biomechanical and biochemical stimuli, but also themselves the cellular source of cytokines, chemokines, proteases and inflammatory mediators that promote the deterioration of articular cartilage[10, 11]. Pathogenic molecules produced by arthritic chondrocytes include matrix metalloproteinases (MMPs), ADAMTSs, interleukin (IL)-1, tumor necrosis factor (TNF), IL-6, IL-8, nitric oxide, prostaglandins and leukotrienes [11, 13]. There is also evidence that arthritic chondrocytes exhibit increased anabolic activity, including increased release of growth factors and synthesis of type II collagen, proteoglycan, extracellular matrix protein 1 (ECM1, our unpublished data) and other extracellular matrix proteins, as well as the expression of genes associated with the chondroprogenitor hypertrophic phenotype[14-16].

GEP, also known as PC-cell-derived growth factor (PCDGF), progranulin (pgrn), proepithelin, acrogranin, GP80, was first purified as a growth factor from conditioned tissue culture media [17, 18]. It has been identified from different sources by several independent laboratories [19-22]. GEP is a 593-amino-acid secreted glycoprotein with an apparent molecular weight of 80 kDa [19, 23], which acts as an autocrine growth factor. GEP contains seven and a half repeats of a cysteine-rich motif ($CX_{5-6}CX_5CCX_8CCX_6CCXDX_2HCCPX_4CX_{5-6}C$) in the order P-G-F-B-A-C-D-E, where A-G are full repeats and P is the half motif (FIG. 1). The C-terminal region of the consensus sequence contains the conserved sequence $CCXDX_2HCCP$ and is suggested to have a metal binding site and to be involved in regulatory function [24]. Notably, GEP undergoes proteolytic processing with the liberation of small, ~6 kDa repeat units known as granulins (or epithelins), which retain biological activity [25]: peptides are active in cell growth assays [22] and may be proinflammatory [26].

GEP is abundantly expressed in rapidly cycling epithelial cells, in cells of the immune system and in neurons [19-21, 26]. High levels of GEP expression are also found in several human cancers, and contributes to tumorigenesis in diverse cancers, including breast cancer, clear cell renal carcinoma, invasive ovarian carcinoma, glioblastoma, adipocytic teratoma, multiple myeloma [25, 27-33] and osteosarcoma (our unpublished data). Although GEP mainly functions as a secreted growth factor, it was also found to be localized inside the cells and directly modulate intracellular activities [21, 34-36]. The role of GEP in the regulation of cellular proliferation has been well characterized using mouse embryo fibroblasts derived from mice with a targeted deletion of the insulin-like growth factor receptor (IGF-IR) gene ($R^-$ cells).

These cells are unable to proliferate in response to IGF-I and other growth factors (EGF and PDGF) necessary to fully progress through the cell cycle [37]. In contrast, GEP is the only known growth factor able to bypass the requirement for the IGF-IR, thus promoting growth of R−cells [22, 38]. Increasing evidences have also implicated GEP in the regulation of differentiation, development and pathological processes. It has been isolated as a differentially-expressed gene from mesothelial differentiation [39], sexual differentiation of the brain [40], macrophage development [41] and synovium of rheumatoid arthritis and osteoarthritis [42]. Remarkably, GEP was also shown to be a crucial mediator of wound response and tissue repair [30, 43]. Very recently, it was reported that mutations in GEP cause tau-negative frontotemporal dementia linked to chromosome 17 [44-47].

The mode of action of GEP remain largely unknown. Granulin binding sites have been demonstrated, although cell surface receptors have not yet been characterized [28, 48]. GEP leads to activation of the mitogen-activated protein kinase pathway and to stimulation of cyclin D1 protein expression. This can account for the cellular proliferation activity of granulin and its ability to replace estrogen in inducing the growth of breast cancer cells [49]. Several GEP-associated partners have been reported and found to affect GEP action in various processes. One example of this is the secretory leukocyte protease inibitor (SLPI). Elastase digests GEP exclusively in the interepithelin linkers resulting in the generation of granulin peptides, suggesting that this protease may be an important component of a GEP convertase. SLPI blocks this proteolysis either by directly binding to elastase or by sequestering epithelin peptides from the enzyme [43]. It was found that GEP can modulate transcription activities by interacting with human cyclin T1, a component of positive transcription elongation factor b (P-TEFb) [35] and Tat-P-TEFb [34]. GEP was also found to interact with perlecan, a heparan sulfate proteoglycan and perlecan-null mice exhibit the severe skeletal defects [50-52]. The perlecan-GEP interaction was suggested to modulate tumor growth [28]. Our global screen led to the isolation of GEP as a novel binding growth factor of COMP, a noncollagenous component of the cartilage matrix. The interaction between these two molecules appears to regulate chondrocyte proliferation.

Modern methods of global analysis of protein-protein interactions followed by biological assessment have led to new ways to identify novel proteins not previously associated with the pathogenesis of a particular disease or organ system. Initially identified through a functional genetic screen, this application details the discovery that GEP, previously unknown as a growth factor in cartilage, is a novel mediator in chondrogenesis and arthritis. This extends our understanding of the actions of growth factors in cartilage biology and their application to treatment of cartilage disorders and arthritic conditions. The identification and manipulation of growth factors that regulate the chondrogenic potential of mesenchymal stem cells (MSCs), chondrocyte progenitors and chondrocytes can be used to optimize the therapeutic application of growth factors and these cells in cartilage disorders and connective tissue disorders.

1. Colnot, C., *Cellular and molecular interactions regulating skeletogenesis*. J Cell Biochem, 2005. 95(4): p. 688-97.
2. Franz-Odendaal, T. A. and M. K. Vickaryous, *Skeletal elements in the vertebrate eye and adnexa: morphological and developmental perspectives*. Dev Dyn, 2006. 235(5): p. 1244-55.
3. Goldring, M. B., K. Tsuchimochi, and K. Ijiri, *The control of chondrogenesis*. J Cell Biochem, 2006. 97(1): p. 33-44.
4. Ornitz, D. M. and P. J. Marie, *FGF signaling pathways in endochondral and intramembranous bone development and human genetic disease*. Genes Dev, 2002. 16(12): p. 1446-65.
5. Tuan, R. S., *Cellular signaling in developmental chondrogenesis: N-cadherin, Wnts, and BMP-2*. J Bone Joint Surg Am, 2003. 85-A Suppl 2: p. 137-41.
6. Pei, M., et al., *Growth factors for sequential cellular de- and re-differentiation in tissue engineering*. Biochem Biophys Res Commun, 2002. 294(1): p. 149-54.
7. Veilleux, N. and M. Spector, *Effects of FGF-2 and IGF-1 on adult canine articular chondrocytes in type II collagen-glycosaminoglycan scaffolds in vitro*. Osteoarthritis Cartilage, 2005. 13(4): p. 278-86.
8. Olney, R. C., et al., *Growth factor regulation of human growth plate chondrocyte proliferation in vitro*. Biochem Biophys Res Commun, 2004. 317(4): p. 1171-82.
9. Indrawattana, N., et al., *Growth factor combination for chondrogenic induction from human mesenchymal stem cell*. Biochem Biophys Res Commun, 2004. 320(3): p. 914-9.
10. Martel-Pelletier, J., *Pathophysiology of osteoarthritis*. Osteoarthritis Cartilage, 1999. 7(4): p. 371-3.
11. Petersson, I. F., et al., *Changes in cartilage and bone metabolism identified by serum markers in early osteoarthritis of the knee joint*. Br J Rheumatol, 1998. 37(1): p. 46-50.
12. Ayral, X., *Diagnostic and quantitative arthroscopy: quantitative arthroscopy*. Baillieres Clin Rheumatol, 1996. 10(3): p. 477-94.
13. Ayral, X., et al., *Effects of video information on preoperative anxiety level and tolerability of joint lavage in knee osteoarthritis*. Arthritis Rheum, 2002. 47(4): p. 380-2.
14. Aigner, T., et al., *Reexpression of type IIA procollagen by adult articular chondrocytes in osteoarthritic cartilage*. Arthritis Rheum, 1999. 42(7): p. 1443-50.
15. Lippiello, L., D. Hall, and H. J. Mankin, *Collagen synthesis in normal and osteoarthritic human cartilage*. J Clin Invest, 1977. 59(4): p. 593-600.
16. Sandell, L. J. and T. Aigner, *Articular cartilage and changes in arthritis. An introduction: cell biology of osteoarthritis*. Arthritis Res, 2001. 3(2): p. 107-13.
17. Wright, W. E., D. A. Sassoon, and V. K. Lin, *Myogenin, a factor regulating myogenesis, has a domain homologous to MyoD*. Cell, 1989. 56(4): p. 607-17.
18. Zhou, J., et al., *Purification of an autocrine growth factor homologous with mouse epithelin precursor from a highly tumorigenic cell line*. J Biol Chem, 1993. 268(15): p. 10863-9.
19. Anakwe, O. O. and G. L. Gerton, *Acrosome biogenesis begins during meiosis: evidence from the synthesis and distribution of an acrosomal glycoprotein, acrogranin, during guinea pig spermatogenesis*. Biol Reprod, 1990. 42(2): p. 317-28.
20. Baba, T., et al., *Acrogranin, an acrosomal cysteine-rich glycoprotein, is the precursor of the growth-modulating peptides, granulins, and epithelins, and is expressed in somatic as well as male germ cells*. Mol Reprod Dev, 1993. 34(3): p. 233-43.
21. Daniel, R., et al., *Cellular localization of gene expression for progranulin*. J Histochem Cytochem, 2000. 48(7): p. 999-1009.
22. Zanocco-Marani, T., et al., *Biological activities and signaling pathways of the granulin/epithelin precursor*. Cancer Res, 1999. 59(20): p. 5331-40.
23. Ong, C. H. and A. Bateman, *Progranulin (granulin-epithelin precursor, PC-cell derived growth factor, acrogra-*

24. Hrabal, R., et al., *The hairpin stack fold, a novel protein architecture for a new family of protein growth factors.* Nat Struct Biol, 1996. 3(9): p. 747-52.
25. Davidson, B., et al., *Granulin-epithelin precursor is a novel prognostic marker in epithelial ovarian carcinoma.* Cancer, 2004. 100(10): p. 2139-47.
26. Lu, R. and G. Serrero, *Inhibition of PC cell-derived growth factor (PCDGF, epithelin/granulin precursor) expression by antisense PCDGF cDNA transfection inhibits tumorigenicity of the human breast carcinoma cell line MDA-MB-468.* Proc Natl Acad Sci USA, 2000. 97(8): p. 3993-8.
27. Bateman, A., et al., *Granulins, a novel class of peptide from leukocytes.* Biochem Biophys Res Commun, 1990. 173(3): p. 1161-8.
28. Gonzalez, E. M., et al., *A novel interaction between perlecan protein core and progranulin: potential effects on tumor growth.* J Biol Chem, 2003. 278(40): p. 38113-6.
29. He, Z. and A. Bateman, *Progranulin (granulin-epithelin precursor, PC-cell-derived growth factor, acrogranin) mediates tissue repair and tumorigenesis.* J Mol Med, 2003. 81(10): p. 600-12.
30. He, Z., et al., *Progranulin is a mediator of the wound response.* Nat Med, 2003. 9(2): p. 225-9.
31. Jones, M. B., M. Spooner, and E. C. Kohn, *The granulin-epithelin precursor: a putative new growth factor for ovarian cancer.* Gynecol Oncol, 2003. 88(1 Pt 2): p. S136-9.
32. Wang, W., et al., *PC cell-derived growth factor (granulin precursor) expression and action in human multiple myeloma.* Clin Cancer Res, 2003. 9(6): p. 2221-8.
33. Zhang, H. and G. Serrero, *Inhibition of tumorigenicity of the teratoma PC cell line by transfection with antisense cDNA for PC cell-derived growth factor (PCDGF, epithelin/granulin precursor).* Proc Natl Acad Sci USA, 1998. 95(24): p. 14202-7.
34. Hoque, M., et al., *Granulin and granulin repeats interact with the Tat.P-TEFb complex and inhibit Tat transactivation.* J Biol Chem, 2005. 280(14): p. 13648-57.
35. Hoque, M., et al., *The growth factor granulin interacts with cyclin T1 and modulates P-TEFb-dependent transcription.* Mol Cell Biol, 2003. 23(5): p. 1688-702.
36. Thornburg, N. J., S. Kusano, and N. Raab-Traub, *Identification of Epstein-Barr virus RK-BARF0-interacting proteins and characterization of expression pattern.* J Virol, 2004. 78(23): p. 12848-56.
37. Sell, C., et al., *Effect of a null mutation of the insulin-like growth factor I receptor gene on growth and transformation of mouse embryo fibroblasts.* Mol Cell Biol, 1994. 14(6): p. 3604-12.
38. Xu, S. Q., et al., *The granulin/epithelin precursor abrogates the requirement for the insulin-like growth factor 1 receptor for growth in vitro.* J Biol Chem, 1998. 273(32): p. 20078-83.
39. Sun, X., M. Gulyas, and A. Hjerpe, *Mesothelial differentiation as reflected by differential gene expression.* Am J Respir Cell Mol Biol, 2004. 30(4): p. 510-8.
40. Suzuki, M. and M. Nishiahara, *Granulin precursor gene: a sex steroid-inducible gene involved in sexual differentiation of the rat brain.* Mol Genet Metab, 2002. 75(1): p. 31-7.
41. Barreda, D. R., et al., *Differentially expressed genes that encode potential markers of goldfish macrophage development in vitro.* Dev Comp Immunol, 2004. 28(7-8): p. 727-46.
42. Justen, H. P., et al., *Differential gene expression in synovium of rheumatoid arthritis and osteoarthritis.* Mol Cell Biol Res Commun, 2000. 3(3): p. 165-72.
43. Zhu, J., et al., *Conversion of proepithelin to epithelins: roles of SLPI and elastase in host defense and wound repair.* Cell, 2002. 111(6): p. 867-78.
44. Baker, M., et al., *Mutations in progranulin cause tau-negative frontotemporal dementia linked to chromosome 17.* Nature, 2006. 442(7105): p. 916-9.
45. Cruts, M., et al., *Null mutations in progranulin cause ubiquitin positive frontotemporal dementia linked to chromosome 17q21.* Nature, 2006. 442(7105): p. 920-4.
46. Gass, J., et al., *Mutations in progranulin are a major cause of ubiquitin positive frontotemporal lobar degeneration.* Hum Mol Genet, 2006. 15(20): p. 2988-3001.
47. Rowland, L. P., *Frontotemporal dementia, chromosome 17, and progranulin.* Ann Neurol, 2006. 60(3): p. 275-7.
48. Xia, X. and G. Serrero, *Identification of cell surface binding sites for PC-cell-derived growth factor, PCDGF, (epithelin/granulin precursor) on epithelial cells and fibroblasts.* Biochem Biophys Res Commun, 1998. 245(2): p. 539-43.
49. Lu, R. and G. Serrero, *Mediation of estrogen mitogenic effect in human breast cancer MCF-7 cells by PC-cell-derived growth factor (PCDGF/granulin precursor).* Proc Natl Acad Sci USA, 2001. 98(1): p. 142-7.
50. Arikawa-Hirasawa, E., et al., *Perlecan is essential for cartilage and cephalic development.* Nat Genet, 1999. 23(3): p. 354-8.
51. Kvist, A. J., et al., *Chondroitin sulfate perlecan enhances collagen fibril formation. Implications for perlecan chondrodysplasias.* J Biol Chem, 2006. 281(44): p. 33127-39.
52. Nicole, S., et al., *Perlecan, the major proteoglycan of basement membranes, is altered in patients with Schwartz-Jampel syndrome (chondrodystrophic myotonia).* Nat Genet, 2000. 26(4): p. 480-3.

The citation of references herein shall not be construed as an admission that such is prior art to the present invention.

SUMMARY OF THE INVENTION

Chondrogenesis plays a fundamental role in skeletal patterning, bone formation and joint development. Well-orchestrated chondrogenesis is controlled exquisitely by cellular interactions with extracellular signals, specially the growth factors. Several growth factors such as BMP-2, TGF-beta, and FGF have been found to be pivotal for cartilage development via triggering chondrogenic signaling and gene regulation. Gene- and cell-based therapy of growth factors for cartilage disorders are under intensive study. The isolation of the growth factor(s) that regulate chondrogenesis is therefore of great importance from both a pathophysiological and a therapeutic standpoint. Thus, the purpose of this invention is to utilize the novel growth factor(s) GEP and its binding proteins, including agonists and antagonists, that are relevant for normal cartilage development and progression of cartilage disorders, including arthritis, to further understand the mechanism underlying the control of chondrogenesis by growth factors and cytokines and to provide new molecular targets for prediction, diagnosis and treatment of cartilage-related diseases.

The encoding sequence of at least both human and mouse GEP are known. The mRNA sequence of human and mouse GEP are set out in SEQ ID NOS: 1 and 3 respectively. Human and mouse GEP encoded polypeptides are provided in SEQ ID NOS: 2 and 4 respectively. The rat GEP amino acid sequence is set out in SEQ ID NO: 22. GEP undergoes proteolytic processing to release granulins (or epithelins), n6 kDa repeat units, which retain biological activity. Rat GEP granulin or fragment sequences are provided in SEQ ID NOS: 15-19.

Understanding the molecular mechanism of cartilage development and arthritis progression is the first and fundamental step to detect and treat cartilage disorders, including arthritis. This invention provides us a new chondroinductive growth factor and extends our understanding of the actions of growth factors in cartilage biology. Identification of growth factors that regulate the chondrogenic potential of mensenchymal stem cells (MSC) is crucial to develop and optimize the therapeutic application of growth factors and MSCs in cartilage disorders.

Granulin/epithelin precursor (GEP), a previously unrecognized growth factor of cartilage was identified, for the first time, to be a novel chondrogenic factor based on the following facts: GEP is highly expressed in the chondrocytes in various differential stages of growth plate; GEP co-localizes with COMP, a major component of cartilage, in the primary adult chondrocyte and these two proteins bind to each other; GEP, whose level is strongly upregulated by both chondrogenic growth factors (BMP-2 and TGF-beta) and proinflammatory cytokines TNF-alpha, promoted chondrocyte proliferation.

Applications of this invention include: 1) to directly recruit GEP (recombinant protein and DNA), its processed units, their analogous compounds, or their combinations with other well-characterized chondroinductive factors to devise a novel treatment for cartilage repair; 2) to utilize MSCs, chondrocytes, chondrocyte progenitors or other cells bearing GEP or its analogous compounds for cartilage disorders; 3) to employ GEP or its analogous compounds for treating arthritis; and 4) to inactivate the antagonists of GEP for devising new treatments for cartilage repair and arthritis.

In accordance with the present invention, a method for modulating chondrogenesis is provided comprising modulating the expression or activity of GEP. In a particular such aspect, the differential growth or proliferation of cartilage or chondrocytes is increased by modulation of GEP. The invention provides a method for producing cartilage at a cartilage defect site comprising administering, including at the defect site, GEP, an active fragment thereof, including but not limited to a granulin, such that the production of cartilage is stimulated. The invention provides a method for producing cartilage at a cartilage defect site comprising administering, including at the defect site, a modulator of GEP such that the production of cartilage is stimulated.

The invention provides a method for modulating chondrogenesis comprising modulating the expression or activity of granulin/epithelin precursor (GEP) or an active fragment thereof.

The invention further provides a method for increasing the growth or proliferation of cartilage or chondrocytes in an animal comprising increasing the expression or modulating the activity of GEP or an active fragment thereof.

The invention includes a method for producing cartilage at a cartilage defect site in an animal comprising administering to said animal at the defect site GEP or an active fragment thereof, whereby the production of cartilage is stimulated. In one aspect of such method, said GEP or active fragment is administered in combination with chondrocyte progenitors, mesenchymal stem cells, or stem cells capable of differentiating along the mesenchymal lineage. In a further aspect of this method, GEP or an active fragment thereof is administered in combination with one or more growth factor, particularly a growth factor which stimulates, is stimulated by, or acts in conjunction with or synergistically with GEP. A growth factor may be selected from BMP-2, TGF β, TNF α, SLPI, FGF or IL-1β.

In a further aspect a method is provided for producing cartilage at a cartilage defect site in an animal comprising administering to said animal at the defect site a modulator of GEP selected from an agent, agonist, antagonist, inhibitor or activator, whereby the production of cartilage is stimulated.

In a further aspect, the differentiation of stem cells, particularly mesenchymal stem cells or cells capable of differentiating along the mesenchymal pathway, including for instance differentiating to chondrocytes and chondrocyte progenitors, is enhanced along the mesenchymal or chondrocyte lineage. The invention thus provides a method for stimulating the proliferation or differentiation of chondrocytes in an animal comprising administering to said animal GEP or an active fragment thereof. In a further aspect, the invention provides a method for stimulating the proliferation or differentiation of chondrocytes in vitro or in culture comprising administering to said culture, or under in vitro conditions, GEP or an active fragment thereof. In one such aspect GEP or an active fragment thereof is administered in combination with chondrocyte progenitors, mesenchymal stem cells or stem cells capable of differentiating along the mesenchymal lineage. In a further such embodiment, GEP or an active fragment thereof is administered to chondrocyte progenitors, mesenchymal stem cells or stem cells capable of differentiating along the mesenchymal lineage in vitro or in culture, to stimulate such cells prior to the administration of said stimulated cells to an animal.

The invention thus provides a method for cartilage repair or regeneration in an animal comprising administering to said animal GEP or an active fragment thereof in combination with cells selected from chondrocyte progenitors, mesenchymal stem cells, or stem cells capable of differentiating along the mesenchymal lineage, whereby the cells and GEP or active fragment are administered simultaneously or individually.

In one aspect of this method is provided a method for cartilage repair or regeneration in an animal comprising administering to said animal GEP or an active fragment thereof in combination with cells selected from chondrocyte progenitors, mesenchymal stem cells, or stem cells capable of differentiating along the mesenchymal lineage, whereby the cells are pre-stimulated by incubation with GEP or an active fragment thereof.

Also provided is a method for stimulating the differentiation of mesenchymal stem cells or cells capable of differentiating along the mesenchymal pathway, including differentiation to chondrocytes and chondrocyte progenitors, comprising combining or incubating said cells with GEP or an active fragment thereof.

In any of these above methods, GEP or an active fragment thereof comprises an amino acid sequence selected from SEQ ID NO: 2, 4, 15-19 and 22.

In an aspect of the invention, GEP or active fragments or portions thereof, including but not limited to the granulin(s), can be combined with chondrocyte progenitors, mesenchymal stem cells, or stem cells capable of differentiating along the mesenchymal lineage to provide cell therapy compositions. Such compositions or combinations may be utilized for cartilage repair, regeneration or therapy. In one such aspect, arthritis or cartilage damage is reduced or repaired by administration of GEP, or active fragement(s) thereof, in combination or in series with chondrocyte progenitors or stem cells, or by administration of stem cells pre-stimulated by incubation with GEP or an active fragment or portion thereof.

A method for the modulation or alleviation of arthritis is provided comprising administering GEP or an active fragment or portion thereof. A method for cartilage repair is further provided comprising administering GEP or an active fragment or portion thereof. Any such methods may alternatively or additionally utilize administration of modulators of GEP activity or expression. Such modulators may include agents, agonists, antagonists, inhibitors or activators of GEP.

The therapeutic methods include the treatment of various conditions, particularly various orthopedic and rheumatologic conditions, including degenerative connective tissue disorders or in the event of physical trauma. The methods include administration in instances where cartilage repair and/or regeneration is appropriate, such as to treat cartilage defects, osteoarthritis, collagen disorders, dwarfism, including camptomelic dysplasia, pseudochondroplasia, and multiple epiphyseal dysplasia.

As provided herein, GEP is found to be highly expressed in chondrocytes in various differentiated stages of growth plate. GEP is not significantly expressed in osteoblasts. GEP is therefore expressed in cartilage and cartilage progenitors but not in bone or bone progenitors. The GEP promoter sequence provides a cartilage-specific promoter for cartilage expression of heterologous genes and polypeptides, therapeutic molecules, reporters, or detection and imaging agents.

The invention further provides a nucleic acid promoter sequence comprising DNA sequence upstream of GEP. In a particular embodiment, the promoter sequence comprising the nucleic acid sequence set out in FIG. 20 and SEQ ID NO: 13. The promoter sequence, including upstream sequences to 1573, is capable of conferring chondrocyte expression to a heterologous sequence, including but not limited to a reporter sequence. The promoter sequence provides for expression of a heterologous sequence or a portion, of GEP sequence in chondrocytes and mesenchymal cells, including cell lines. Sequences joined to the GEP promoter are expressed in chondrocytes and cartilage and are not significantly expressed in osteoblasts.

The invention thus provides an isolated nucleic acid promoter sequence capable of conferring cartilage-specific expression upon a heterologous sequence, said promoter sequence comprising the GEP promoter sequence of SEQ ID NO: 13 or a portion thereof sufficient to confer cartilage-specific expression.

The invention provides a method for expressing a gene or polypeptide in cartilage or chondrocytes comprising fusing a hetereologous gene or encoding nucleic acid to the promoter sequence of GEP. The present invention further provides a method for imaging cartilage or evaluating cartilage in an animal comprising administering a GEP promoter sequence fused or covalently linked to a heterologous gene or nucleic acid encoding a reporter, imaging agent or diagnostic ligand to an animal, such that the heterologous gene, reporter, imaging agent or ligand is expressed in the animal's cartilage and thereby labels or puts an indicator in or at the cartilage in the animal.

The invention thus provides a method for labeling or imaging chondrocytes or cartilage in vitro or in an animal comprising administering to cells or tissue in vitro or to said animal a GEP promoter sequence fused or covalently linked to a heterologous gene or nucleic acid encoding a reporter, imaging agent or diagnostic ligand, such that the heterologous gene, reporter, imaging agent or ligand is expressed in the chondrocytes or the animal's cartilage and thereby labels or puts an indicator in or at the chondrocytes or the cartilage. In such method, the promoter sequence of GEP may comprise SEQ ID NO: 13 or a portion thereof sufficient to confer chondrocyte or cartilage-specific expression.

The present invention further related to methods and compositions for the specific inhibition of GEP. The compositions and methods inhibit the expression and/or activity of GEP. In particular, the invention provides genetic approaches and nucleic acids for the specific inhibition of GEP. In one such aspect, the invention provides antisense nucleic acids and oligonucleotides that are complementary to at least a portion of the GEP mRNA. Thus, antisense nucleic acids are provided which are complimentary to a region of about 15 nucleotides of GEP mRNA, including a portion of the GEP mRNA as set out in SEQ ID NO: 1 or SEQ ID NO: 3. The antisense nucleic acid is selected from RNA, DNA, or other synthetic or modified nucleic acid.

The antisense nuclei acid may be complementary to a translation initiation site, 5' untranslated region, coding region or 3' untranslated region of mRNA encoding GEP. Oligonucleotides and antisense nucleic acids are preferably from about 8 to about 50 nucleotides, particularly from 10 to 30 nucleotides, further particularly from about 15 to 25 nucleotides.

In a particular aspect, the nucleic acids and oligonucleotides of the present invention may be modified, either by manipulation of the chemical backbone of the nucleic acids or by covalent or non-covalent attachment of other moieties. In each or any case, such manipulation or attachment may serve to modify the stability, cellular, tissue or organ uptake, or otherwise enhance efficacy of the nucleic acids and oligonucleotides. In further aspects of the invention, the oligonucleotides may be covalently linked to other molecules, including but not limited to polypeptides, carbohydrates, lipid or lipid-like moieties, ligands, chemical agents or compounds, which may serve to enhance the uptake, stability or to target the oligonucleotides.

In further embodiments, the oligonucleotides of the present invention are modified in their chemical backbone. Specific examples of some preferred oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. In a particular embodiment, the oligonucleotides comprise at least one phosphorothioate (P—S) linkage. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., Science, 1991, 254, 1497). Oligonucleotides may also contain one or more substituted sugar moieties.

The invention includes additional compositions which can inhibit the expression of a protein, in particular GEP, at the transcriptional level by blocking translation of GEP mRNA or by facilitating destruction or destabilization of the RNA such that translation cannot efficiently take place. In this aspect, the invention provides a ribozyme that cleaves GEP mRNA.

The use of RNA inference strategies to inhibit the expression of GEP is further embodied in the invention. Thus methods of RNA interference and small interfering RNA compositions are included in the methods and composition of the present invention. In one such embodiment GEP-specific siRNA is provided against a target sequence GCCUAUC- CAAGAACUACAC (SEQ ID NO: 14), which is located about 775 bp downstream of the start codon.

The present invention also relates to a recombinant DNA molecule or cloned gene, or a degenerate variant thereof, which encodes GEP or an active fragment thereof; preferably a nucleic acid molecule, in particular a recombinant DNA molecule or cloned gene, encoding the GEP or an active fragment thereof has a nucleotide sequence or is complementary to a DNA sequence shown in SEQ ID NO: 1 or 3. In another embodiment, the recombinant DNA molecule encodes GEP or an active fragment thereof selected from the polypeptides set out in SEQ ID NO: 2, 4, 15-19 or 22.

The present invention also includes the preparation of plasmids including such vectors, and the use of the DNA sequences to construct vectors expressing antisense RNA or ribozymes which would attack the GEP mRNAs of any or all of the GEP DNA sequences set forth in SEQ ID NOS: 1 and 3 or portions thereof. Correspondingly, the preparation of antisense RNA and ribozymes are included herein.

In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present GEP or active fragment(s) thereof, and more particularly, the complete DNA sequence determined from the sequences set forth above and in SEQ ID NO: 1 and 3.

According to other preferred features of certain preferred embodiments of the present invention, a recombinant expression system is provided to produce biologically active polypeptides or express polypeptides, reporters, indicators, labels or heterologous polypeptides in cartilage or chondrocytes using nucleic acid comprising the promoter for GEP. An exemplary promoter sequence of GEP is provided in FIG. 20 (SEQ ID NO: 13.

The present invention naturally contemplates several means for preparation of the GEP, active fragments thereof, or modulators thereof, including as illustrated herein known recombinant techniques, and the invention is accordingly intended to cover such synthetic preparations within its scope.

The invention includes an assay system for screening of potential drugs effective to modulate the activity or expression of GEP or active fragments thereof. In one such instance, the modulator may affect the interaction of GEP and COMP. In a further instance, the test drug could be administered to a cellular sample with GEP, an active fragment thereof, or an extract containing GEP or active granulins, to determine its effect upon the binding activity of GEP or any of the granulins to COMP in the presence of the test drug, by comparison with a control.

The assay system could more importantly be adapted to identify drugs or other entities that are capable of binding to GEP or active fragments (e.g. granulins) thereof, thereby inhibiting or potentiating GEP or its active fragment(s)' activity. Such assay would be useful in the development of drugs that would be specific against particular cellular activity, or that would potentiate such activity, in time or in level of activity. For example, such drugs might be used to treat or alleviate arthritis, stimulate cartilage repair, stimulate the differentiation to or production of chondrocytes from mesenchymal stem cells or other stem cells, or to treat other pathologies, or cartilage or chondrocyte defects In yet a further embodiment, the invention contemplates antagonists of the activity of GEP or its active fragments. In particular, an agent or molecule that inhibits the expression or activity of GEP or inhibits the production of GEP from its mRNA. In a specific embodiment, the antagonist can be a peptide having the sequence of a portion of COMP or of a granulin.

The present invention likewise extends to the development of antibodies against GEP, including neutralizing antibodies which block or diminish its interaction with COMP for instance, including naturally raised and recombinantly prepared antibodies. Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating GEP activity.

Thus, the GEP or active fragments thereof, their analogs and/or analogs, and any antagonists or antibodies that may be raised thereto, are capable of use in connection with various diagnostic techniques, including imaging, immunoassays, such as a radioimmunoassay, using for example, an antibody to GEP that has been labeled by either radioactive addition, or radioiodination.

In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

In the instance where a radioactive label, such as the isotopes $^{3}$H, $^{14}$C, $^{32}$P, $^{35}$S, $^{36}$Cl, $^{51}$Cr, $^{57}$Co, $^{58}$CO, $^{59}$Fe, $^{99}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The present invention includes an assay system which may be prepared in the form of a test kit for the quantitative analysis of the extent of the presence of GEP or granulings, or to identify drugs or other agents that may mimic or block their activity. The system or test kit may comprise a labeled component prepared by one of the radioactive and/or enzymatic techniques discussed herein, coupling a label to the GEP or granulin, their agonists and/or antagonists, and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the GEP its active fragments such as granulins, its (or their) subunits, or upon agents or other drugs determined to possess the same activity. A first therapeutic method is associated with the prevention of the manifestations of conditions causally related to or following the damaging of cartilage or reduction in chondrocytes, and comprises administering an agent capable of modulating the production and/or activity of the GEP or subunits thereof, either individually or in mixture with each other in an amount effective to alleviate or prevent the development of those conditions in the host.

More specifically, the therapeutic method generally referred to herein could include the method for the treatment of various pathologies or other cellular dysfunctions and derangements by the administration of pharmaceutical compositions that may comprise effective inhibitors or enhancers of activation of the GEP or its subunits, or other equally effective drugs developed for instance by a drug screening assay prepared and used in accordance with a further aspect of the present invention In particular, the proteins of whose sequences are presented in SEQ ID NOS: 2, 4, 15-19 and 22 herein, their antibodies, agonists, antagonists, or active fragments thereof, could be prepared in pharmaceutical formulations for administration in instances wherein therapy is appropriate, such as to treat in therapy. The specificity of the proteins hereof would make it possible to better manage the efficacy and aftereffects of current cartilage repair therapy and the damaging effects or arthritis or chronic or significant sports injuries, and would thereby make it possible to apply GEP or active fragments thereof as a general cartilage agent.

It is a still further object of the present invention to provide a method for the treatment of mammals to control the amount or activity of the GEP or active fragments thereof or subunits thereof, so as to alter the adverse consequences of such presence or activity, or where beneficial, to enhance such activity.

It is a still further object of the present invention to provide a method for the treatment of mammals to control the amount or activity of the GEP or its subunits, so as to treat or avert the adverse consequences of invasive, spontaneous or idiopathic pathological states.

It is a still further object of the present invention to provide pharmaceutical compositions for use in therapeutic methods which comprise or are based upon the GEP or active fragments thereof, including granulins, their binding partner(s), or upon agents or drugs that control the production, or that mimic or antagonize the activities of the GEP or active fragments thereof.

Other objects and advantages will become apparent to those skilled in the art from a review of the following description which proceeds with reference to the following illustrative drawings.

BRIEF DESCRIPTION OF THE DRAWINGS

FIG. 20 depicts the nucleotide sequence of upstream sequence of human GEP (SEQ ID NO: 13). Consensus sequence sites for transcription factors Smad3, AML/CBFA2, Smad4, E2F and NF-KB are underlined.

FIGS. 21A and 21B depicts expression of luciferase from GEP-promoter sequences. (A) Upstream flanking region (−1573 to +325) of the human GEP gene sequence was cloned upstream of a region encoding luciferase in the pGL2 basic vector to generate pGL2-GEP-luc. (B) Luciferase activity in RCS (chondrosarcoma), 10T1/2 cells (pluripotent murine mesenchymal cell line), C2C12 cells (pluripotent murine mesenchymal cell line) and Saos-2 cells (osteosarcoma) after transfection with control pGL2 Basic plasmid or GEP promoter pGL2-GEP-luc plasmid is graphed.

FIG. 23 depicts deletion of GEP expression in growth plate of knockdown mice (KD) versus widtype (WT). Tibia was analyzed at 3 weeks of age using immunohistochemistry as described.

FIG. 25 depicts reduction of growth plate width in GEP knockdown (KD) mice versus wildtype (WT). Tibia at 3 weeks is assessed by Safranin O staining.

reporter constructs, as indicated above, and luciferase and β-galactosidase assays were performed.

Figure 29:
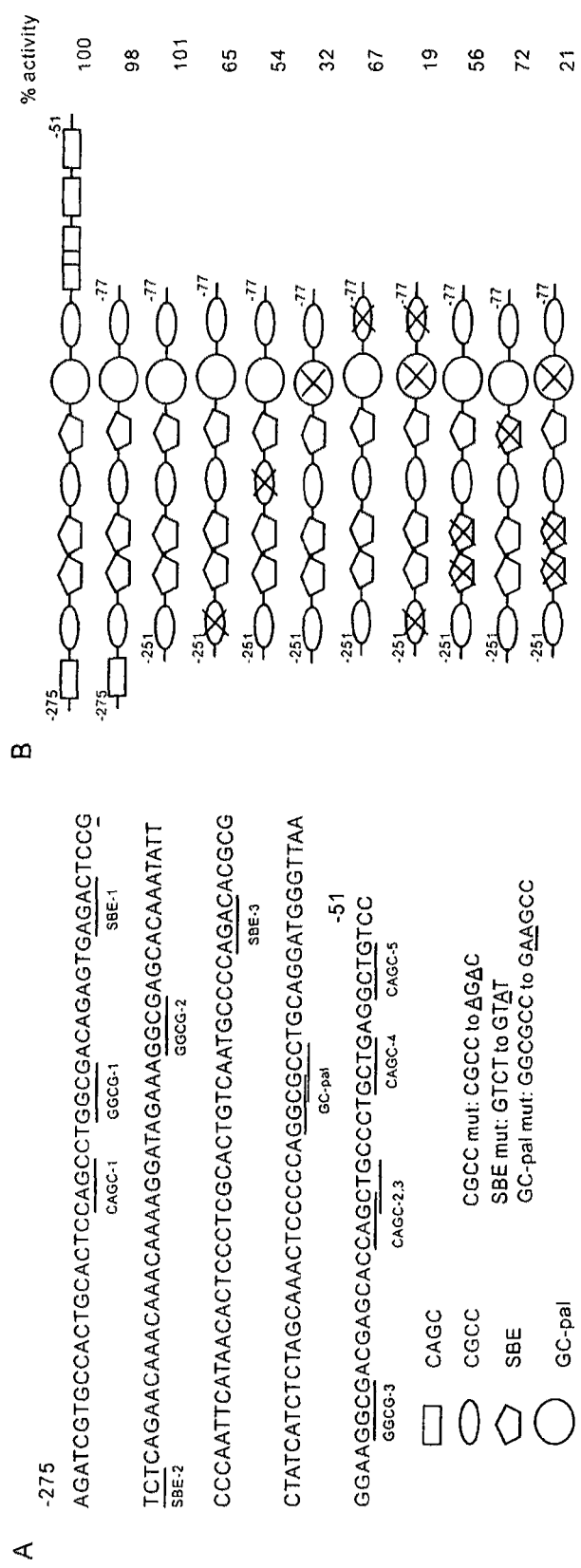

FIG. 29 provides identification of BMP-responsive elements in the human GEP minimal promoter (−275 to −51) (SEQ ID NO: 24). Mutations in CAGC box, SMAD-binding site (SBE) or GC-rich sequence elements were generated by site-directed mutagenesis in GEP-specific reporter construct GEP-(−275/−51). The wild-type CGCC elements were replaced by AGAC mutated sequence, SBE (GTCT) sites were mutated GTAT, and the wild type GGCGCC palindrome sequence element (GC-pal) was replaced with GAAGCC, respectively. Wild-type and mutated GEP promoter luciferase constructs were transfected into RCS cells and subsequently treated with or without BMP-2 (100 ng/ml). Fold-induction values in the presence of BMP2 compared with wildtype GEP reporter construct, which was set as 100.

Figure 30:
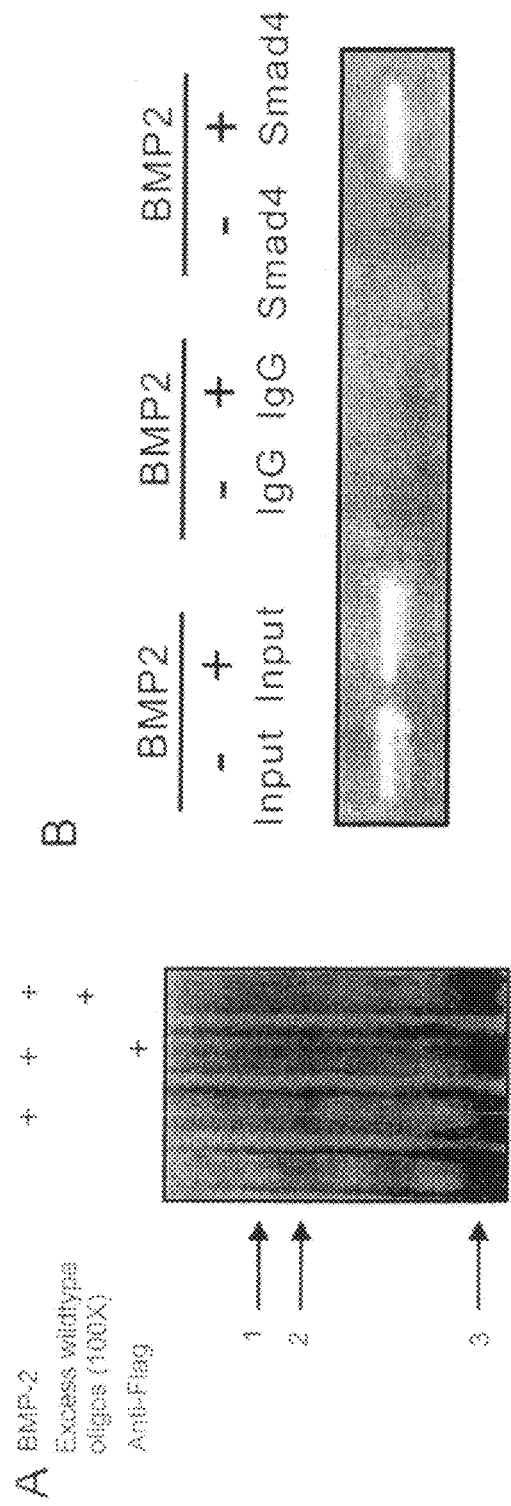

FIG. 30 shows BMP2-activated SMAD4 binds to GEP minimal promoter. (A) SMAD4 binds to the GEP minimal promoter (−275 to −51) in vitro (EMSA). 10 μg of nuclear extracts prepared from RCS cells without or with 300 ng/ml BMP-2 were mixed in the reaction buffer (20 μl). For competition experiments, a 100-fold excess of wild-type oligodeoxynucleotide was added. For supershift assays, anti-SMAD4 IgG (0.5 μg) was included. After 15 min of incubation, the DIG-labeled probe was added, and the reaction mixture was incubated for a further 15 min and analyzed by gel electrophoresis. The positions of the supershifted IgG/SMAD4/GEP minimal promoter complex, the SMAD4/GEP minimal promoter complex, and the free DNA probe are indicated as 1, 2, and 3, respectively. (B) BMP2 activated SMAD4 associates with GEP minimal promoter in vivo (ChIP). RCS cells treated with or without 300 ng/ml BMP-2 for 12 hours were cross-linked by formaldehyde treatment and lysed. Cell lysates were subjected to immunoprecipitation with control IgG, or anti-SAMD4. Purified DNA from the cell lysate (Input DNA, serves as a positive control) and DNA recovered from immunoprecipitation were amplified by PCR using specific primers for GEP minimal promoter.

Figure 31:
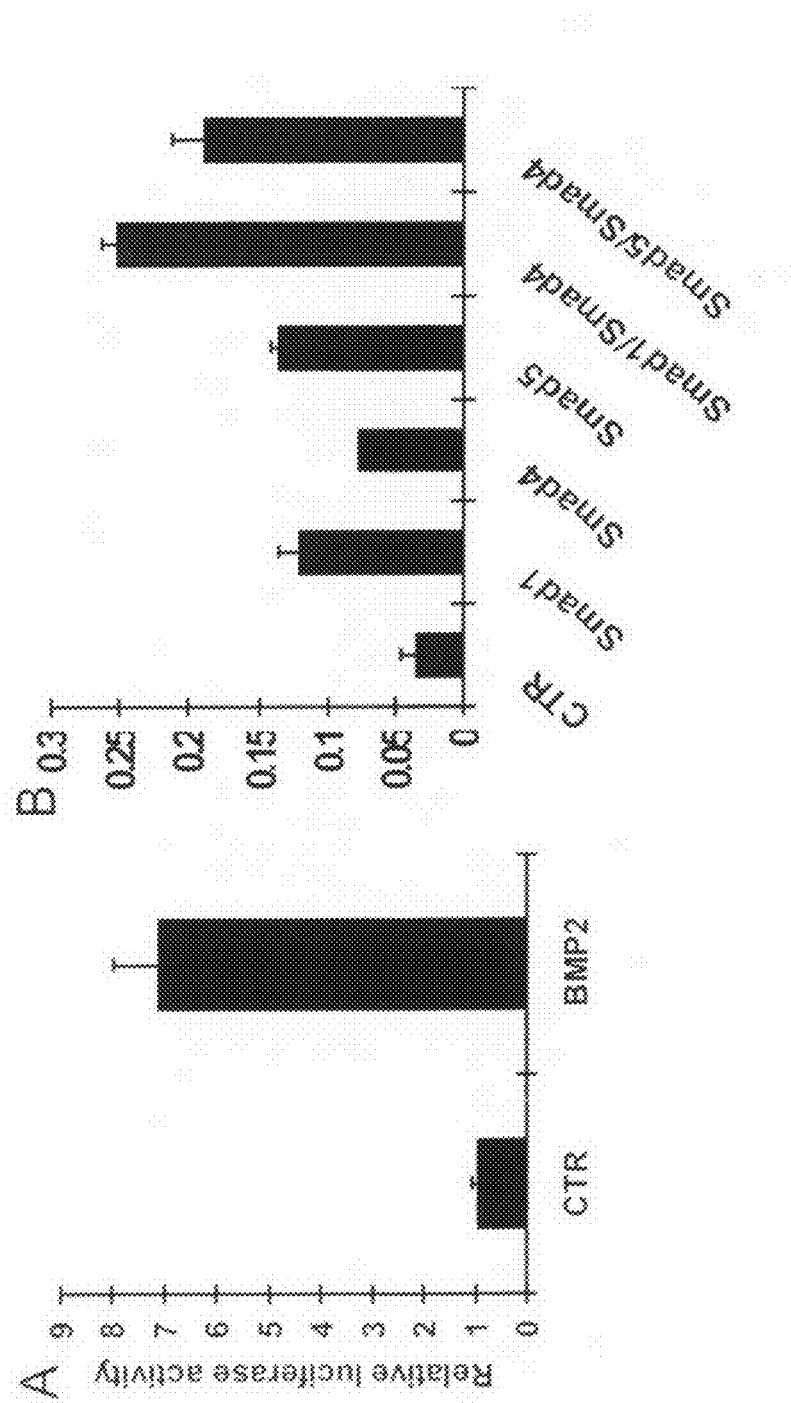

FIG. 31 shows BMP2 downstream transcription factor Smads can activate the GEP-specific reporter genes. (A) BMP-2 treatment enhances the expression of GEP-specific reporter gene. The GEP-specific reporter construct −1575GEPluc and a pSVgal internal control plasmid were transfected into RCS cells in the presence or absence of 300 ng/ml of BMP-2 for 48 hr and the cultures were harvested and lysed and the β-galactosidase and luciferase activities determined. (B) The GEP-specific reporter construct −1575GEPluc was transfected into RCS cells together with the indicated Smad expression plasmids (i.e., Smad1, Smad4, and Smad5), as well as a pSVgal internal control plasmid. At 48 hr after transfection the cultures were harvested and processed as described.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "granulin-epithelin precursor", "GEP", "PC-cell-derived growth factor", "PCDGF", "progranulin", "pgrn", "proepithelin", "acrogranin", and "GP80" and any variants not specifically listed, may be used herein interchangeably, and as used throughout the present application and claims refer to proteinaceous material including single or multiple proteins, and active fragments thereof and extends to those proteins having the amino acid sequence data described herein and presented in SEQ ID NOS: 2, 4, or 22 and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "granulin-epithelin precursor", "GEP", "PC-cell-derived growth factor", "PCDGF", "progranulin", "pgrn", "proepithelin", "acrogranin", and "GP80" are intended to include within their scope proteins specifically recited herein as well as all substantially homologous analogs and allelic variations.

The terms "granulin(s)", "epithelins" or any of "Granulins A-E", "GrnA", "GrnB", "GrnC", "GrnD", "GrnE" refer to particular cysteine rich motifs, of approximately 6 kDa in size, including comprising or having the sequence motif $CX_{5-6}CX_5CCX_8CCX_6CCXDX_2HCCPX_4CX_{5-6}C$ (SEQ ID NO: 5), which granulins can be released by proteolytic processing from the GEP polypeptide molecule. These granulin(s) retain biological activity and are active in cell growth assays. The granulins represent active fragments of GEP. Exemplary granulin sequences include those proteins having the amino acid sequence data described herein and presented in SEQ ID NOS 2, 4 or 22 or fragments thereof, for example granulin fragments including as set out in SEQ ID NOS: 15-19, and the profile of activities set forth herein. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "granulin(s)", "epithelins" or any of "Granulins A-E", "GrnA", "GmB", "GmC", "GrnD", "GrnE" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its' either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding GEP or active fragments thereof which code for a GEP or active fragment comprising or having the same amino acid sequence as set out in any of SEQ ID NOS: 2, 4, 15-19, or 22 but which are degenerate to SEQ ID NO: 1 or 3 any of SEQ ID NOS: 1 or 3 or the portions of SEQ ID NOS: 1 or 3 which encode any of SEQ ID NOS: 15-19. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG o rAGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in SEQ ID NO: 1 or 3 or any GEP encoding sequence such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino Acids with Nonpolar R Groups:

Alanine, Valine, Leucine, Isoleucine, Proline, Phenylalanine, Tryptophan, Methionine Amino Acids with Uncharged Polar R Groups:

Glycine, Serine, Threonine, Cysteine, Tyrosine, Asparagine, Glutamine

Amino Acids with Charged Polar R Groups (Negatively Charged at Ph 6.0):

Aspartic acid, Glutamic acid

Basic Amino Acids (Positively Charged at Ph 6.0):

Lysine, Arginine, Histidine (at pH 6.0)

Another Grouping May be Those Amino Acids with Phenyl Groups:
Phenylalanine, Tryptophan, Tyrosine
Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly Preferred Substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces.—turns in the protein's structure.

Analog peptides which mimic one or more capability or activity of the polypeptides of the present invention, including the active fragments thereof, may be generated and screened using methods and skills known in the art. Such analog peptides or peptidomimetics may be comprised of traditional and/or non-traditional amino acids and combinations thereof. Small molecule compounds which mimic the activity of the peptides are also contemplated. Peptide mimics may be screened and isolated from peptide libraries or compound libraries, including random peptide phage display (RPPD) libraries.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', $F(ab')_2$ and F(v), which portions are preferred for use in the therapeutic methods described herein.

Fab and $F(ab')_2$ portions of antibody molecules are prepared by the proteolytic reaction of papain and pepsin, respectively, on substantially intact antibody molecules by methods that are well-known. See for example, U.S. Pat. No. 4,342,566 to The ofilopolous et al. Fab' antibody molecule portions are also well-known and are produced from $F(ab')_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20°C below the predicted or determined $T_m$ with washes of higher stringency, if desired.

Research efforts focusing on identifying the growth factors regulating chondrogenesis are crucial not only to gain a better understanding of actions of growth factors in cartilage biology but also to develop and optimize the biologically based treatment for several orthopedic conditions, including fractures, cartilage defects, arthritis, and tumors. In an effort to investigate the biological role of cartilage oligomeric matric protein (COMP), a major noncollagenous extracellular matrix protein of cartilage, full-length granulin (granulin/epithelin precursor (GEP)) was isolated as a binding partner of COMP in a functional genetic screen followed by confirmatory GST pull down and co-immunoprecipitation assays. GEP and its processed granulins are emerging as multifunctional regulators of cell proliferation, differentiation, development, migration and wound healing in various biological and pathophysiological processes. The studies provided herein demonstrate that 1) Expression of GEP in embryonic musculoskeletal tissues appears to be restricted to chondrocytes and is concentrated in areas where ossification will occur; 2) GEP is expressed predominantly in the pericellular matrix of adult human chondrocytes and co-localizes with COMP; 3) the expression of GEP in human chondrocytes is strongly induced by BMP-2 and TGF-β, two critical chondrogenic growth factors, and especially by proinflammatory cytokine TNF-alpha; 4) GEP is secreted into the medium of cultured cartilage explants and its secretion is affected by known chondrogenic growth factors and inflammatory cytokines; 5) GEP level is significantly elevated in the cartilage of patients with arthritis; and 6) GEP stimulates chondrocyte proliferation. These findings and known functions of GEP and its derivatives in the control of cell growth and differentiation provide a foundation for instant application's central hypothesis that GEP and its processed granulins are novel chondrogenic growth factors and play a previously unrecognized important role in the chondrogenesis and pathology of arthritis.

Applications of this invention include but are not limited to: 1) to directly recruit GEP (recombinant protein and DNA), its processed units, their analogous compounds, or their combinations with other well-characterized chondroinductive factors to devise a novel treatment for cartilage repair; 2) to utilize MSCs, chondrocytes, chondrocyte progenitors or other cells bearing GEP or its analogous compounds for cartilage disorders; 3) to employ GEP or its analogous compounds for treating arthritis or cartilage disorders; and 4) to inactivate the antagonists of GEP for devising new treatments for cartilage repair and arthritis.

In accordance with the present invention, a method for modulating chondrogenesis is provided comprising modulating the expression or activity of GEP. In a particular such aspect, the differential growth or proliferation of cartilage or chondrocytes is increased by modulation of GEP. The invention provides a method for producing cartilage at a cartilage defect site comprising administering, including at the defect site, GEP, an active fragment thereof, including but not limited to a granulin, such that the production of cartilage is stimulated. The invention provides a method for producing cartilage at a cartilage defect site comprising administering, including at the defect site, a modulator of GEP such that the production of cartilage is stimulated.

In a further aspect, the differentiation of stem cells, particularly mesenchymal stem cells or cells capable of differentiating along the mesenchymal pathway, including for instance differentiating to chondrocytes and chondrocyte progenitors, is enhanced along the mesenchymal or chondrocyte lineage. The invention thus provides a method for stimulating the proliferation or differentiation of chondrocytes in an animal comprising administering to said animal GEP or an active fragment thereof. In a further aspect, the invention provides a method for stimulating the proliferation or differentiation of chondrocytes in vitro or in culture comprising administering to said culture, or under in vitro conditions, GEP or an active fragment thereof. In one such aspect GEP or an active fragment thereof is administered in combination with chondrocyte progenitors, mesenchymal stem cells or stem cells capable of differentiating along the mesenchymal lineage. In a further such embodiment, GEP or an active fragment thereof is administered to chondrocyte progenitors, mesenchymal stem cells or stem cells capable of differentiating along the mesenchymal lineage in vitro or in culture, to stimulate such cells prior to the administration of said stimulated cells to an animal.

In an aspect of the invention, GEP or active fragments or portions thereof, including but not limited to the granulin(s), can be combined with chondrocyte progenitors, mesenchymal stem cells, or stem cells capable of differentiating along the mesenchymal lineage to provide cell therapy compositions. Such compositions or combinations may be utilized for cartilage repair, regeneration or therapy. In one such aspect, arthritis or cartilage damage is reduced or repaired by administration of GEP, or active fragement(s) thereof, in combination or in series with chondrocyte progenitors or stem cells, or by administration of stem cells pre-stimulated by incubation with GEP or an active fragment or portion thereof.

A method for the modulation or alleviation of arthritis is provided comprising administering GEP or an active fragment or portion thereof. A method for cartilage repair is further provided comprising administering GEP or an active fragment or portion thereof. Any such methods may alternatively or additionally utilize administration of modulators of GEP activity or expression. Such modulators may include agents, agonists, antagonists, inhibitors or activators of GEP.

In a further aspect, the invention relates to the application of nucleic acid therapy using nucleic acid encoding GEP or active fragments thereof for the repair and regeneration of cartilage. Thus, nucleic acid therapy vectors encoding GEP or active fragment(s) thereof may be utilized to express GEP or active fragment(s) in cartilage, chondrocytes, chondrocyte progenitors or mesenchymal stem cells. Alternatively, naked DNA, which is not in a replicable vector or infecting vector, and whereupon GEP is only transiently expressed, can be utilized to bring about GEP expression in cartilage, chondrocytes, chondrocyte progenitors or mesenchymal stem cells. In one particular such aspect, the invention encompasses the introduction of naked DNA encoding GEP or active fragment(s) thereof, whose expression stimulates and otherwise facilitates the repair and regeneration of cartilage. Methods for expressing a bioactive agent in chondrocytes in vivo comprising administering naked DNA encoding one or more bioactive agent to a region in vivo where chondrocytes or chondrocyte progenitors are located such that the chondrocytes or chondrocyte progenitors take up the naked DNA and express the bioactive agent(s) are provided for example in DiCesare et al U.S. patent application Ser. No. 10/886,947 and published in WO 2005/007098, which is incorporated herein by reference in its entirety. Bioactive agents are selected from the group of cartilage morphogens and factors or peptides which block inhibitory signals preventing the repair or regeneration of cartilage. In an exemplary embodiment, DiCesare et al demonstrates naked DNA therapy wherein the agent is BMP-2.

The therapeutic methods include the treatment of various conditions, particularly various orthopedic and rheumatologic conditions, including degenerative connective tissue disorders or in the event of physical trauma. The methods include administration in instances where cartilage repair and/or regeneration is appropriate, such as to treat cartilage defects, osteoarthritis, collagen disorders, dwarfism, including camptomelic dysplasia, pseudochondroplasia, and multiple epiphyseal dysplasia.

As provided herein, GEP is found to be highly expressed in chondrocytes in various differentiated stages of growth plate. GEP is not significantly expressed in osteoblasts. GEP is therefore expressed in cartilage and cartilage progenitors but not in bone or bone progenitors. The GEP promoter sequence provides a cartilage-specific promoter for cartilage expression of heterologous genes and polypeptides, therapeutic molecules, reporters, or detection and imaging agents.

The invention further provides a nucleic acid promoter sequence comprising DNA sequence upstream of GEP. In a particular embodiment, the promoter sequence comprising the nucleic acid sequence set out in FIG. 20 and SEQ ID NO: 13. The promoter sequence, including upstream sequences to 1573, is capable of conferring chondrocyte expression to a heterologous sequence, including but not limited to a reporter sequence. The promoter sequence provides for expression of a heterologous sequence or a portion of GEP sequence in chondrocytes and mesenchymal cells, including cell lines. Sequences joined to the GEP promoter are expressed in chondrocytes and cartilage and are not significantly expressed in osteoblasts.

The invention provides a method for expressing a gene or polypeptide in cartilage or chondrocytes comprising fusing a hetereologous gene or encoding nucleic acid to the promoter sequence of GEP. The present invention further provides a method for imaging cartilage or evaluating cartilage in an animal comprising administering a GEP promoter sequence fused or covalently linked to a heterologous gene or nucleic acid encoding a reporter, imaging agent or diagnostic ligand to an animal, such that the heterologous gene, reporter, imaging agent or ligand is expressed in the animal's cartilage and thereby labels or puts an indicator in or at the cartilage in the animal.

The present invention further related to methods and compositions for the specific inhibition of GEP. The compositions and methods inhibit the expression and/or activity of GEP. In particular, the invention provides genetic approaches and nucleic acids for the specific inhibition of GEP. In one such aspect, the invention provides antisense nucleic acids and oligonucleotides that are complementary to at least a portion of the GEP mRNA. Thus, antisense nucleic acids are provided which are complimentary to a region of about 15 nucleotides of GEP mRNA, including a portion of the GEP mRNA as set out in SEQ ID NO: 1 or SEQ ID NO: 3. The antisense nucleic acid is selected from RNA, DNA, or other synthetic or modified nucleic acid.

The antisense nucleic acid may be complementary to a translation initiation site, 5' untranslated region, coding region or 3' untranslated region of mRNA encoding GEP. Oligonucleotides and antisense nucleic acids are preferably from about 8 to about 50 nucleotides, particularly from 10 to 30 nucleotides, further particularly from about 15 to 25 nucleotides.

In a particular aspect, the nucleic acids and oligonucleotides of the present invention may be modified, either by manipulation of the chemical backbone of the nucleic acids or by covalent or non-covalent attachment of other moieties. In each or any case, such manipulation or attachment may serve to modify the stability, cellular, tissue or organ uptake, or otherwise enhance efficacy of the nucleic acids and oligonucleotides. In further aspects of the invention, the oligonucleotides may be covalently linked to other molecules, including but not limited to polypeptides, carbohydrates, lipid or lipid-like moieties, ligands, chemical agents or compounds, which may serve to enhance the uptake, stability or to target the oligonucleotides.

In further embodiments, the oligonucleotides of the present invention are modified in their chemical backbone. Specific examples of some preferred oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. In a particular embodiment, the oligonucleotides comprise at least one phosphorothioate (P—S) linkage. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al. (1991) Science 254:1497). Oligonucleotides may also contain one or more substituted sugar moieties.

The invention includes additional compositions which can inhibit the expression of a protein, in particular GEP, at the transcriptional level by blocking translation of GEP mRNA or by facilitating destruction or destabilization of the RNA such that translation cannot efficiently take place. In this aspect, the invention provides a ribozyme that cleaves GEP mRNA.

The use of RNA inference strategies to inhibit the expression of GEP is further embodied in the invention. Thus methods of RNA interference and small interfering RNA compositions are included in the methods and composition of the present invention. In one such embodiment GEP-specific siRNA is provided against a target sequence GCCUAUC-CAAGAACUACAC (SEQ ID NO: 14), which is located about 775 bp downstream of the start codon.

The present invention also relates to a recombinant DNA molecule or cloned gene, or a degenerate variant thereof, which encodes GEP or an active fragment thereof and uses thereof; preferably a nucleic acid molecule, in particular a recombinant DNA molecule or cloned gene, encoding the GEP or an active fragment thereof has a nucleotide sequence or is complementary to a DNA sequence shown in SEQ ID NO: 1 or 3. In another embodiment, the recombinant DNA molecule encodes GEP or an active fragment thereof selected from the polypeptides set out in SEQ ID NO: 2, 4, 15-19 or 22.

The present invention also includes the preparation of plasmids including such vectors, and the use of the DNA sequences to construct vectors expressing antisense RNA or ribozymes which would attack the GEP mRNAs of any or all of the GEP DNA sequences set forth in SEQ ID NOS: 1 or 3 or portions thereof. Correspondingly, the preparation of antisense RNA and ribozymes are included herein.

In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present GEP or active fragment(s) thereof, and more particularly, the complete DNA sequence determined from the sequences set forth above and in SEQ ID NO: 1 and 3.

According to other preferred features of certain preferred embodiments of the present invention, a recombinant expression system is provided to produce biologically active polypeptides or express polypeptides, reporters, indicators, labels or heterologous polypeptides in cartilage or chondrocytes using nucleic acid comprising the promoter for GEP. An exemplary promoter sequence of GEP is provided in FIG. 20 (SEQ ID NO: 13).

The present invention naturally contemplates several means for preparation of the GEP, active fragments thereof, or modulators thereof, including as illustrated herein known recombinant techniques, and the invention is accordingly intended to cover such synthetic preparations within its scope.

The invention includes an assay system for screening of potential drugs effective to modulate the activity or expression of GEP or active fragments thereof. In one such instance, the modulator may affect the interaction of GEP and COMP. In a further instance, the test drug could be administered to a cellular sample with GEP, an active fragment thereof, or an extract containing GEP or active granulins, to determine its effect upon the binding activity of GEP or any of the granulins to COMP in the presence of the test drug, by comparison with a control.

The assay system could more importantly be adapted to identify drugs or other entities that are capable of binding to GEP or active fragments (e.g. granulins) thereof, thereby inhibiting or potentiating GEP or its active fragment(s)' activity. Such assay would be useful in the development of drugs that would be specific against particular cellular activity, or that would potentiate such activity, in time or in level of activity. For example, such drugs might be used to treat or alleviate arthritis, stimulate cartilage repair, stimulate the differentiation to or production of chondrocytes from mesenchymal stem cells or other stem cells, or to treat other pathologies, or cartilage or chondrocyte defects In yet a further embodiment, the invention contemplates antagonists of the activity of GEP or its active fragments. In particular, an agent or molecule that inhibits the expression or activity of GEP or inhibits the production of GEP from its mRNA. In a specific embodiment, the antagonist can be a peptide having the sequence of a portion of COMP or of a granulin.

The present invention likewise extends to the development of antibodies against GEP, including neutralizing antibodies which block or diminish its interaction with COMP for instance, including naturally raised and recombinantly prepared antibodies. Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating GEP activity.

Thus, the GEP or active fragments thereof, their analogs and/or analogs, and any antagonists or antibodies that may be raised thereto, are capable of use in connection with various diagnostic techniques, including imaging, immunoassays, such as a radioimmunoassay, using for example, an antibody to GEP that has been labeled by either radioactive addition, or radioiodination.

In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The present invention includes an assay system which may be prepared in the form of a test kit for the quantitative analysis of the extent of the presence of GEP or granulings, or to identify drugs or other agents that may mimic or block their activity. The system or test kit may comprise a labeled component prepared by one of the radioactive and/or enzymatic techniques discussed herein, coupling a label to the GEP or granulin, their agonists and/or antagonists, and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the GEP its active fragments such as granulins, its (or their) subunits, or upon agents or other drugs determined to possess the same activity. A first therapeutic method is associated with the prevention of the manifestations of conditions causally related to or following the damaging of cartilage or reduction in chondrocytes, and comprises administering an agent capable of modulating the production and/or activity of the GEP or subunits thereof, either individually or in mixture with each other in an amount effective to alleviate or prevent the development of those conditions in the host.

More specifically, the therapeutic method generally referred to herein could include the method for the treatment of various pathologies or other cellular dysfunctions and derangements by the administration of pharmaceutical compositions that may comprise effective inhibitors or enhancers of activation of the GEP or its subunits, or other equally effective drugs developed for instance by a drug screening assay prepared and used in accordance with a further aspect of the present invention In particular, the proteins of whose sequences are presented in SEQ ID NOS:2, 4, 15-19 and 22 herein, their antibodies, agonists, antagonists, or active fragments thereof, could be prepared in pharmaceutical formulations for administration in instances wherein therapy is appropriate, such as to treat in therapy. The specificity of the proteins hereof would make it possible to better manage the efficacy and aftereffects of current cartilage repair therapy and the damaging effects or arthritis or chronic or significant sports injuries, and would thereby make it possible to apply GEP or active fragments thereof as a general cartilage agent.

It is a still further object of the present invention to provide a method for the treatment of mammals to control the amount or activity of the GEP or active fragments thereof or subunits thereof, so as to alter the adverse consequences of such presence or activity, or where beneficial, to enhance such activity.

It is a still further object of the present invention to provide a method for the treatment of mammals to control the amount or activity of the GEP or its subunits, so as to treat or avert the adverse consequences of invasive, spontaneous or idiopathic pathological states.

It is a still further object of the present invention to provide pharmaceutical compositions for use in therapeutic methods which comprise or are based upon the GEP or active fragments thereof, including granulins, their binding partner(s), or upon agents or drugs that control the production, or that mimic or antagonize the activities of the GEP or active fragments thereof.

The possibilities both diagnostic and therapeutic that are raised by the recognition of the expression and activity and function of GEP and active fragments thereof in cartilage and chondriocytes derive from the fact that GEP is specifically expressed in chondrocytes, and not in osteocytes, and GEP interacts with COMP. As suggested earlier and elaborated further on herein, the present invention contemplates pharmaceutical intervention in the differentiation, growth, repair and activity of chondrocytes and cartilage to modulate cartilage damage, facilitate repair and alleviate or treat arthritis and various cartilage disorders, including those instances of sports injuries.

As discussed earlier, the GEP or active fragments thereof or their binding partners or other ligands or agents exhibiting either mimicry or antagonism to the GEP or active fragments thereof or control over their production, may be prepared in pharmaceutical compositions, with a suitable carrier and at a strength effective for administration by various means to a patient experiencing an adverse medical condition associated with specific GEP or active fragments thereof for the treatment thereof. A variety of administrative techniques may be utilized, among them parenteral techniques such as subcutaneous, intravenous and intraperitoneal injections, catheterizations and the like. Average quantities of the GEP or active fragments thereof or their subunits may vary and in particular should be based upon the recommendations and prescription of a qualified physician or veterinarian.

Also, antibodies including both polyclonal and monoclonal antibodies, and drugs that modulate the production or activity of the GEP or active fragments thereof and/or their subunits may possess certain diagnostic applications and may for example, be utilized for the purpose of detecting and/or measuring conditions such as viral infection or the like. For example, the GEP or active fragments thereof or its subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the GEP or active fragments thereof of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against GEP or active fragments thereof peptides can be screened for various properties; i.e., isotype, epitope, affinity, etc. Of particular interest are monoclonal antibodies that neutralize the activity of the GEP or active fragments thereof or its subunits. Such monoclonals can be readily identified in GEP or active fragments thereof activity assays. High affinity antibodies are also useful when immunoaffinity purification of native or recombinant GEP or active fragments thereof is possible.

Preferably, the anti-GEP or active fragments thereof antibody used in the diagnostic methods of this invention is an affinity purified polyclonal antibody. More preferably, the antibody is a monoclonal antibody (mAb). In addition, it is preferable for the anti-GEP or active fragments thereof antibody molecules used herein be in the form of Fab, Fab', $F(ab')_2$ or F(v) portions of whole antibody molecules.

As suggested earlier, the diagnostic method of the present invention comprises examining a cellular sample or medium by means of an assay including an effective amount of an antagonist to a GEP or active fragments thereof/protein, such as an anti-GEP or active fragments thereof antibody, preferably an affinity-purified polyclonal antibody, and more preferably a mAb. In addition, it is preferable for the anti-GEP or active fragments thereof antibody molecules used herein be in the form of Fab, Fab', $F(ab')_2$ or F(v) portions or whole antibody molecules. As previously discussed, patients capable of benefiting from this method include those suffering from cancer, a pre-cancerous lesion, a viral infection or other like pathological derangement. Methods for isolating the GEP or active fragments thereof and inducing anti-GEP or active fragments thereof antibodies and for determining and optimizing the ability of anti-GEP or active fragments thereof antibodies to assist in the examination of the target cells are all well-known in the art.

Methods for producing polyclonal anti-polypeptide antibodies are well-known in the art. See U.S. Pat. No. 4,493,795 to Nestor et al. A monoclonal antibody, typically containing Fab and/or $F(ab')_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a GEP or active fragments thereof-binding portion thereof, or GEP or active fragments thereof, or an origin-specific DNA-binding portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present GEP or active fragments thereof and their ability to inhibit specified GEP or active fragments thereof activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal anti-GEP or active fragments thereof antibodies are also well-known in the art. See Niman et al., *Proc. Natl. Acad. Sci. USA*, 80:4949-4953 (1983). Typically, the present GEP or active fragments thereof or a peptide analog is used either alone or conjugated to an immunogenic carrier, as the immunogen in the before described procedure for producing anti-GEP or active fragments thereof monoclonal antibodies. The hybridomas are screened for the ability to produce an antibody that immunoreacts with the GEP or active fragments thereof peptide analog and the present GEP or active fragments thereof.

The present invention further contemplates therapeutic compositions useful in practicing the therapeutic methods of this invention. A subject therapeutic composition includes, in admixture, a pharmaceutically acceptable excipient (carrier) and one or more of a GEP or active fragments thereof, polypeptide analog thereof or fragment thereof, as described herein as an active ingredient. In a preferred embodiment, the composition comprises an antigen capable of modulating the specific binding of the present GEP or active fragments thereof within a target cell.

The invention provides a composition for modulating chondrogenesis comprising isolated GEP or active fragments thereof, wherein said GEP or active fragment comprises an amino acid sequence selected from SEQ ID NO: 2, 4, 15-19 and 22.

The composition may further comprise isolated cells selected from chondrocyte progenitors, mesenchymal stem cells, or stem cells capable of differentiating along the mesenchymal lineage. Alternatively, or in addition, the composition may further comprise an agent or compound for cartilage repair or regeneration. The composition may also further comprise one or more of a growth factor selected from BMP-2, TGF β, TNF α, SLPI, FGF or IL-1β. Any such pharmaceutical compositions are provided which further comprise a pharmaceutically acceptable carrier, vehicle, diluent or excipient.

In a further aspect, the differentiation of stem cells, particularly mesenchymal stem cells or cells capable of differentiating along the mesenchymal pathway, including for instance differentiating to chondrocytes and chondrocyte progenitors, is enhanced along the mesenchymal or chondrocyte lineage. The invention thus provides a method for stimulating the proliferation or differentiation of chondrocytes in an animal comprising administering to said animal GEP or an active fragment thereof. In a further aspect, the invention provides a method for stimulating the proliferation or differentiation of chondrocytes in vitro or in culture comprising administering to said culture, or under in vitro conditions, GEP or an active fragment thereof. In one such aspect GEP or an active fragment thereof is administered in combination with chondrocyte progenitors, mesenchymal stem cells or stem cells capable of differentiating along the mesenchymal lineage. In a further such embodiment, GEP or an active fragment thereof is administered to chondrocyte progenitors, mesenchymal stem cells or stem cells capable of differentiating along the mesenchymal lineage in vitro or in culture, to stimulate such cells prior to the administration of said stimulated cells to an animal.

In an aspect of the invention, GEP or active fragments or portions thereof, including but not limited to the granulin(s), can be combined with chondrocyte progenitors, mesenchymal stem cells, or stem cells capable of differentiating along the mesenchymal lineage to provide cell therapy compositions. Such compositions or combinations may be utilized for cartilage repair, regeneration or therapy. In one such aspect, arthritis or cartilage damage is reduced or repaired by administration of GEP, or active fragement(s) thereof, in combination or in series with chondrocyte progenitors or stem cells, or by administration of stem cells pre-stimulated by incubation with GEP or an active fragment or portion thereof.

Pluripotent mesenchymal stem cell(s) are capable of self renewal or differentiation into any particular lineage within the mesodermal germ layer. Pluripotent mesenchymal stem cells may form any cell type within the mesodermal lineage, including, but not limited to, skeletal muscle, smooth muscle, cardiac muscle, white fat, brown fat, connective tissue septae, loose areolar connective tissue, fibrous organ capsules, tendons, ligaments, dermis, bone, hyaline cartilage, elastic cartilage fibrocartilage, articular cartilage, growth plate cartilage, endothelial cells, meninges, periosteum, perichondrium, erythrocytes, lymphocytes, monocytes, macrophages, microglia, plasma cells, mast cells, dendritic cells, megakaryocytes, osteoclasts, chondroclasts, lymph nodes, tonsils, spleen, kidney, ureter, urinary bladder, heart, testes, ovaries, uterus, etc.

Examples of progenitor and pluripotent stem cells from the mesodermal germ layer include the unipotent myosatellite myoblasts of muscle (Mauro, 1961; Campion, 1984; Grounds et al., 1992); the unipotent adipoblast cells of adipose tissue (Ailhaud et al., 1992); the unipotent chondrogenic cells and osteogenic cells of the perichondrium and periosteum, respectively (Cruess, 1982; Young et al., 1995); the bipotent adipofibroblasts of adipose tissue (Vierck et al., 1996); the bipotent chondrogenic/osteogenic stem cells of marrow (Owen, 1988; Beresford, 1989; Rickard et al., 1994; Caplan et al., 1997; Prockop, 1997); the tripotent chondrogenic/osteogenic/adipogenic stem cells of marrow (Pittenger et al., 1999); the multipotent hematopoietic stem cells of marrow (Palis and Segel, 1998; McGuire, 1998; Ratajczak et al., 1998); the multipotent cadiogenic/hematopoietic/endotheliogenic cells of marrow (Eisenberg and Markwald, 1997); and the pluripotent mesenchymal stem cells of the connective tissues (Young et al., 1993, 1998a; Rogers et al., 1995).

Pluripotent mesenchymal stem cells and methods of isolation and use thereof are described in U.S. Pat. No. 5,827,735, issued Oct. 27, 1998, which is hereby incorporated by reference in its entirety. Further compositions of such pluripotent mesenchymal stem cells and the particular use of pluripotent mesenchymal stem cells in cartilage repair are described in U.S. Pat. No. 5,906,934, issued May 25, 1999, which is hereby incorporated by reference in its entirety. U.S. Pat. No. 5,486,359 of Caplan et al provides compositions of human mesenchymal stem cells and U.S. Pat. No. 5,226,914 provides methods for treating connective tissue disorders with mesenchymal stem cells.

Progenitor or pluripotent stem cell populations having mesodermal lineage capability have been isolated from multiple animal species, e.g., avians (Young et al., 1992a, 1993, 1995), mice (Rogers et al., 1995; Saito et al., 1995; Young et al., 1998a), rats (Grigoriadis et al., 1988; Lucas et al., 1995, 1996; Dixon et al., 1996; Warejcka et al., 1996), rabbits (Pate et al., 1993; Wakitani et al., 1994; Grande et al., 1995; Young, R. G. et al., 1998), and humans (Caplan et al., 1993; Young, 1999a-c).

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of GEP or active fragments thereof binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions may further include an effective amount of the GEP or active fragments thereof/GEP or active fragments thereof antagonist or analog thereof, and one or more of the following active ingredients: an antibiotic, a steroid.

As used herein, "pg" means picogram, "ng" means nanogram, "ug" or "μg" mean microgram, "mg" means milligram, "ul" or "μl" mean microliter, "ml" means milliliter, "l" means liter.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMB9 and their derivatives, plasmids such as RP4; phage DNAS, e.g., the numerous derivatives of phage □, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage □, the control regions of fd coat protein, the promoter for 3-phosphoglycerate kinase or other glycolytic enzymes, the promoters of acid phosphatase (e.g., Pho5), the promoters of the yeast-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that GEP or active fragments thereof analogs may be prepared from nucleotide sequences of the protein complex/subunit derived within the scope of the present invention. Analogs, such as fragments, may be produced, for example, by pepsin digestion of GEP or active fragments thereof material. Other analogs, such as muteins, can be produced by standard site-directed mutagenesis of GEP or active fragments thereof coding sequences. Analogs exhibiting "GEP or active fragments thereof activity" such as fragments, granulins, small molecules, whether functioning as promoters or inhibitors, may be identified by known in vivo and/or in vitro assays.

As mentioned above, a DNA sequence encoding GEP or active fragments thereof can be prepared synthetically rather than cloned. The DNA sequence can be designed with the appropriate codons for the GEP or active fragments thereof amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature,* 292:756 (1981); Nambair et al., *Science,* 223:1299 (1984); Jay et al., *J. Biol. Chem.,* 259:6311 (1984).

Synthetic DNA sequences allow convenient construction of genes which will express GEP or active fragments thereof analogs or "muteins". Alternatively, DNA encoding muteins can be made by site-directed mutagenesis of native GEP or active fragments thereof genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science,* 244:182-188 (April 1989). This method may be used to create analogs with unnatural amino acids.

The present invention extends to the preparation of antisense oligonucleotides and ribozymes that may be used to interfere with the expression of the GEP or active fragments thereof at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into GEP-producing cells. Antisense methods have been used to inhibit the expression of many genes in vitro (Marcus-Sekura, 1988; Hambor et al., 1988).

The antisense or oligonucleotide may be modified to enhance nuclease resistance. Nucleic acids which contain at least one phosphorothioate modification are particularly preferred (Geary, R. S. et al (1997) Anticancer Drug Des 12:383-93; Henry, S. P. et al (1997) Anticancer Drug Des 12:395-408; Banerjee, D. (2001) Curr Opin Investig Drugs 2:574-80). Specific examples of some preferred oligonucleotides envisioned include those containing modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones. The amide backbones disclosed by De Mesmaeker et al. (1995) Acc. Chem. Res. 28:366-374) are also preferred. Also preferred are oligonucleotides having morpholino backbone structures (Summerton and Weller, U.S. Pat. No. 5,034,506). In other particular embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., Science, 1991, 254, 1497). Nucleic acids may also contain one or more substituted sugar moieties. Antisense or oligonucleotides may comprise one of the following at the 2' position: OH, SH, $SCH_3$, F, OCN, heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. Similar modifications may also be made at other positions on the oligonucleotide, particularly the 3' position of the sugar on the 3' terminal nucleotide and the 5' position of 5' terminal nucleotide.

Nucleic acids may also include, additionally or alternatively base modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-me pyrimidines, particularly 5-methylcytosine (5-me-C) (Sanghvi, Y. S., in Crooke, S. T. and Lebleu, B., eds., Antisense Research and Applications, CRC Press, Boca Raton, 1993, pp. 276-278), 5-hydroxymethylcytosine (HMC), glycosyl HMC and gentobiosyl HMC, as well as synthetic nucleobases, including but not limited to, 2-aminoadenine, 2-thiouracil, 2-thiothymine, 5-bromouracil, 5-hydroxymethyluracil, 8-azaguanine, 7-deazaguanine (Kornberg, A., DNA Replication, W.H. Freeman & Co., San Francisco, 1980, pp 75-77; Gebeyehu, G., et al., 1987, Nucl. Acids Res. 15:4513). A "universal" base known in the art, e.g., inosine, may be included. It is not necessary for all positions in a given nucleic acid or oligonucleotide to be uniformly modified, and more than one of the aforementioned modifications may be incorporated in a single oligonucleotide or even at a single nucleoside within an oligonucleotide.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, *Tetrahymena*-type and "hammerhead"-type. (Hasselhoff and Gerlach, 1988) *Tetrahymena*-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to *Tetrahymena*-type ribozymes for inactivating a specific mRNA species, and eighteen base recognition sequences are preferable to shorter recognition sequences.

The use of RNA interference strategies to inhibit the expression of GEP or active fragments thereof is further embodied in the invention. Thus, methods of RNA interference and small interfering RNA compositions are included in the methods and compositions of the present invention. RNA interference refers to the silencing of genes specifically by double stranded RNA (dsRNA) (Fine, A. et al (1998) Nature 391; 806-811). In one embodiment, short or small interfering RNA (siRNA) is utilized (Elbashir, S. M. et al (2001) Nature 411:494-498). In addition, long double stranded RNA hairpins may be employed (Tavemarakis, N. et al (2000) Nature Genet. 24:180-183; Chuang, C. F. and Meyerowitz, E. M. (2000) PNAS USA 97:4985-90; Smith, N A et al (2000) Nature 407:319-20).

The DNA sequences described herein may thus be used to prepare antisense molecules against, ribozymes and small interfering RNAs that cleave mRNAs or facilitate the degradation of mRNAs for GEP, active fragments of GEP including granulins and their ligands.

The present invention also relates to a variety of diagnostic applications, including methods for detecting the presence of stimuli such as the earlier referenced polypeptide ligands, by reference to their ability to elicit the activities which are mediated by the present GEP or active fragments thereof. As mentioned earlier, the GEP or active fragments thereof can be used to produce antibodies to itself by a variety of known techniques, and such antibodies could then be isolated and utilized as in tests for the presence of particular GEP or active fragments thereof activity in suspect target cells.

As described in detail above, antibody(ies) to the GEP or active fragments thereof can be produced and isolated by standard methods including the well known hybridoma techniques. For convenience, the antibody(ies) to the GEP or active fragments thereof will be referred to herein as $Ab_1$ and antibody(ies) raised in another species as $Ab_2$.

The presence of GEP or active fragments thereof in cells can be ascertained by the usual immunological procedures applicable to such determinations. A number of useful procedures are known. Three such procedures which are especially useful utilize either the GEP or active fragments thereof labeled with a detectable label, antibody Ab, labeled with a detectable label, or antibody $Ab_2$ labeled with a detectable label. The procedures may be summarized by the following equations wherein the asterisk indicates that the particle is labeled, and "GEP or active fragments thereof" stands for the GEP or active fragments thereof:

A. GEP or active fragments thereof*+$Ab_1$=GEP or active fragments thereof*$Ab_1$
B. GEP or active fragments thereof+Ab*=GEP or active fragments thereof$Ab_i$*
C. GEP or active fragments thereof+$Ab_1$+$Ab_2$*=GEP or active fragments thereof$Ab_1Ab_2$*

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Patent Nos. RE 31,006 and 4,016,043. Still other procedures are known such as the "double antibody," or "DASP" procedure.

In each instance, the GEP or active fragments thereof forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-GEP or active fragments thereof antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The GEP or active fragments thereof or its binding partner(s) can also be labeled with a radioactive element or with an enzyme. The radioactive label can be detected by any of the currently available counting procedures. The preferred isotope may be selected from 3H, 14C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the GEP or active fragments thereof may be radiolabeled and combined, for example, with antibodies or other inhibitors thereto, after which binding studies would be carried out. Solutions would then be prepared that contain various quantities of labeled and unlabeled uncombined GEP or active fragments thereof, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

An assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

In a further embodiment of this invention, commercial test kits suitable for use by a medical specialist may be prepared to determine the presence or absence of predetermined GEP or active fragments thereof activity or predetermined GEP or active fragments thereof activity capability in suspected target cells. In accordance with the testing techniques discussed above, one class of such kits will contain at least the labeled GEP or active fragments thereof or its binding partner, for instance an antibody specific thereto, and directions, of course, depending upon the method selected, e.g., "competitive," "sandwich," "DASD" and the like. The kits may also contain peripheral reagents such as buffers, stabilizers, etc.

Accordingly, a test kit may be prepared for the demonstration of the presence or capability of cells for predetermined GEP or active fragments thereof activity, comprising:
(a) a predetermined amount of at least one labeled immunochemically reactive component obtained by the direct or indirect attachment of the present GEP or active fragments thereof factor or a specific binding partner thereto, to a detectable label;
(b) other reagents; and
(c) directions for use of said kit.

More specifically, the diagnostic test kit may comprise:
(a) a known amount of the GEP or active fragments thereof as described above (or a binding partner) generally bound to a solid phase to form an immunosorbent, or in the alternative, bound to a suitable tag, or plural such end products, etc. (or their binding partners) one of each;
(b) if necessary, other reagents; and
(c) directions for use of said test kit.

In a further variation, the test kit may be prepared and used for the purposes stated above, which operates according to a predetermined protocol (e.g. "competitive," "sandwich," "double antibody," etc.), and comprises:
(a) a labeled component which has been obtained by coupling the GEP or active fragments thereof to a detectable label;
(b) one or more additional immunochemical reagents of which at least one reagent is a ligand or an immobilized ligand, which ligand is selected from the group consisting of:
 (i) a ligand capable of binding with the labeled component (a);
 (ii) a ligand capable of binding with a binding partner of the labeled component (a);
 (iii) a ligand capable of binding with at least one of the component(s) to be determined; and
 (iv) a ligand capable of binding with at least one of the binding partners of at least one of the component(s) to be determined; and
(c) directions for the performance of a protocol for the detection and/or determination of one or more components of an immunochemical reaction between the GEP or active fragments thereof and a specific binding partner thereto.

In accordance with the above, an assay system for screening potential drugs effective to modulate the activity of the GEP or active fragments thereof may be prepared. The GEP or active fragments thereof may be introduced into a test system, and the prospective drug may also be introduced into the resulting cell culture, and the culture thereafter examined to observe any changes in the GEP or active fragments thereof activity of the cells, due either to the addition of the prospective drug alone, or due to the effect of added quantities of the known GEP or active fragments thereof.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

COMP Associates with GEP and Potentiates GEP-Stimulated Chondrocyte Proliferation Although mutations in the human cartilage oligomeric matrix protein (COMP) have been linked to the development of pseudoachondroplasia and multiple epiphyseal dysplasia, the roles of both wildtype and mutant COMP in the skeletogenesis remain unknown. In an effort to define the biological role of COMP, a functional genetic screen based on the yeast two-hybrid system was performed. This led to the identification of Granulin-epithelin precursor (GEP), an autocrine growth factor, as a COMP-associated partner. COMP directly binds to GEP both in vitro and in vivo, as revealed by in vitro pulldown and co-immunoprecipitation assays. GEP selectively interacts with the EGF repeat domain but not with the other three functional domains of COMP. The Granulin A repeat unit of GEP is required and sufficient for association with COMP. COMP co-localizes with GEP predominantly in the pericellular matrix of transfected rat chondrosarcoma cell (RCS) and primary human chondrocytes. Staining of musculoskeletal tissues of day 19 mouse embryo with GEP specific antibody is restricted to chondrocytes and appears to be concentrated in areas where ossification will occur. Overexpression of GEP stimulates the proliferation of chondrocytes and this stimulation is enhanced by COMP. In addition, COMP appears to be required for the GEP-mediated chondrocyte proliferation, since stimulation of chondrocyte proliferation by GEP is dramatically inhibited by an anti-COMP antibody. These findings provide the first evidence slinking the association of COMP and GEP, a previously unrecognized growth factor GEP in cartilage, to chondrogenesis.

Cartilage oligomeric matrix protein (COMP) is a noncollagenous component of the extracellular matrix. It is expressed in cartilage, ligament, tendon, bone (osteoblasts only), and synovium (1-3). COMP is a 524 kDa pentameric, disulfide-bonded, multidomain glycoprotein composed of approximately equal subunits (GEP or active fragments thereof 110 kDa each) (4,5). Although COMP has been implicated in the regulation of chondrogenesis in a micromass culture of mesenchymal stem 10T1/2 cells and in limb development in vivo (6,7), its function remains largely unknown. COMP binds to chondrocytes in vitro and the RGD sequence in COMP and the integrin receptors $\alpha 5\beta 1$ and $\alpha V3$ on chondrocytes are believed to be involved in mediating this attachment(8).

COMP has been shown to be upregulated after traumatic knee injury(9) and has been implicated in the pathogenesis of rheumatoid arthritis and osteoarthritis (OA) (10-12). Monitoring of COMP levels in either joint fluid or serum can be used to assess the presence and progression of arthritis (13-18). Mutations in the human COMP gene have been linked to the development of pseudoachondroplasia and multiple epiphyseal dysplasia, autosomal-dominant forms of short-limb dwarfism characterized by short stature, N facies, epiphyseal abnormalities, and early-onset osteoarthritis (19-25).

During mouse development, COMP staining has been described in the pericellular matrix of maturing articular chondrocytes(25), and during rat development it has been associated mainly with the growth plate (3). These in vivo data suggested that COMP may play important roles in chondrogenesis and cartilage development. One of the aims of the present study, therefore, was to isolate the proteins that associate with COMP in order to elucidate its biological functions in skeletogenesis. A yeast two-hybrid screen using the EGF domain of COMP as bait led to the isolation of Granulin-epithelin precursor (GEP), as a COMP binding growth factor.

Granulin-epithelin precursor (GEP), also referred to as progranulin, proepithelin, PC-cell-derived growth factor (PCDGF), or acrogranin, is a 68.5-kDa secreted growth factor. It is heavily glycosylated and appears as an approximately 90-kDa protein on sodium dodecyl sulfate polyacrylamide gel electrophoresis. Structurally, it belongs to none of the well-established growth factor families. GEP is secreted in an intact form (26,27), or undergoes proteolysis leading to the release of its constituent peptides, the granulins(28-30). Individual granulins have an approximate molecular weight of 6 kDa, and are structurally defined by the presence of 12 cysteines arranged in a characteristic motif: X2-3CX5-6CX5CCX8CCX6CCX5CCX4CX5-6CC2 (SEQ ID NO: 2) (31). Comparison of the biosynthetic origin of granulin peptides in various mammals reveals that all are commonly derived from a precursor composed of one amino-terminal half (p) followed by seven (A-G) non-identical copies of the granulin motif (32).

GEP is abundantly expressed in rapidly cycling epithelial cells, in cells of the immune system and in neurons(30, 33-35). High levels of GEP expression are also found in several human cancers, and are believed to contribute to tumorigenesis in diverse cancers, including breast cancer, clear cell renal carcinoma, invasive ovarian carcinoma, glioblastoma, adipocytic teratoma, multiple myeloma (28,32,36-41). We have found elevated levels of GEP expression in osteosarcoma (data not shown). The role of GEP in the regulation of cellular proliferation has been well characterized using mouse embryo fibroblasts derived from mice with a targeted deletion of the insulin-like growth factor receptor (IGF-IR) gene ($R^-$ cells). These cells are unable to proliferate in response to IGF-I and other growth factors (EGF and PDGF) necessary to fully progress through the cell cycle(42). In contrast, GEP is the only known growth factor able to bypass the requirement for the IGF-IR, thus promoting growth of $R^-$cells(29,43). Increasing evidence has also implicated GEP in the regulation of differentiation, development and pathological processes. It has been isolated as a differentially-expressed gene from mesothelial differentiation (44), sexual differentiation of the brain(45), macrophage development (46) and synovium of rheumatoid arthritis and osteoarthritis (47). Remarkably, GEP was also shown to be a crucial mediator of wound response and tissue repair(38,48).

The aim of this study is to characterize the interaction between GEP and COMP and to investigate the biological significance of this interaction in regulating chondrocyte proliferation.

Experimental Procedures
Plasmid Constructs

Yeast expression vectors pDBleu and pPC86 (both Life Technologies, Gaithersburg, Md.) are fusion vectors for the linkage of proteins to the Gal4 DNA binding domain and to the VP 16 transactivation domain, respectively. Fragments encoding the four functional domains, i.e., the N-terminal (aa 20-83), EGF repeat domain (aa 84-261), type III repeat domain (aa 266-520), and C-terminal (aa 521-755; GenBank accession number AF257516) of mouse COMP were amplified by polymerase chain reaction (PCR) and cloned inframe into the SalI/NotI sites of pDBleu (pDB-COMP-NT, pDB-COMP—epidermal growth factor, pDB-COMP-type III, and pDB-COMP-CT) to serve as bait in the screening assay.

The bacterial expression vector pGEX-3x(Life Technologies) was used to produce recombinant glutathione S-transferase (GST) fusion proteins in *Escherichia coli*. The cDNA fragments encoding EGF repeat domain of mouse COMP (aa 84-261, Genbank accession number AF257516) was inserted inframe into the BamHI/EcoRI sites of pGEX-3x to generate the plasmids pGEX-EGF. The bacterial expression pBAD TOPO vector (Invitrogen, Carlsbad, Calif.) was used to produce His-tagged proteins in *E. coli*.

cDNA inserts encoding different fragments (TABLE 1) of GEP (Genbank accession number NM_017113.1) was subcloned into the pBAD TOPO vector per the manufacturer's instructions to generate the indicated plasmids.

TABLE 1

Fragments of Rat GEP Cloned into pBAD TOPO Vector

| Fragment | Plasmid |
|---|---|
| Granulin A (a.a. 278-333) (SEQ ID NO: 15) | pGEP (278-333) |
| Granulin C (a.a. 361-413) (SEQ ID NO: 16) | pGEP (361-413) |
| Granulin D (a.a. 438-492) (SEQ ID NO: 17) | pGEP (438-492) |
| Granulin E (a.a. 512-567) (SEQ ID NO: 18) | pGEP (512-567) |
| Granulin ACDE (a.a. 278-588) (SEQ ID NO: 19) | pGEP (278-588) |
| GEP (a.a. 1-588) rat (SEQ ID NO: 22) | pGEP (1-588) |

The mammalian expression pEGFP-GEP construct was kindly provided by Dr. Mathews at UMDNJ. The mammalian expression pDsRed1-N1 (BD Biosciences Clontech) was used to produce recombinant protein. cDNA fragment encoding mouse full length COMP was amplified by PCR and subcloned in-frame into the EcoRI/KpnI sites of pDsRed1-N1 to produce plasmid pDsRed1-N1-COMP, which express RED fusion proteins in mammalian cell line. All constructs were verified by nucleic acid sequencing; subsequent analysis was performed using BLAST software (available at ncbi.nlm.nih.gov/blast).

Generation of Stable Lines in RCS Cell

Rat chondrosarcoma cells (RCS cell) were cultured in tissue culture dishes in Dulbecco's modified Eagle's medium (DMEM) supplemented with 10% heat-inactivated fetal calf serum (FBS), and antibiotics. RCS cells were plated 1 day before transfection at a density of $1.5 \times 10^5$ cells/30-mm plate. Transfection was carried out using Lipofectamine reagent (Invitrogen) following the manufacturer's instructions. The plasmid pEGFP-GEP, pDsRed1-N1-COMP, and pEGFP-GEP plus pDsRed1-N1-COMP or the empty pEGFP vector were transfected into RCS cells to generate RCS-GEP, RCS—COMP, RCS-GEP plus COMP and RCS-control cell line. Two days after transfection, cells were split into 100-mm dishes at a density of $10^5$ cells/dish in 10 ml of Dulbecco's modified Eagle's medium containing G418 at 1,000 μg/ml. After 14 days in selective medium (medium changed every 3 days), cells were expanded in Dulbecco's modified Eagle's medium containing 500 μg/ml of G418.

Expression and Purification of GST and His-tagged Proteins

For expression of GST fusion proteins, the appropriate plasmid pGEX-EGF was transformed into E. coli DH5α (Life Technologies). Fusion proteins were affinity-purified on glutathione-agarose beads, as described previously (49). His-GrnA, His-GmC, His-GrnD, His-GrnE, His-GmACDE and His-GEP were purified by affinity chromatography using a HiTrap chelating column (Amersham Pharmacia Biotech, Uppsala, Sweden). Briefly, bacteria lysates supplemented with 20 mM HEPES (pH 7.5) and 0.5 M NaCl were applied to the HiTrap chelating column, the column was washed with HSB buffer (40 mM HEPES, pH 7.5, 1 M NaCl, and 0.05% Brij 35) containing 10 mM imidazole, and the His-GrnA, His-GmC, His-GrnD, His-GrnE and His-GrnACDE were eluted with HSB buffer containing 300 mM imidazole.

Yeast Two-hybrid (Y2H) Library Screen

Plasmid pDB-COMP-epidermal growth factor (see above) was used as bait to screen Y2H rat brain cDNA library (Life Technologies) according to a modified manufacturer's protocol. Briefly, bait plasmid was introduced into a yeast MAV203 strain that contained three reporter genes, HIS$^+$, URA$^+$, and Lac Z (Life Technologies), and transformants were selected on defined medium lacking leucine. The rat brain cDNA library in the vector pPC86 was then transformed into the resultant Leu$^+$ yeast strain and plated on medium lacking tryptophan, leucine, histidine, and uracil but containing 25 mM 3-amino-1,2,4-trizone that can specifically inhibit the activity of HIS3 gene product and block the basal concentration of HIS3 in yeast (SD-leu$^-$/trp$^-$/his$^-$/ura$^-$/3AT$^+$). After incubation for 7-10 days at 30° C., colonies were screened for β-galactosidase by a filter lift assay (24). Individual pPC86 recombinant plasmids which were identified in the initial screen were further verified for interaction with bait by repeating the Y2H assay.

Assay of Protein-protein Interactions Using the Y2H System

Three independent colonies were analyzed for interaction in yeast of two proteins, one of which was fused to the Gal4 DNA binding domain and the other to the VP16 transactivation domain. The procedures of Vojtek et al. (50) and Hollenberg et al. (51) were followed for I) growing and transforming the yeast strain MAV203 with the selected plasmids; and 2) β-galactosidase activity and growth phenotypes on growth phenotypes on selective SD-leu$^-$/trp$^-$/his$^-$/ura$^-$/3AT$^+$ plates.

In Vitro Binding Assay

For examination of the binding of COMP to GEP in vitro, Glutathione-Sepharose beads (500 preincubated with either purified GST (0.5 μg, serving as control) or GST-epithelial growth factor (EGF)-like domain of COMP and Ni-NTA Sepharose preincubated with either His or His-tagged GEP were incubated with purified His-tagged Grn-ACDE or COMP (purified from HEK293 cells stably transfected with an expression plasmid encoding full-length human COMP) respectively. Bound proteins were resolved by 12% SDS-PAGE and detected by Western blotting with anti-His antibodies and polyclonal rabbit anti-COMP antiserum.

In the case of the binding assay for dissecting the repeat unit of GEP required for interaction with COMP, Glutathione-Sepharose beads (50 μl) preincubated with either purified GST (0.5 μg, serving as control) or GST-EGF domain of COMP was incubated with purified His-tagged Grn-ACDE, GrnA, GrnC, GrnD, or GrnE respectively. Bound proteins were processed as described above.

Coimmunoprecipitation

Approximately 500 μg of cell extracts prepared from isolated human chondrocytes were incubated with anti-COMP (25 μg/ml) or control rabbit IgG (25 μg/ml) antibodies for 1 hr, followed by incubation with 30 μl of protein A-agarose (Life Technologies) at 4° C. overnight. After washing five times with immunoprecipitation buffer, bound proteins were released by boiling in 20 μl of 2×SDS loading buffer for 3 min (52). Released proteins were examined by western blotting with anti-GEP antibodies, and the signal was detected using the ECL chemiluminescent system (Amersham Pharmacia Biotech, Upsala, Sweden).

Co-localization Assays of COMP and GEP

Etopic expression of fluorescent GEP and COMP in living cells. To examine whether co-expressed GEP and COMP colocalize in the living cells, GFP (Green Fluorescent Protein)-linked GEP and RFP (Red Fluorescent Protein)-fused COMP were co-transfected into RCS chondrocytes and 48 hours later the culture was directly observed under a fluorescence microscope with appropriate optical filters. Microscopic images were captured using the Image Pro program (Media Cybernetics) and an Olympus microscope. Images were arranged using the Adobe Photoshop program.

(ii) Immunostaining for COMP and GEP in Primary Human Chondrocytes.

Cultures of isolated human chondrocytes were plated on glass coverslips coated with polylysine and grown in Dulbecco's modified Eagle's medium (DMEM) supplemented with 10% fetal bovine serum (FBS; GIBCO/BRL) under an atmosphere of 5% $CO_2$ at 37° C. After reaching 80% confluency, the cells were fixed with cold acetone-methanol (1:1) for 20 min and airdried. After rehydration in phosphate-buffered saline (PBS) and blocking with 20% goat serum in PBS for 30 min, the cells were incubated with primary antibodies (i.e., mouse monoclonal anti-COMP antibodies (diluted 1:50) and polyclonal goat anti-GEP antibodies (Santa Cruz; diluted 1:50) at room temperature for 1 h. After being washed with PBS, the coverslips were incubated with secondary antibodies secondary antibodies (i.e., goat anti-mouse IgG conjugated with rhodamine (Santa Cruz; diluted 1:100) and chick anti-goat IgG conjugated with FITC (Santa Cruz; diluted 1:400) for 50 min. The specimens were observed and the images were processed as described above.

Immunohistochemistry

4 μm thick formalin fixed paraffin sections of 19 day-old embroyonic murine limbs were immunostained for GEP. The sections were pretreated with chondroitinase (Sigma) for 30 mins at 37° C. followed by protein block (Dako Serum-Free Protein Block) for 10 minutes at room temperature to reduce non-specific staining. Polyclonal goat anti-human GEP (Santa Cruz) was diluted at 1:200 and incubated overnight at 4° C. Binding of primary antibodies was detected using biotinylated anti-goat secondary antibody (Jackson Labs) diluted at 1:800 and incubated for 30 minutes at 37° C. followed by alkaline-phosphatase (Vector) at 37° C. for 30 min and developed with Vector Red (Vector) for 2 min at room temperature. Sections were counterstained with Mayer's Hematoxylin (Dako). The primary antibody was substituted with Negative Control SuperSensitive Goat Serum (BioGenex) for the negative control section. In the case of the assay for examining the COMP expression, the same tissue was used and the same protocol was followed except the anti-GEP was replaced by anti-COMP antibody and the sections were not pretreated with chondroitinase.

Assays for Chondrocyte Proliferation $1.0 \times 10^5$ of stable transfected RCS-control (GFP vector, serve as control), RCS—COMP, RCS-GEP, RCS—COMP plus GEP cells were cultured in 6-well dishes, and the viable cells were counted every day until day 5. Each group was repeated three times. In the case of the antibody-blocking experiment, $6.0 \times 10^4$ control and RCS cells transfected with a plasmid encoding GEP were cultured in 24-well plates in the presence of 0.5 μM either control or anti-COMP antibodies and the cell proliferation was assayed as above.

Results

Isolation of GEP as a COMP Binding Partner

To better understand the biological functions of COMP, we performed a Y2H screen. Briefly, we linked the four functional domains of COMP—the N-terminal pentamerizing domain (a.a. 20-83), the EGF-like domain (a.a. 84-261), type 3 repeats (a.a. 266-520), and the C-terminal (a.a. 521-755)—to the Gal4 DNA-binding domain (GAL4 DBD) in the plasmid pDBleu. We used the respective constructs as bait to screen a library of rat brain cDNA expressed as fusion proteins to the VP16 acidic activation domain (VP16AD) in the vector pPC86.

A Y2H rat cDNA library was screened with the construct encoding the EGF-like repeats of COMP. We screened approximately 2.5 million clones and identified 21 that activated the three reporter genes. Further tests involved the retransformation of yeast with the purified target plasmids and bait. Only 12 of the original 21 yeast clones expressed hybrid proteins that still interacted with the EGF-like domain bait (not shown). Two of the positive clones encoded two N-terminal truncated mutants (a.a. 228-588; a.a.334-588) of a secreted growth factor GEP (Accession #NM_017113.1).

Confirmation of Interaction Between COMP and GEP in Yeast The Y2H assay was repeated to verify the interaction between the EGF-like domain of COMP and the C-terminal of GEP (a.a. 228-588). The plasmid encoding the EGF-like domain of COMP linked to Ga14 DBD (above the line in FIG. 2) and the plasmid encoding C-terminal of GEP fused to the VP16AD (below the line in FIG. 2) were used to cotransform the yeast. Like the c-Jun/c-Fos pair, which is known to interact and used as a positive control, our assays indicated that COMP interacts with GEP in yeast, based on the activation of the LacZ reporter gene (left panel) and growth phenotypes on SD-leu⁻/trp⁻/his⁻/ura⁻/3AT⁺ plates (right panel).

COMP Directly Binds to GEP

To verify the interaction between COMP and GEP that was first identified in yeast, a GST pulldown assay was performed (FIG. 3A) to test whether the EGF-like domain of COMP binds to the C-terminal of GEP (a.a.228-588, Gm-ACDE) in vitro. GST did not pull down Grn-ACDE protein (lane 2), whereas GST-EGF efficiently pulled down purified recombinant His-tagged Gm-ACDE protein (lane 1), indicating binding of COMP to GEP in vitro. An opposite pulldown assay in which His-tagged GEP was conjugated to the beads was also performed. As shown in FIG. 3B, His-GEP (lane 1), but not His alone (lane 2), clearly retained purified COMP. Since only purified proteins were used in these assays, the interaction between COMP and GEP is interpreted to be direct.

Binding of COMP to GEP in Chondrocytes

The in vivo interaction between COMP and GEP was verified using a coimmunoprecipitation (CO-IP) assay—in order to determine whether these two proteins are bound in native human chondrocytes. The polyclonal antiserum against COMP was generated using intact purified hCOMP as an antigen (3,10,53). For the CO-IP assays, the cell extracts were incubated with either anti-COMP antiserum (FIG. 3C, lane 2) or control IgG (FIG. 3C, lane 3), and the immunoprecipitated complexes were subjected to a reducing SDS-PAGE and detected with anti-GEP antibodies (Polyclonal anti-acrogranulin, Santa Cruz Biotechnology). A specific GEP band was present in the immunoprecipitated complexes brought down by anti-COMP (lane 2), but not control IgG lane 3) antibodies, demonstrating that GEP specifically binds to the COMP in vivo.

Selective Association of GEP with the EGF-like Domain of COMP

Figure 4:
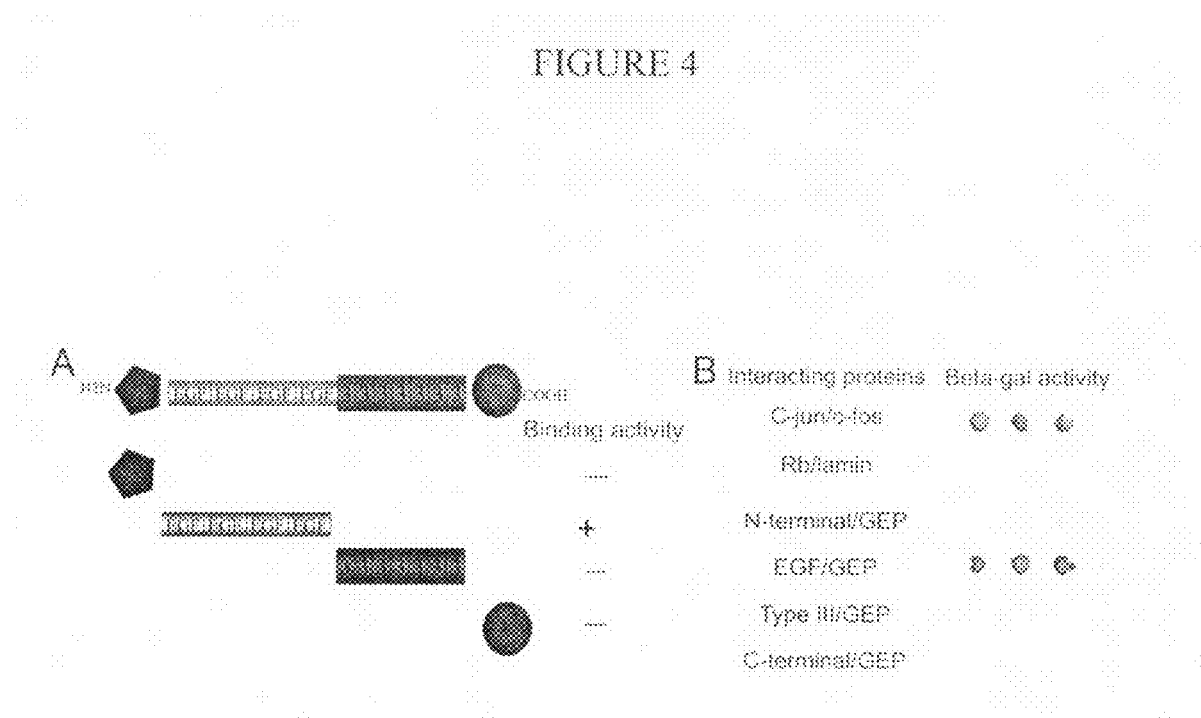
FIG. 4A-4B depicts that GEP selectively binds to the EGF-like domain of COMP. (A) Schematic structure of COMP constructs used to map those domains (N-terminal, EGF-like, type III, and C-terminal) that bind to GEP. Presence or absence of binding between COMP domains and GEP is indicated a "+" or "−", respectively. (B) β-Galactosidase activity was used to test interaction between the GEP and 1 of 4 domains of COMP. Three independent yeast transformants for each pair of plasmids were transferred onto a nitrocellulose membrane, and β-galactosidase activity was determined. The known interaction between c-Jun and c-Fos was used as a positive control, and the lack of interaction between Rb and lamin served as a negative control.

After GEP was identified as a COMP-binding protein using the Y2H screen, we sought to establish whether, in addition to EGF domain, other domains of COMP associate with GEP. A filter-based β-galactosidase assay was used to determine whether coexpression of the various domains of COMP/Gal4 DBD and GEP/VP16AD fusion proteins activate the reporter LacZ gene. As shown in FIG. 4, GEP selectively interacts with only the EGF-like domain of COMP.

Fragment GrnA of GEP is Required and Sufficient for Interaction with COMP

Since the C-terminal region of GEP (a.a. 228-518) was isolated as a COMP-binding protein in a Y2H screen followed by a confirmatory in vitro pull-down assay, we generated various constructs that expressed various His-tagged GEP C-terminal repeat unit fusion proteins in *E. coli.* to narrow-down the binding domain and to dissect the COMP-binding repeat unit in GEP. Results from in vitro pulldown assays (FIG. 5B) of all these mutants are summarized in FIG. 5A. The unit C (GrnC), the unit D (GrnD), and the unit E (GrnE) failed to bind COMP; however, the unit A (GrnA) did bind to COMP. Our conclusion is that granulin A unit of GEP is required and sufficient for its interaction with COMP.

COMP and GEP Co-localized in the Pericellular Matrix of Chondrocytes

Figure 6:
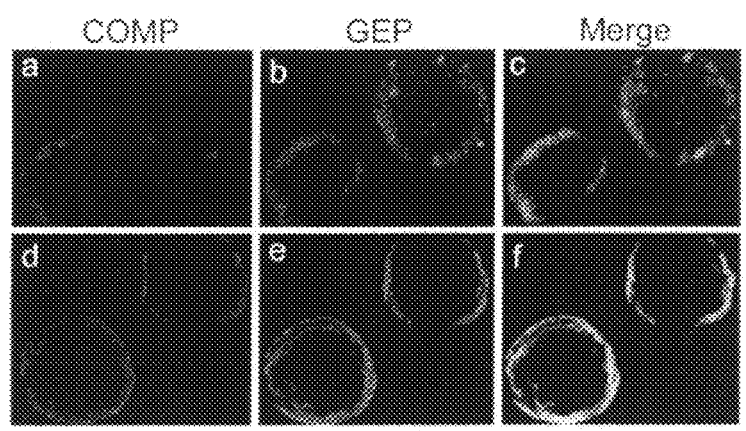
FIG. 6A-6F. COMP and GEP co-localizes in the cell surface of chondrocytes. The top row (Panel A, B and C) shows the pericellular matrix expression of COMP and GEP in the transfected RCS cells with plasmids encoding RFP-linked COMP and GFP-fused GEP) and the bottom row (Panel D, E and F) shows that pericellular matrix staining of COMP and GEP with anti-COMP and anti-GEP antibodies in the isolated human chondrocytes, revealing colocalization of COMP and GEP in specific punctate areas on the cell surface.

Next, we examined the subcellular localization of COMP and GEP and to determine whether these two proteins overlap in the same cell. We first transfected RCS cells with plasmids encoding GFP-linked GEP and RED-fused COMP. As revealed in FIG. 6 (Upper Panels A, B and C), in the living chondrocytes, GEP is clearly expressed and overlaps with COMP, an extracellular matrix protein of chondrocytes. The co-localization between COMP and GEP was further verified with immunostaining for COMP and GEP in primary human chondrocytes. As shown in FIG. 6 (Lower Panels D, E and F), COMP also co-localizes with GEP predominantly in the pericellular matrix of isolated adult human chondrocytes. These findings are in agreement with the physical interactions detected in the yeast two-hybrid and confirmed by pull-down and co-immunoprecipitation assays, and suggests that in chondrocytes, the membrane binding of GEP may be mediated, at least in part, by the COMP protein.

COMP and GEP Co-localize in the Chondrocytes of the Growth Plate In Vivo

We next examined the in vivo expressions of COMP and GEP and aimed to determine whether these two proteins also show overlapping expression patterns in vivo using immunohistochemistry assays on the 19 day-old embroyonic murine limbs. In line with previously findings on COMP expression in vivo, COMP was expressed in both chondrocytes and also osteoblasts (FIGS. 7C and 7D). Expression of GEP, however, was localized exclusively to the lower proliferative and upper hypertrophic zones of the growth plate chondrocytes, and was absent in osteocytes, osteoblasts, periosteum and perichondrium (FIGS. 7A and 7B). Expression of GEP in musculoskeletal tissues appears to be restricted to chondrocytes and is concentrated in areas where ossification will occur (FIGS. 7A and 7B). Although COMP is also expressed in the chondrocytes of growth plate, it demonstrates a broader expression pattern. Although GEP functions primarily as a secreted growth factor, has also been found to be localized intracellularly and to directly modulate intracellular activities (35, 54-56). Here GEP was also revealed to have intracellular localization in the growth plate chondrocytes of developing cartilage (FIG. 7B).

COMP Regulates the Stimulation of Chondrosarcoma Cell Proliferation by GEP

Our findings that GEP associates with COMP and that these two proteins colocalize in the chondrocytes, together with the reports that GEP is a potent stimulator of cell proliferation (28,29,32,36-41,43), prompted us to investigate whether GEP stimulates chondrocyte proliferation and, if so, whether COMP regulates this GEP-mediated chondrogenic process. Our findings with several stable lines revealed that both are true. Briefly, RCS chondrocytes were transfected with different constructs encoding COMP, GEP or vector only and selected with G418; the resultant stable transfectants were used for a cell proliferation assay in serum-containing conditions (FIG. 8A). Overexpression of COMP alone produced negligible effects on cell growth, whereas overexpression of GEP resulted in an increase in cell proliferation of 43% by day 3, and robust stimulation was observed by day 4 (1.8-fold) and day 5 (3.5-fold). Intriguingly this GEP-mediated stimulation was further enhanced by coexpression of COMP. The enhancement was observed as early as day 2 (2.3-fold) and continued through day 5 (2.1-fold increase by day 3, 1.7-fold increase by day 4 and 1.5-fold increase by day 5).

We next examined whether endogenous COMP in chondrocytes is required for GEP-mediated stimulation of cell growth by performing an antibody blocking assay. As shown in FIG. 8B, addition of anti-COMP antibody, but not a control antibody, dramatically inhibited GEP-mediated stimulation of chondrocyte proliferation, clearly indicating that natively expressed COMP is needed for the action of GEP in stimulating cell proliferation.

Discussion

Yeast two-hybrid screening has proven to be an effective tool in identifying protein interaction(57-59). To identify protein interaction partners of COMP, an extracellular matrix protein that has been implicated in the regulation of chondrogenesis and cartilage development(3,6,53), we screened the yeast expression cDNA library using the EGF repeat domain of COMP as bait and identified the granulin/epithelin precursor (GEP), a growth factor that has not been previously described in cartilage, as a direct binding protein of COMP.

Figure 5:
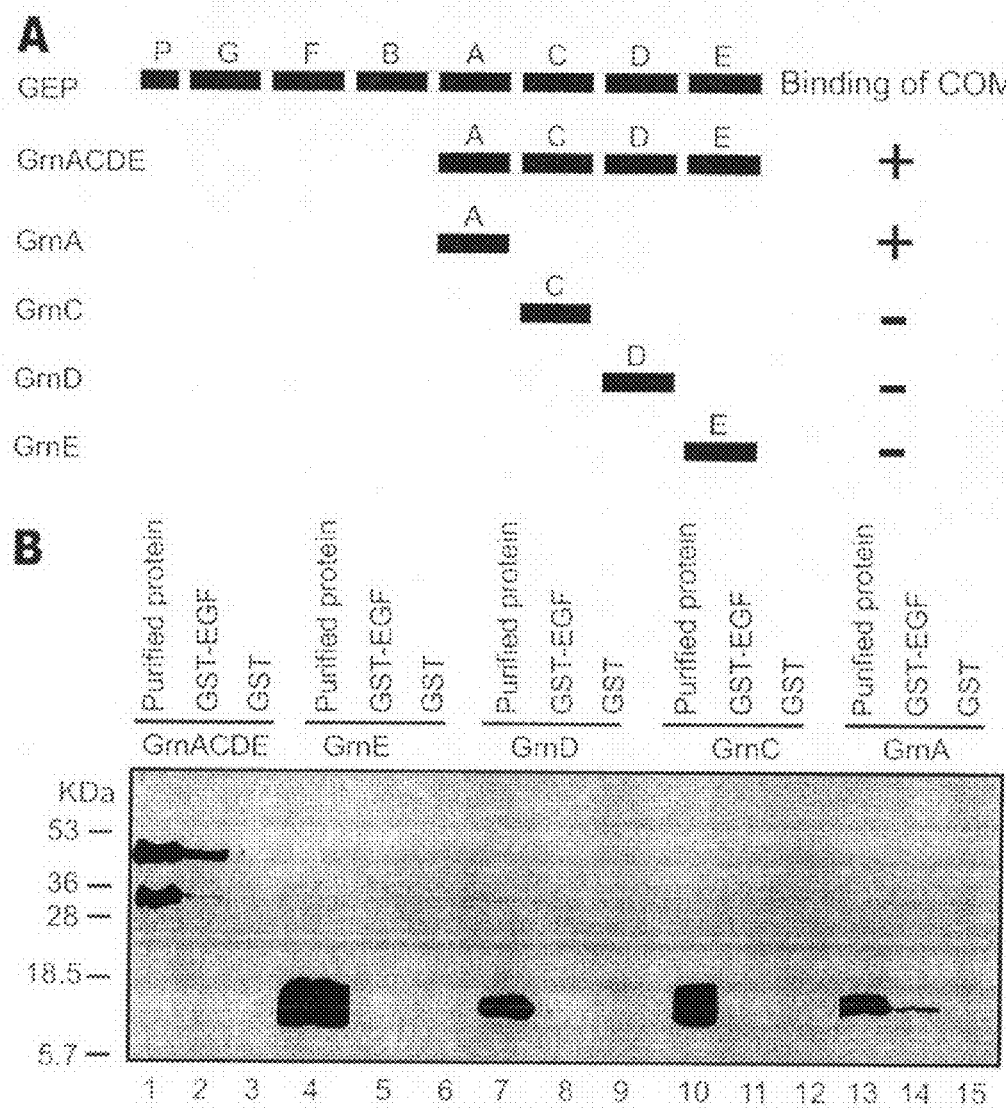
FIG. 5A-5B. Granulin A (GrnA) unit of GEP is required and sufficient for interaction with COMP. (A) Schematic diagram of GEP constructs used to map those of its repeat units that bind to COMP. GEP consists of seven (A-G) and a half (p) tandem repeats of a twelve cysteine motif. Closed boxes represent the granulin repeats; open boxes represent the intervening spacer regions; and the hatched box represents the signal sequence. Interactions between COMP and GEP units are summarized and indicated by "+" or "−." (B) In vitro GST pulldown assay was used to test interaction between purified His-tagged GEP units and COMP. Purified proteins and GST serve as positive and negative control, respectively.

GEP itself is a secreted growth factor with high molecular weight that is involved in various biological and pathological processes, including mesothelial differentiation(44), sexual differentiation of the brain(45), macrophage development (46), rheumatoid arthritis and osteoarthritis (47) and wound response and tissue repair(38,48). In some cases, GEP may be processed into small 6-kDa peptides, which may be stored in vesicles in the neutrophil. At present, only granulin A/epithelin 1 and granulin B/epithelin 2 have been shown to have biological activities. The actions of the other granulins (GrnC, GrnD, GrnE, GrnF or GrnG) are unknown (32). Granulin A/epithelin 1 stimulates the proliferation of murine keratinocytes in culture; Granulin B/epithelin 2 has no reported proliferative effects but, at an approximately ten-fold molar excess, it antagonizes the mitogenic action of Granulin A/epithelin 1 (60). Our in vitro binding assay showed that the Granulin A (GrnA) unit of GEP is required and sufficient for interaction with COMP, suggesting that COMP might also affect the activity of granulin A under some conditions (FIG. 5).

Figure 1:
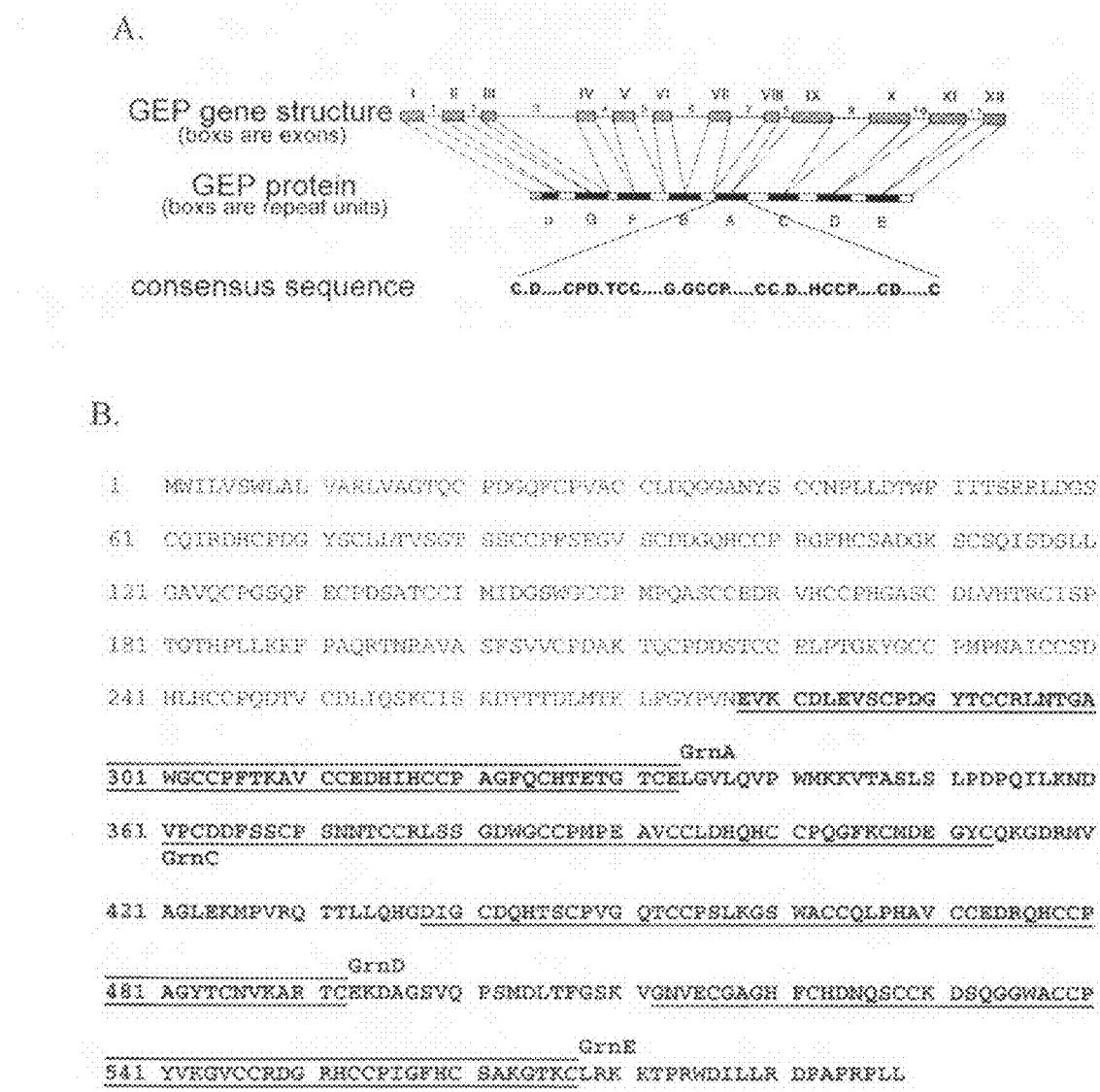
FIG. 1A-B depicts the structure and sequence of the GEP gene and its protein products. (A) depicts the structure of the GEP gene. Roman numerals set out individual exons. For the unit consensus sequence C represents cysteine, D aspartic acid, P proline, T threonine, G glycine, H histidine; dots in the consensus sequence depict any amino acids. (B) provides the amino acid sequence of rat GEP (SEQ ID NO:22) and the granulin fragments of rat GEP cloned into pBAD TOPO vector. GrnA (SEQ ID NO: 15), GrnC (SEQ ID NO: 16), GrnD (SEQ IDNO: 17) and GrnE (SEQ ID NO: 18) are underlined and indicated at each unit; fragment ACDE (SEQ ID NO: 19) is in boldface.
Figure 2:
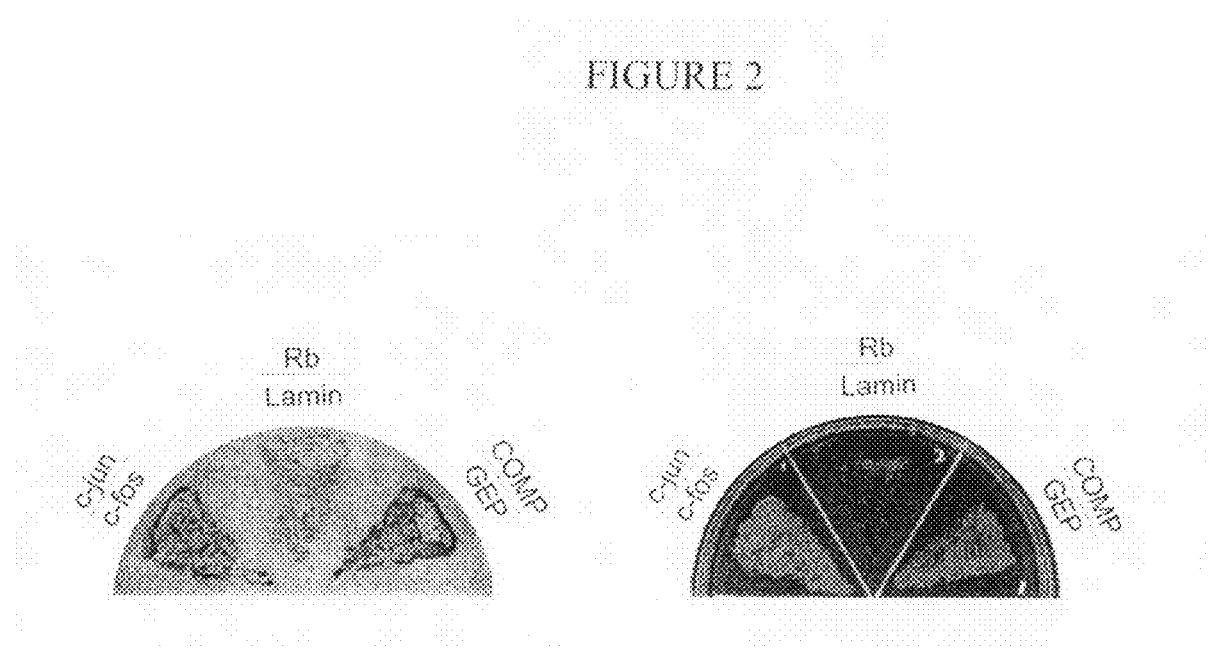
FIG. 2 depicts binding of COMP to GEP in Yeast. Yeast two-hybrid assay to test the interaction of proteins fused to the VP16 AD and proteins fused to the Gal4 DBD. Each pair of plasmids, as indicated, encoding proteins fused to VP 16 (below the line) in the vector pPC86 (i.e., pPC86-d-jun, pPC86-GEP, and pPC86—Rb) and those encoding proteins fused to Gal4 (above the line) in the vector pDBleu (i.e., pDB-c-fos, pDB-COMP, and pDB-lamin) were cotransfected into yeast strain MAV203. Yeast transformants were selected on SD-leu⁻/trp⁻ plates and tested for β-galactosidase activity (left panel) for growth inhibition on plates containing 5-fluoroorotic acid (SD-leu⁻/trp⁻/5FOA⁺) (right panel). The known interaction between c-jun and c-fos was used as a positive control, whereas the lack of interaction between Rb and lamin was used as a negative control.
Figure 3:
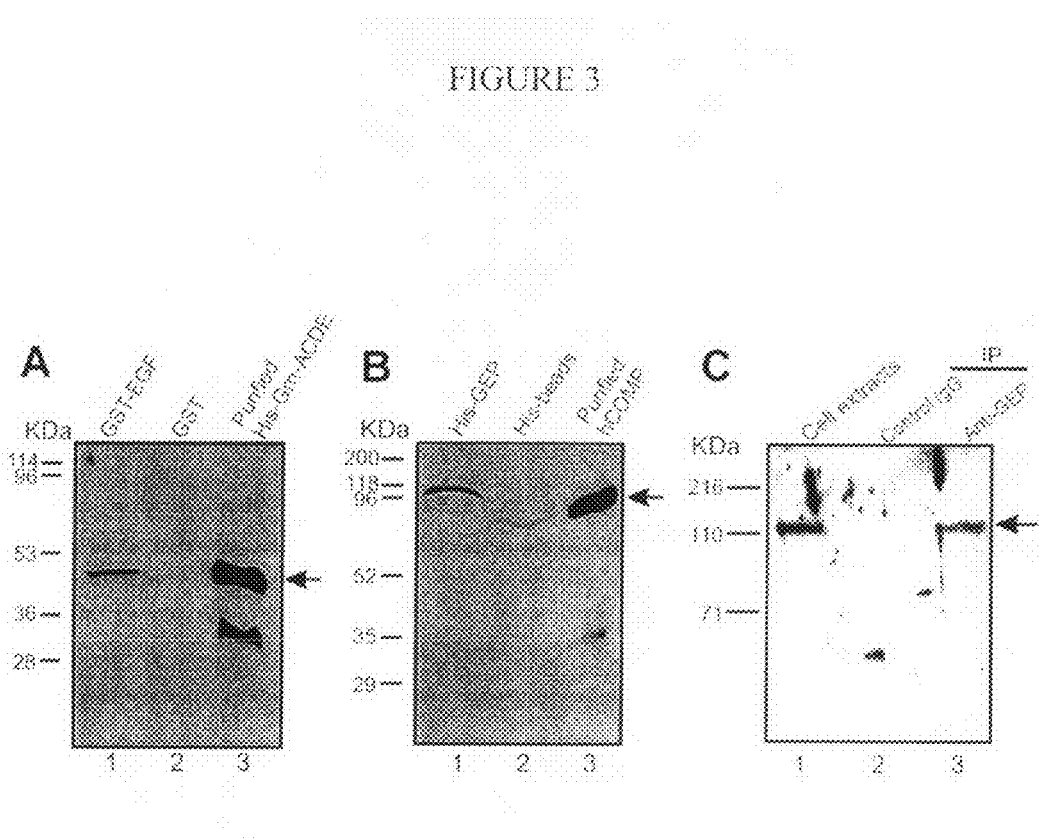
FIG. 3A-3C depicts that COMP binds to GEP. (A, B) COMP directly associates with GEP in vitro. GST pulldown assay (panel A). Purified GST (lane 2) or GST-EGF fusion protein (lane 1) immobilized on glutathine-Sepharose beads were incubated with purified His-Grn-ACDE. Proteins trapped by EGF domain of COMP fused to GST were examined by immunoblotting with anti-GEP antibodies. Purified His-Grn-ACDE (lane 3) was used as a positive control. H is pulldown assay (panel B) Purified His (lane 2) or His-GEP fusion protein (lane 1) immobilized on His beads were incubated with purified hCOMP. Proteins trapped were examined by immunoblotting with anti-COMP antibodies. Purified COMP (lane 3) was used as a positive control. (C)COMP interacts with GEP in vivo. Co-IP assay is shown. Cell extracts prepared from human chondrocytes were incubated with control IgG (lane 2) or anti-GEP (lane 3) antibodies followed by protein A agarose. The immuno-precipitated protein complex and cell extracts (lane 1, a positive control) were examined by immunoblotting with anti-COMP antibodies.
Figure 8:
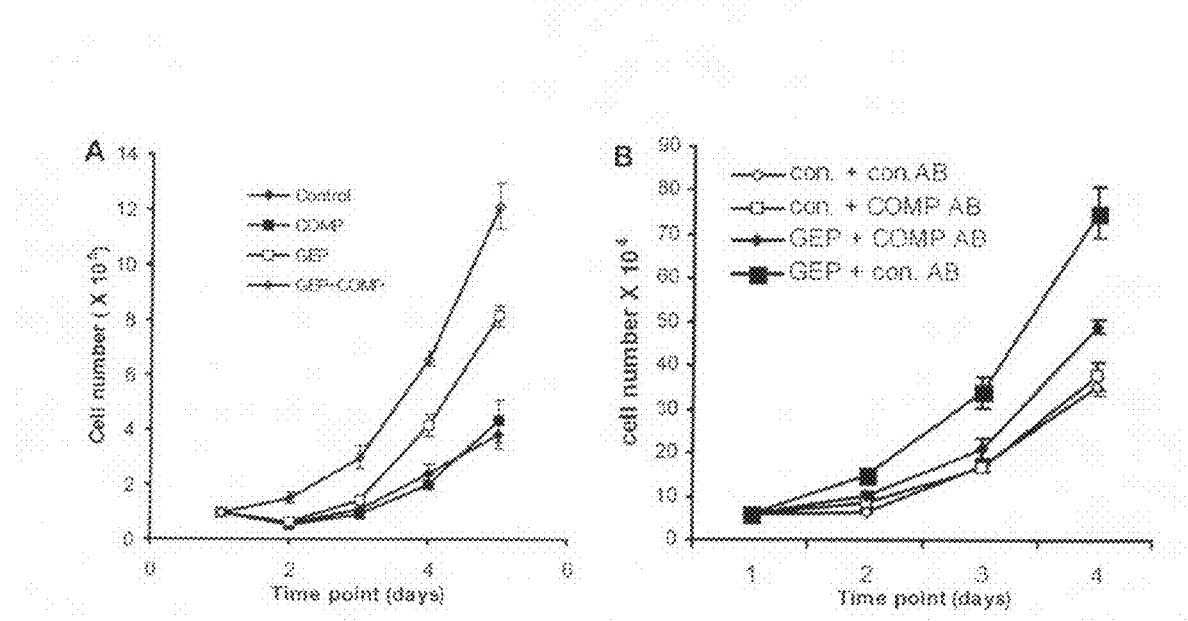
FIG. 8A-8B. COMP regulates the GEP-stimulated chondrocyte proliferation. (A) COMP enhances GEP-stimulated chondrocyte proliferation. Stable cell lines, as indicated, were cultured in 6-well dishes, and the viable cells were counted every day until day 5. Each group was repeated three times. (B) Endogenous COMP is required for the GEP-mediated stimulation on chondrocyte growth. Either a control (con. AB) or an anti-COMP(COMP AB) antibody was added to the cultures of control (con.) and RCS transfected with a GEP expression plasmid (GEP) and the cell proliferation was assayed as in (A).

GEP is a multi-repeat glycoprotein which has the potential to interact with other ECM proteins or cell surface receptors. It is conceivable that important biological functions of GEP are mediated by protein-protein interactions between the functional domains of GEP and its binding proteins. Several GEP-associated partners have been reported and have been found to affect GEP action in various processes. One example of this is the secretory leukocyte protease inibitor (SLPI). Elastase digests GEP exclusively in the interepithelin linkers resulting in the generation of granulin peptides, suggesting that this protease may be an important component of a GEP convertase. SLPI blocks this proteolysis either by directly binding to elastase or by sequestering epithelin peptides from the enzyme(48). It was found that GEP can modulate transcription activities by interacting with human cyclin T1, a component of positive transcription elongation factor b (P-TEFb)(55) and Tat-P-TEFb(54). GEP was also found to interact with perlecan, a heparan sulfate proteoglycan. The perlecan-GEP interaction was suggested to modulate tumor growth (37). Our global screen led to the isolation of GEP as a novel binding growth factor of COMP, a noncollagenous component of the cartilage matrix. The interaction between these two molecules appears to regulate chondrocyte proliferation (FIGS. 2, 3 and 8).

COMP has been reported to interact with multiple protein partners, and these interactions are important for its physiologic functions and cytoplasmic processing and transport. COMP appears to mediate chondrocyte attachment via an integrin receptor (1,8), and several reports suggest that COMP may function to stabilize the articular cartilage extracellular matrix by specific cation-dependent interactions with matrix components, including collagen types II and IX, fibronectin, aggrecan, and matrilin-1, -3, and -4 (16, 61-64). COMP has also been shown to associate with several chaperone proteins, including BiP, calreticulin, protein disulfide, ERp72, Grp94, HSP47, and calnexin, and it has been proposed that these associations facilitate the processing and transport of wild-type COMP in normal chondrocytes and in the retention of mutant COMP in pseudoachondroplasia chondrocytes (65-67). In addition to the interactions between COMP and its protein partners, the five-stranded N-terminal domain of COMP forms a complex with vitamin D-3, illustrating that COMP has a storage function for hydrophobic compounds, including prominent cell-signaling molecules (68). Very recently, we reported that ADAMTS-7 and ADAMTS-12, two members of the ADAMTS (a disintegrin and metalloprotease with thromospondin motifs) that share the similar domain structure and organization, bind to the same domain of COMP that GEP does and degrade COMP in vitro(59,69). The levels of ADAMTS-7 and ADAMTS-12 are significantly up-regulated in the cartilage and synovium of patients with arthritic diseases(59,69). It remains to be determined whether GEP competes with ADAMTS-7 or ADAMTS-12 for binding to COMP and thus inhibits their COMP-degrading activities. It also would be worthwhile to determine whether and how GEP, ADAMTS-7, ADAMTS-12 and COMP form a protein-protein interaction network in the regulation of COMP degradation and chondrogenesis.

Figure 7:
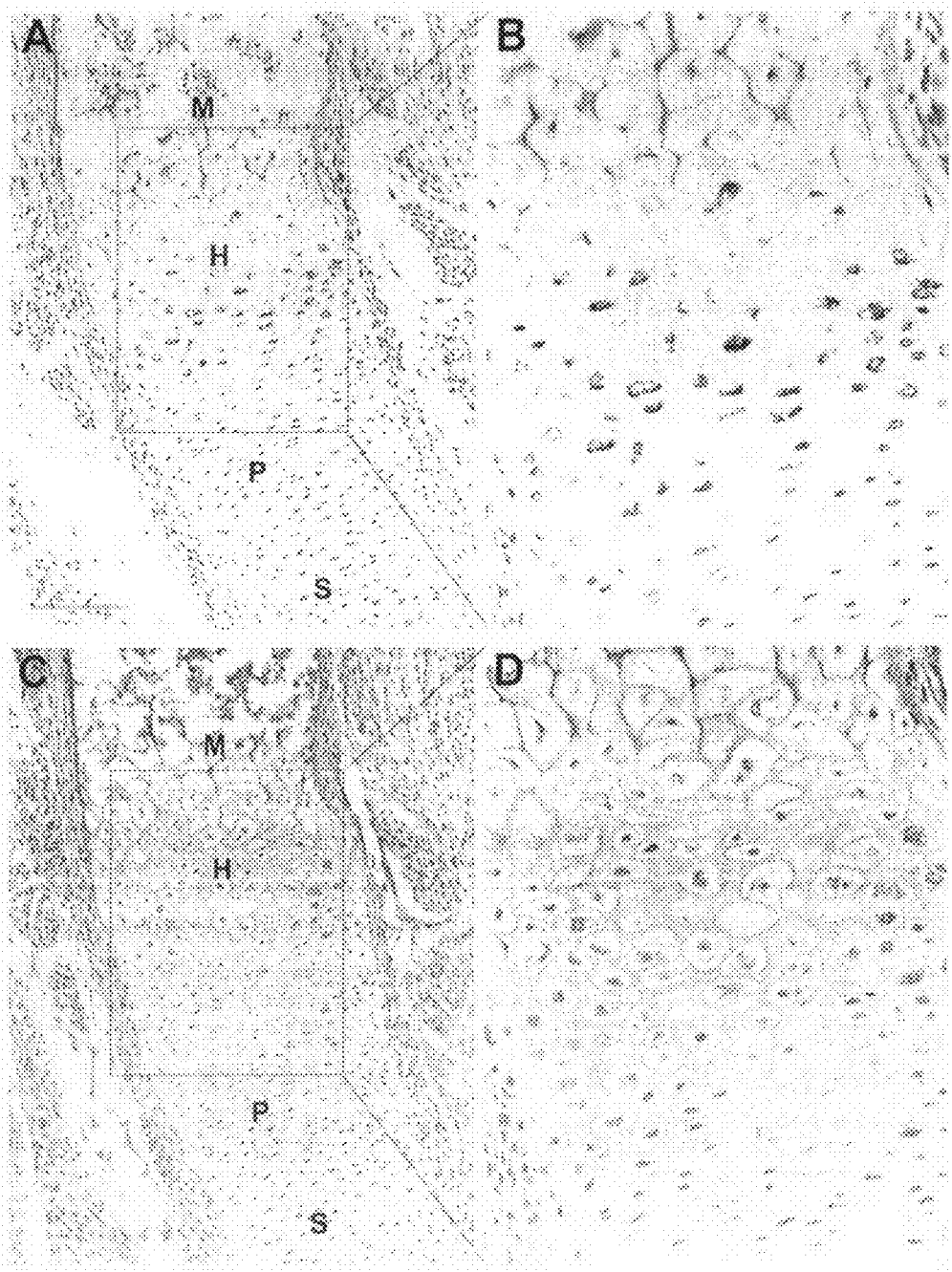
FIG. 7A-7D provides immunohistochemistry of COMP and GEP in the section of long bone from a 19-day-old mouse embryo. (A) Low-power microphotograph of section stained with anti-GEP polyclonal antibody (red) and counter stained with Mayer's hematoxylin (blue); immunostaining for GEP demonstrating localization of strongly immunopositive chondrocytes in the lower proliferative/upper hypertrophic zones of the growth plate. (B) High-power microphotograph of section in A. (C) Low-power microphotograph of section stained with anti-COMP polyclonal antibody (red) and counter stained with Mayer's hematoxylin (blue); immunostaining reveals positive staining in chondrocytes. (D) High-power microphotograph of section in C. Key: S, resting chondrocytes; P, proliferating chondrocytes; H, hypertrophic chondrocytes; M, bone metaphysis. Bar=100 μm.

COMP and GEP co-localize in the extracellular matrix of both transfected RCS cells and primary human chondrocytes (FIGS. 6A and 6B), as well as in growth plate chondrocytes in the day 19 mouse embryo (FIG. 7). These results suggest an in vivo association between COMP and GEP. Overexpression of COMP alone showed negligible effect on cell growth, whereas overexpression of GEP significantly stimulated chondrocyte proliferation; in addition, the GEP-mediated stimulation was further enhanced by coexpression of COMP (FIG. 8A). Intriguingly, although blocking COMP activity using antibodies directed against this molecule significantly slowed down the GEP-stimulated cell growth, stimulation of proliferation by GEP was not totally abolished (FIG. 8B). This finding suggests that other GEP-associated extracellular matrix molecules, including perlecan, which has been shown to interact with GEP (37), may be also involved in the regulation of GEP-mediated chondrocyte proliferation. Although the molecular mechanisms underlying the role of COMP/GEP interaction in the modulation of chondrocyte proliferation remain unclear, COMP may act as the co-factor of the GEP cell surface receptor(s) and may present GEP to its receptor followed by the activations of GEP-mediated signal transduction and gene regulation pathways.

Identification of GEP, a previously undescribed growth factor in cartilage, as a COMP-binding protein and subsequent characterization of this novel association as well as the functional assays showing that the stimulation of chondrocyte proliferation by GEP growth factor is mediated by COMP extend our understanding of the actions of growth factors in cartilage biology and also provide us a potential target for developing and optimizing the therapeutic application in cartilage repair and arthritic disorders.

References
1. DiCesare, P., Hauser, N., Lehman, D., Pasumarti, S., and Paulsson, M. (1994b) *FEBS Lett* 354(2), 237-240
2. DiCesare, P. E., Carlson, C. S., Stollerman, E. S., Chen, F. S., Leslie, M., and Perris, R. (1997) *FEBS Lett* 412(1), 249-252
3. Di Cesare, P. E., Fang, C., Leslie, M. P., Tulli, H., Perris, R., and Carlson, C. S. (2000) *J Orthop Res* 18(5), 713-720.
4. Morgelin, M., Engel, J., Heinegard, D., and Paulsson, M. (1992) *J Biol Chem* 267(20), 14275-14284.
5. Hedbom, E., Antonsson, P., Hjerpe, A., Aeschlimann, D., Paulsson, M., Rosa-Pimentel, E., Sommarin, Y., Wendel, M., Oldberg, A., and Heinegard, D. (1992) *J Biol Chem* 267(9), 6132-6136.
6. Kipnes, J., Carlberg, A. L., Loredo, G. A., Lawler, J., Tuan, R. S., and Hall, D. J. (2003) *Osteoarthritis Cartilage* 11(6), 442-454
7. Koelling, S., Clauditz, T. S., Kaste, M., and Miosge, N. (2006) *Arthritis Res Ther* 8(3), R56
8. Chen, F. H., Thomas, A. O., Hecht, J. T., Goldring, M. B., and Lawler, J. (2005) *J Biol Chem* 280(38), 32655-32661
9. Kuhne, S. A., Neidhart, M., Everson, M. P., Hantzschel, H., Fine, P. R., Gay, S., Hauselmann, H. J., and Gay, R. E. (1998) *Rheumatol Int* 18, 21-25
10. Di Cesare, P. E., Carlson, C. S., Stolerman, E. S., Hauser, N., Tulli, H., H, A.-T., and Paulsson, M. (1996) *J Orthop Res* 14, 946-955
11. Neidhart, M., Hauser, N., Paulsson, M., DiCesare, P. E., Michel, B. A., and Hauselmann, H. J. (1997) *Br J Rheumatol* 36(11), 1151-1160.
12. Saxne, T., and Heinegard, D. (1992) *Br J Rheumatol* 31(9), 583-591.
13. Kraus, V. B., Huebner, J. L., Fink, C., King, J. B., Brown, S., Vail, T. P., and Guilak, F. (2002) *Arthritis Rheum* 46(2), 420-427
14. Misumi, K., Vilim, V., Hatazoe, T., Murata, T., Fujiki, M., Oka, T., Sakamoto, H., and Carter, S. D. (2002) *Equine Vet J* 34(6), 602-608.
15. Neidhart, M. (1996) *J Rheumatol* 23(3), 476-481.
16. Mansson, B., Carey, D., Alini, M., Ionescu, M., Rosenberg, L. C., Poole, A. R., Heinegard, D., and Saxne, T. (1995) *J Clin Invest* 95, 1071-1077
17. Lohmander, L. S., Ionescu, M., Jugessur, H., and Poole, A. R. (1999) *Arthritis Rheum* 42(3), 534-544.
18. Petersson, I. F., Boegard, T., Svensson, B., Heinegard, D., and Saxne, T. (1998) *Br J Rheumatol* 37(1), 46-50.
19. Briggs, M. D., Rasmussen, I. M., Weber, J. L., Yuen, J., Reinker, K., Garber, A. P., Rimoin, D. L., and Cohn, D. H. (1993) *Genomics* 18(3), 656-660
20. Briggs, M. D., Hoffman, S. M., King, L. M., Olsen, A. S., Mohrenweiser, H., Leroy, J. G., Mortier, G. R., Rimoin, D. L., Lachman, R. S., and Gaines, E. S. (1995) *Nature* 10(3), 330-336
21. Briggs, M. D., Mortier, G. R., Cole, W. G., King, L. M., Golik, S. S., Bonaventure, J., Nuytinck, L., De Paepe, A., Leroy, J. G., Biesecker, L., Lipson, M., Wilcox, W. R., Lachman, R. S., Rimoin, D. L., RG, K., and Cohn, D. H. (1998) *Am J Hum Genet.* 62(2), 311-319
22. Cohn, D. H., Briggs, M. D., King, L. M., Rimoin, D. L., Wilcox, W. R., Lachman, R. S., and Knowlton, R. G. (1996) *Ann NY Acad Sci* 785, 188-194
23. Hecht, J. T., Francomano, C. A., Briggs, M. D., Deere, M., Conner, B., Horton, W. A., Warman, M., Cohn, D. H., and Blanton, S. H. (1993) *Genomics* 18(3), 661-666
24. Hecht, J. T., Nelson, L. D., Crowder, E., Wang, Y., Elder, F. F., Harrison, W. R., Francomano, C. A., Prange, C. K., Lennon, G. G., and Deere, M. (1995) *Nat Genet.* 10(3), 325-329
25. Susic, S., McGrory, J., Ahier, J., and Cole, W. G. (1997) *Clin Genet.* 51(4), 219-224
26. Wright, W. E., Sassoon, D. A., and Lin, V. K. (1989) *Cell* 56(4), 607-617
27. Zhou, J., Gao, G., Crabb, J. W., and Serrero, G. (1993) *J Biol Chem* 268(15), 10863-10869
28. Davidson, B., Alejandro, E., Florenes, V. A., Goderstad, J. M., Risberg, B., Kristensen, G. B., Trope, C. G., and Kohn, E. C. (2004) *Cancer* 100(10), 2139-2147
29. Zanocco-Marani, T., Bateman, A., Romano, G., Valentinis, B., He, Z. H., and Baserga, R. (1999) *Cancer Res* 59(20), 5331-5340
30. Lu, R., and Serrero, G. (2000) *Proc Natl Acad Sci USA* 97(8), 3993-3998
31. Hrabal, R., Chen, Z., James, S., Bennett, H. P., and Ni, F. (1996) *Nat Struct Biol* 3(9), 747-752
32. He, Z., and Bateman, A. (2003) *J Mol Med* 81(10), 600-612
33. Anakwe, 0.0., and Gerton, G. L. (1990) *Biol Reprod* 42(2), 317-328

34. Baba, T., Hoff, H. B., 3rd, Nemoto, H., Lee, H., Orth, J., Arai, Y., and Gerton, G. L. (1993) *Mol Reprod Dev* 34(3), 233-243
35. Daniel, R., He, Z., Carmichael, K. P., Halper, J., and Bateman, A. (2000) *J Histochem Cytochem* 48(7), 999-1009
36. Bateman, A., Belcourt, D., Bennett, H., Lazure, C., and Solomon, S. (1990) Biochem Biophys Res Commun 173 (3), 1161-1168
37. Gonzalez, E. M., Mongiat, M., Slater, S. J., Baffa, R., and Iozzo, R. V. (2003) *J Biol Chem* 278(40), 38113-38116
38. He, Z., Ong, C. H., Halper, J., and Bateman, A. (2003) *Nat Med* 9(2), 225-229
39. Jones, M. B., Spooner, M., and Kohn, E. C. (2003) *Gynecol Oncol* 88(1 Pt 2), S136-139
40. Wang, W., Hayashi, J., Kim, W. E., and Serrero, G. (2003) *Clin Cancer Res* 9(6), 2221-2228
41. Zhang, H., and Serrero, G. (1998) *Proc Natl Acad Sci USA* 95(24), 14202-14207
42. Sell, C., Dumenil, G., Deveaud, C., Miura, M., Coppola, D., DeAngelis, T., Rubin, R., Efstratiadis, A., and Baserga, R. (1994) *Mol Cell Biol* 14(6), 3604-3612
43. Xu, S. Q., Tang, D., Chamberlain, S., Pronk, G., Masiarz, F. R., Kaur, S., Prisco, M., Zanocco-Marani, T., and Baserga, R. (1998) *J Biol Chem* 273(32), 20078-20083
44. Sun, X., Gulyas, M., and Hjerpe, A. (2004) *Am J Respir Cell Mol Biol* 30(4), 510-518
45. Suzuki, M., and Nishiahara, M. (2002) *Mol Genet Metab* 75(1), 31-37
46. Barreda, D. R., Hanington, P. C., Walsh, C. K., Wong, P., and Belosevic, M. (2004) *Dev Comp Immunol* 28(7-8), 727-746
47. Justen, H. P., Grunewald, E., Totzke, G., Gouni-Berthold, I., Sachinidis, A., Wessinghage, D., Vetter, H., Schulze-Osthoff, K., and Ko, Y. (2000) *Mol Cell Biol Res Commun* 3(3), 165-172
48. Zhu, J., Nathan, C., Jin, W., Sim, D., Ashcroft, G. S., Wahl, S. M., Lacomis, L., Erdjument-Bromage, H., Tempst, P., Wright, C. D., and Ding, A. (2002) *Cell* 111(6), 867-878
49. Liu, C. J., Wang, H., and Lengyel, P. (1999) *Embo J* 18(10), 2845-2854.
50. Vojtek, A. B., Hollenberg, S. M., and Cooper, J. A. (1993) *Cell* 74(1), 205-214.
51. Hollenberg, S. M., Sternglanz, R., Cheng, P. F., and Weintraub, H. (1995) *Mol Cell Biol* 15(7), 3813-3822.
52. Liu, C. J., Ding, B., Wang, H., and Lengyel, P. (2002) *Mol Cell Biol* 22(9), 2893-2905.
53. Di Cesare, P. E., Fang, C., Leslie, M. P., Della Valle, C. J., Gold, J. M., Tulli, H., Perris, R., and Carlson, C. S. (1999) *J Orthop Res* 17, 437-445
54. Hoque, M., Tian, B., Mathews, M. B., and Pe'ery, T. (2005) *J Biol Chem* 280(14), 13648-13657
55. Hoque, M., Young, T. M., Lee, C. G., Serrero, G., Mathews, M. B., and Pe'ery, T. (2003) *Mol Cell Biol* 23(5), 1688-1702
56. Thornburg, N. J., Kusano, S., and Raab-Traub, N. (2004) *J Virol* 78(23), 12848-12856
57. Liu, C., Dib-Hajj, S. D., and Waxman, S. G. (2001) *J Biol Chem* 276(22), 18925-18933.
58. Liu, C. J., Dib-Hajj, S. D., Renganathan, M., Cummins, T. R., and Waxman, S. G. (2003) *J Biol Chem* 278(2), 1029-1036.
59. Liu, C. J., Kong, W., Ilalov, K., Yu, S., Xu, K., Prazak, L., Fajardo, M., Sehgal, B., and Di Cesare, P. E. (2006) *Faseb J* 20(7), 988-990
60. Shoyab, M., McDonald, V. L., Byles, C., Todaro, G. J., and Plowman, G. D. (1990) *Proc Natl Acad Sci USA* 87(20), 7912-7916
61. Chen, F. H. T., A 0; Zhang, F; Hecht, J T; Lawler, J. (2004) *50th Annual meeting of Orthopaedic Research Society*, March 7-10, San Francisco, Calif.
62. Di Cesare, P. E., Chen, F. S., Moergelin, M., Carlson, C. S., Leslie, M. P., Perris, R., and Fang, C. (2002) Matrix Biol 21(5), 461-470.
63. Rosenberg, K., Olsson, H., Morgelin, M., and Heinegard, D. (1998) *J Biol Chem* 273, 20397-20403
64. Mann, H. H., Ozbek, S., Engel, J., Paulsson, M., and Wagener, R. (2004) *J Biol Chem* 279(24), 25294-25298
65. Hecht, J. T., Hayes, E., Snuggs, M., Decker, G., Montufar-Solis, D., Doege, K., Mwalle, F., Poole, R., Stevens, J., and Duke, P. J. (2001) *Matrix Biol* 20(4), 251-262
66. Duke, J., Montufar-Solis, D., Underwood, S., Lalani, Z., and Hecht, J. T. (2003) *Apoptosis* 8(2), 191-197
67. Vranka, J., Mokashi, A., Keene, D. R., Tufa, S., Corson, G., Sussman, M., Horton, W. A., Maddox, K., Sakai, L., and Bachinger, H. P. (2001) *Matrix Biol* 20(7), 439-450
68. Ozbek, S., Engel, J., and Stetefeld, J. (2002) *Embo J* 21(22), 5960-5968
69. Liu, C. J., Kong, W., Xu, K., Luan, Y., Ilalov, K., Sehgal, B., Yu, S., Howell, R. D., and Di Cesare, P. E. (2006) *J Biol Chem* 281(23), 15800-15808

EXAMPLE 2

GEP Expression in Chondrocytes

GEP Expression in Long Bone

We next examined the expressions of GEP and COMP in the section of long bone from 19-day-old embryo. In line with previously findings on COMP expression in vivo, COMP was expressed in both chondrocytes and also osteoblasts (FIGS. 9B and 9D). Expression of GEP, however, was localized exclusively to the lower proliferative and upper hypertrophic zones of the growth plate chondrocytes, and was absent in osteocytes, osteoblasts, periosteum and perichondrium (FIGS. 9A and 9C). Take together, expression of GEP in musculoskeletal tissues appears to be restricted to chondrocytes and is concentrated in areas where ossification will occur. Although COMP also expresses in the chondrocytes of growth plate, it demonstrates a broader expression pattern (FIGS. 9B and 9D).

GEP is Expressed in the RCS Chondrocytes but Absent in the MG-63 Osteoblasts

Figure 10:
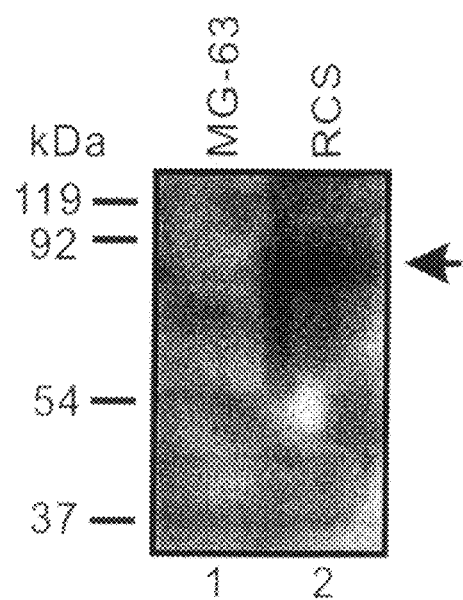
FIG. 10 depicts immunoblotting assay with GEP-specific antibody on RCS and MG-63 cells. Arrow indicates the GEP band with the apparent molecular weight of approximately 90 kDa.

Chondrocyte-specific expression of GEP in vivo promoted us to examine its expression in the well-established chondrocyte and osteoblast cell lines. Here we performed a Western Blotting assay with RCS and MG-63 as chondrocyte and osteoblast cell line respectively. As shown in FIG. 10, a specific and strong band was observed in the cell extracts prepared from RCS chondrocytes but not from MG-63 osteoblasts. These findings provide excellent in vitro cell models for determining the activities of GEP-specific reporter genes and dissecting the regulatory elements.

Differential-expression of GEP in the Chondrogenesis of a Micromass Culture of C3H10T1/2 Cells.

We next examined whether the GEP level changes in the course of chondrocyte differentiation, using BMP-2 induced chondrogenesis. The pluripotent murine mesenchymal stem cell line 10T1/2, a well established cell line for in vitro chondrogenic differentiation assays, was previously used for studying COMP gene expression in chondrogenesis in our lab (Liu, et al (2004) J Biol. Chem. 279(45):47081-47091) and here we utilized the same cell model to investigate GEP expression during chondrogenesis. Micromass cultures of 10T1/2 progenitor cells were incubated in 35-mm dishes in Dulbecco's modified Eagle's medium with 10% fetal bovine serum in the presence of 100 ng/ml exogenous recombinant BMP-2. Cultures were harvested at various time points, and a real-time PCR was performed using GEP-specific primers. Total RNA was extracted by the acid-guanidium thiocyanate-phenol-chloroform single-step method followed by RNAeasy kit (Qiagen, Valencia, Calif.). One microgram of total RNA per sample was reverse-transcribed using the ImProm-II Reverse Transcription system (Promega, Madison, Wis.). The following sequence-specific primers were synthesized: 5'-CCACTGTCCTGCTGGCTATT-3' (SEQ ID: 20) and 5'-CACTGCCCTGTTGGTCTTTT-3' (SEQ ID NO:21) for mouse GEP. PCR was performed for 35 cycles (94° C. 1 min, 60° C. 1 min, and 72° C. 1 min) with a final elongation for 10 min at 72° C. GAPDH was also amplified as an internal control for 35 cycles (94° C. 1 min, 55° C. 1 min, 72° C. 1.5 min). The PCR product was analyzed by 1% agarose gel electrophoresis and further sequenced by the Applied Biosystems sequencing system (Foster City, Calif.).

Figure 9:
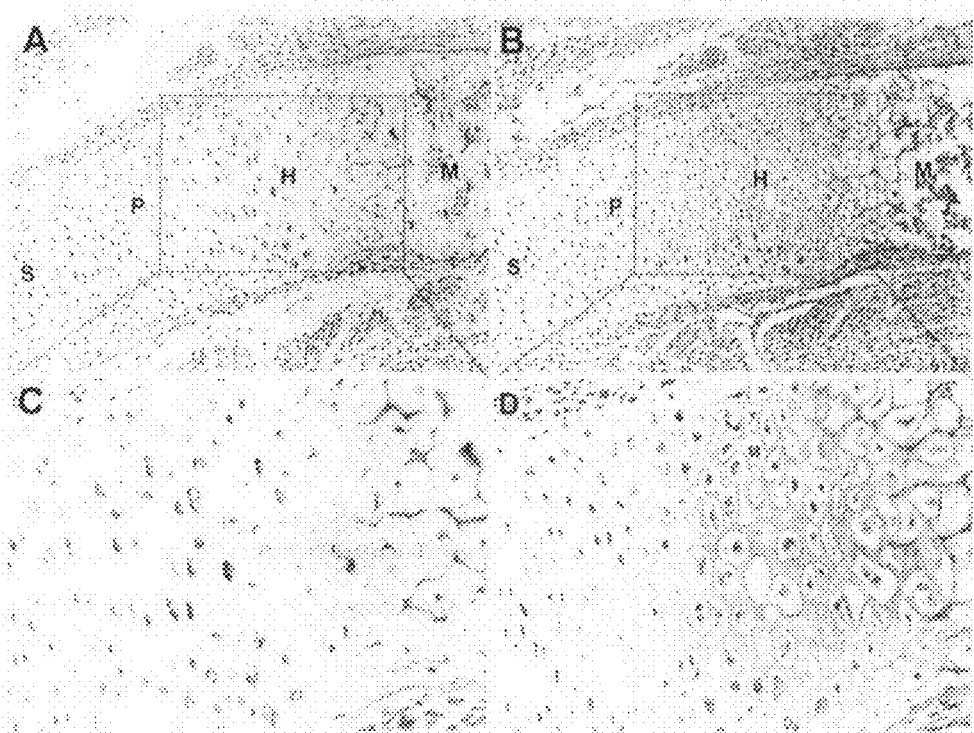
FIG. 9A-9D provide immunohistochemistry of GEP and COMP in the section of long bone from a 19-day-old mouse embryo. (A) Low-power microphotograph of section stained with anti-GEP antibody (red) and counter stained with Mayer's hematoxylin (blue); immunostaining for GEP demonstrating localization of strongly immunopositive chondrocytes in the lower proliferative/upper hypertrophic zones of the growth plate. (B) Low-power microphotograph of section stained with anti-COMP antibody (red) and counter stained with Mayer's hematoxylin (blue); immunostaining reveals positive staining in chondrocytes and osteoblasts. (C) High-power microphotograph of section in A. (D) High-power microphotograph of section in B. Key: S, resting chondrocytes; P, proliferating chondrocytes; H, hypertrophic chondrocytes; M, bone metaphysis. Bar=100 μm.
Figure 11:
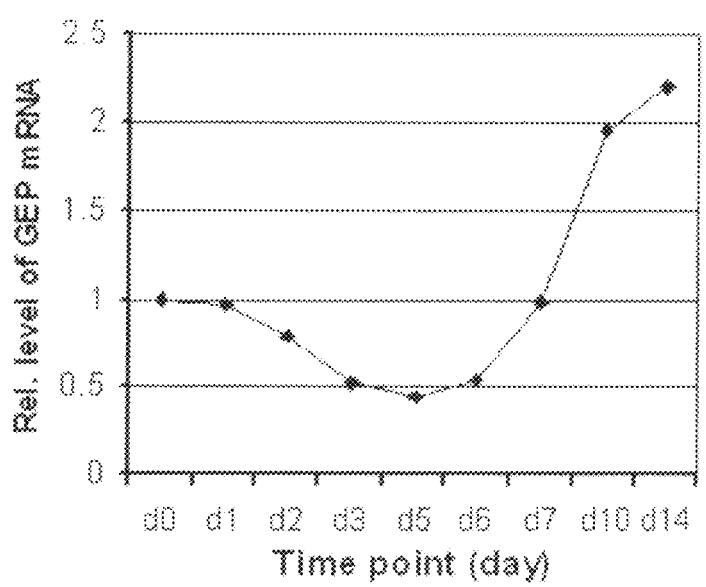
FIG. 11 depicts differential expression of GEP in the course of BMP-2-induced chondrogenesis in a micromass culture of 10T1/2 cells. Assayed for GEP mRNA by real-time PCR with GEP-specific primers.

As revealed in FIG. 11, GEP is differentially expressed during chondrogenesis in vitro and mimics its in vivo expression pattern in the growth plate during embryogenesis (see FIGS. 7 and 9). GEP mRNA is clearly expressed in the 10T1/2 cells, which is probably important for stimulating the proliferation and expanding the cell number of mesenchymal stem cells. The level' of GEP is actually going down in the early phase of the differentiation process, at which mesenchymal cells cease proliferation and are committed for differentiation, and its expression is dramatically induced in the late stage and reaches higher level, which corresponds to the expression of Collagen X, a specific marker of hypertrophic chondrocyte. Differential expression pattern of GEP during chondrogenesis suggests that GEP may play dual roles in the control of chondrogenesis and cartilage formation: expanding the number of mesenchymal cells and affecting the differentiation process, especially hypertrophic differentiation of chondrocytes.

EXAMPLE 3

Effects of Chondrogenic Growth Factors and Cytokines on GEP Expression

Expression of GEP in the presence of chondroinductive growth factors such as TGF-13, BMP-2, proinflammatory cytokines IL-1beta and TNF-alpha as well as noggin (antagonist of BMPs), was studied in human chondrocytes by regular RT-PCR using human-GEP primers (upstream primer 5'-GTGCCTTCTGCGACCTGGTT-3 (SEQ ID NO: 7) and downstream primer (5'-AGGTCCGTGGTAGCGTTCTC-3' (SEQ ID NO: 8), which generated a 306 bp product (FIG. 12A). The cells were adapted to serum free medium conditions for 24 h before treating with either TGF-β (5 ng/ml), BMP-2 (100 ng/ml), IL-1beta (5 ng/ml), TNF-alpha (5 ng/ml) and noggin (100 ng/ml) for 24 h and the cells were harvested for RNA isolation. As shown, TGF-13, BMP-2 and TNF-alpha each strongly enhanced the expression of GEP expression after 24 hours exposure, whereas IL-1 beta and noggin produced negligible induction, if at all, on GEP expression. To precisely quantify the effects of these factors and cytokines on GEP gene expression, a real time PCR was performed with the same cDNAs as templates. In this case, real-time PCR primers, generating a 140 bp product were utilized (up primer 5'-TCCGATACCTGCTGCCAACT-3' (SEQ ID NO: 9) and down primer 5'-CTCGCTTCCTCGCTGACACT-3' (SEQ ID NO: 10). As revealed in FIG. 12B, TGF-beta, BMP-2 and TNF-alpha significantly stimulated GEP expression and produced approximately 2-5 fold induction. Among them, TNF-alpha appears to be the most potent stimulator of GEP gene activity, which gave rise to approximately 5-fold induction.

Figure 12:
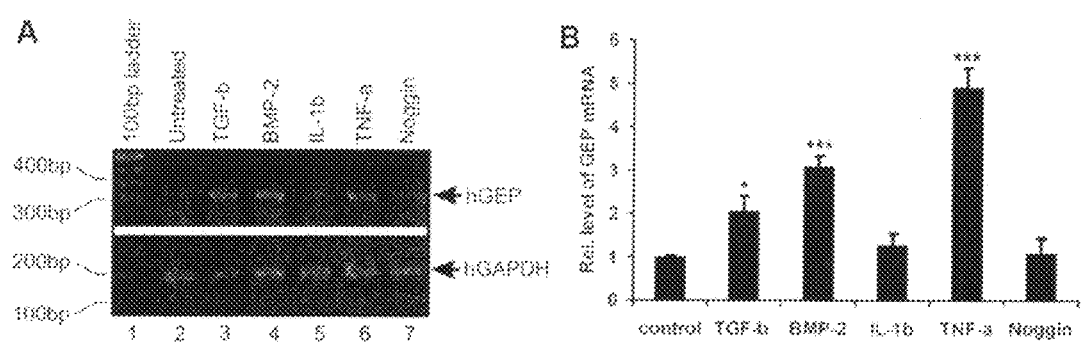
FIGS. 12A and 12B. Growth factors and cytokines induce GEP expression in Human chondrocytes. (A) RT-PCR assay. Amplification products are consistent with a predicted size of 307 base pairs (bp) for GEP and 170 bp for GAPDH. (B) Real-time PCR assay; expression of GEP in each sample was normalized against the 18S rRNA endogenous control. The normalized values were then calibrated against untreated chondrocytes value. The units are arbitrary, and the leftmost bar indicates a relative level of GEP of 1. *p<0.05; ***, p<0.001 vs. untreated control.

GEP is an autocrine growth factor and secreted into the medium of several cultured cell lines in vitro (Wright, W. E. et al (1989) Cell 56(4):607-617; Thou, J. et al (1993) J Biol Chem 268(15):10863-10869), we next assessed whether GEP is also secreted in cultured cartilage explants and if so whether its secretion is regulated by the above-mentioned growth factor and cytokines, BMP-2, TGF-beta and TNF-alpha. Cartilage slices from OA patients undergoing total knee arthroplasty were cut into 3 mm-diameter discs for organ culture. Cartilage discs were placed in organ culture in Ham's F-12 media, 10% charcoal-stripped fetal calf serum, 1 mg/ml bovine serum albumin, 20 mM Hepes, pH 7.4, 50 µg/ml of gentamycin, and 0.25 µg/ml fungizone. After 1 day in culture, organ cultures were stimulated with indicated growth factors and cytokines for an additional 7 days. Medium was collected for detecting the GEP level by Western Blotting assay. As shown in FIG. 13A, GEP, which was not present in the medium used (not shown), was clearly detectable in the medium of cultured cartilage explants (lane 1), clearly indicating that GEP was a secreted growth factor in the cartilage organ culture. This secretion was strongly enhanced by TGF-beta (5 ng/ml), BMP-2 (100 ng/ml) and TNF-alpha (5 ng/ml), which is in consistent with their effects on GEP mRNA expression in chondrocytes. Intriguingly, in addition to the full length GEP band, an additional band was observed in response to the treatments of TNF-alpha and BMP-2 (FIG. 13A, lane 3 and 4), suggesting that these two factors may also induce the proteolysis of GEP. Similar to its effects on GEP mRNA expression (FIG. 12), IL-1beta (5 ng/ml) did not show prominent induction on GEP secretion (FIG. 13A, lane 5). In the case of noggin (100 ng/ml), it appears that it inhibits the secretion of GEP (FIG. 13A, lane 6) although it did not produce a clear effect on GEP gene expression in human chondrocytes (FIG. 12). Since TNF-alpha was found to be the strongest inducer of GEP gene expression and secretion (FIG. 12B), it was selected to perform a dose-dependent secretion assay. As shown in FIG. 13B, within a range of 20 ng/ml, secretion of GEP into the medium of cultured cartilage explants in response to TNF-alpha exposure is does-dependent.

EXAMPLE 4

Effects of GEP on Expression of BMP-2, TGF-Beta and TNF-Alpha

Figure 13:
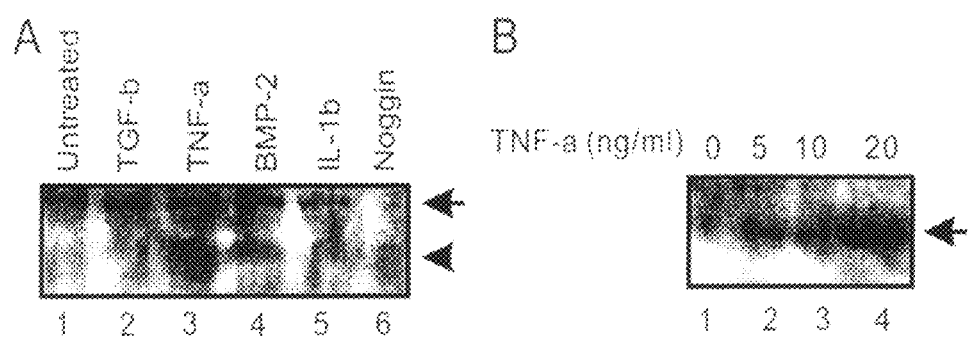
FIGS. 13A and 13B. GEP is secreted into the medium of cartilage explants and its secretion is regulated by growth factors and cytokines, assayed by immunoblotting. (A) Effects of growth factors and cytokines on GEP secretion. The full length GEP and a processed peptide are indicated. (B) Does-dependent effect of TNF-α on GEP secretion.
Figure 14:
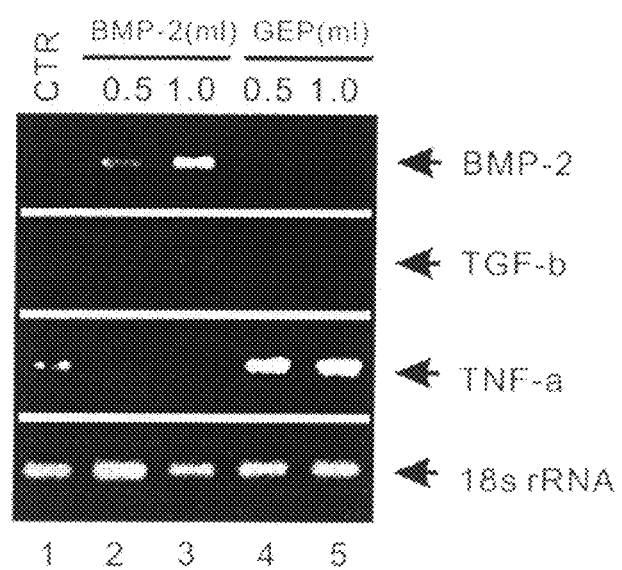
FIG. 14 depicts the effects of GEP on the expression of BMP-2, TGF-β and TNF-α. Isolated human chondrocytes were cultured in the presence of control medium (CTR), BMP-2-, or GEP-conditioned medium, as indicated for 2 days and the expression of BMP-2, TGF-beta and TNF-alpha were determined by RT-PCR.

We also investigated whether GEP affects the expression of growth factors BMP-2 and TGF-beta and pro-inflammatory cytokine TNF-alpha that were shown to induce the expression of GEP in human chondrocytes (FIG. 12 and FIG. 13). For this purpose, we first produced GEP-conditioned medium. Very briefly, thirty micrograms of hBMP-2-HA (serves as a control) or hGEP-Flag expression plasmids was transfected into 293T cells in a 10-cm dishes. At 48 hr posttransfection, the conditioned medium containing the expressed protein was collected. Isolated human chondrocytes were cultured in the presence of control medium (CTR), BMP-2-, or GEP-conditioned medium, as indicated in FIG. 14, for 2 days and the expressions of BMP-2, TGF-beta and TNF-alpha were determined by RT-PCR. Different from BMP-2 that induced the expression of itself and TGF-beta which repressed TNF-alpha expression, GEP did not produced any induction in the expression of BMP-2 and TGF-beta, suggesting GEP action is not realized via inducing BMP-2 and TGF-beta expression. Intriguingly, GEP clearly increased the TNF-alpha mRNA level, although it was reported that GEP inhibited TNF-alpha mediated activation of inflammatory cells and blocked its biological activities (He, Z. et al (2003) Nat Med 9(2):225-229; Zhu, J. et al (2002) Cell 111:867-878).

EXAMPLE 5

Increased Expression of GEP in the Cartilage of Patients with Arthritis

Figure 15:
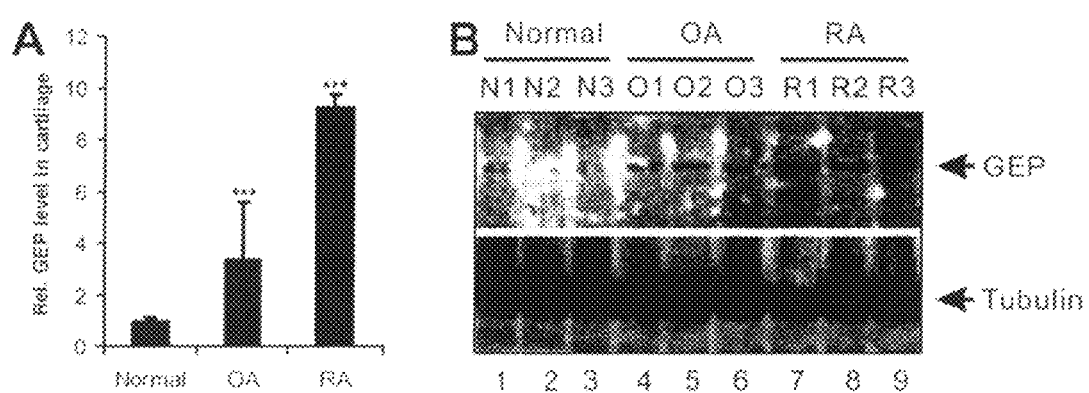
FIGS. 15A and 15B depicts increased expression of GEP in the arthritic cartilage. (A) Expression of GEP mRNA in normal, OA, and RA cartilage, assayed by real-time PCR. The units are arbitrary and the leftmost bar indicates a relative level of GEP of 1. ***, p<0.001 vs. normal control. (B) Expression of GEP protein in normal, OA and RA cartilage, assayed by Western Blotting. Tubulin was used as an internal control.

To determine whether the expression of GEP in cartilage is altered in OA or RA, a quantitative real-time PCR was performed. Human real-time PCR primers (up primer 5'-TCCGATACCTGCTGCCAACT-3' (SEQ ID NO: 9) and down primer 5'-CTCGCTTCCTCGCTGACACT-3' (SEQ ID NO: 10)) were utilized using the same conditions as provided in Example 2 above for mouse GEP PCR. Normal adult articular cartilages were obtained from the knees of four patients who had died of diseases unrelated to arthritis (from the Musculoskeletal Transplant Foundation). Arthritic cartilage were obtained from 12 patients undergoing elective total knee arthroplasty for end-stage arthritis: OA articular cartilage (Kellgren-Lawrence Grade 3 or 4) from the distal femora of 8 patients and RA cartilage (American College of Rheumatology Stage III and IV disease) from the knees of 4 RA patients who fulfilled the revised criteria of the American College of Rheumatology for the diagnosis of RA (Arnett, F. C. et al (1988) Arthritis Rheum 31(3):315-24). As shown in FIG. 15A, GEP mRNA was significantly upregulated in both OA and RA cartilage (p<0.001) compared to the normal control.

To assess GEP protein expression in OA and RA cartilage, we next performed Western blot analyses. Total cartilage extracts from 3 normal, 3 OA and 3 RA were resolved using 10% SDS-PAGE and probed with anti-GEP and tubulin (serves as internal control) antibodies respectively (FIG. 15B). Consistent with the expression pattern of GEP mRNA, arthritic samples, particularly cartilage from rheumatology arthritis patients, showed elevated expression of GEP as compared to normal cartilage.

EXAMPLE 6

Expression of GEP During Chondrogenesis of MSCs

Figure 16:
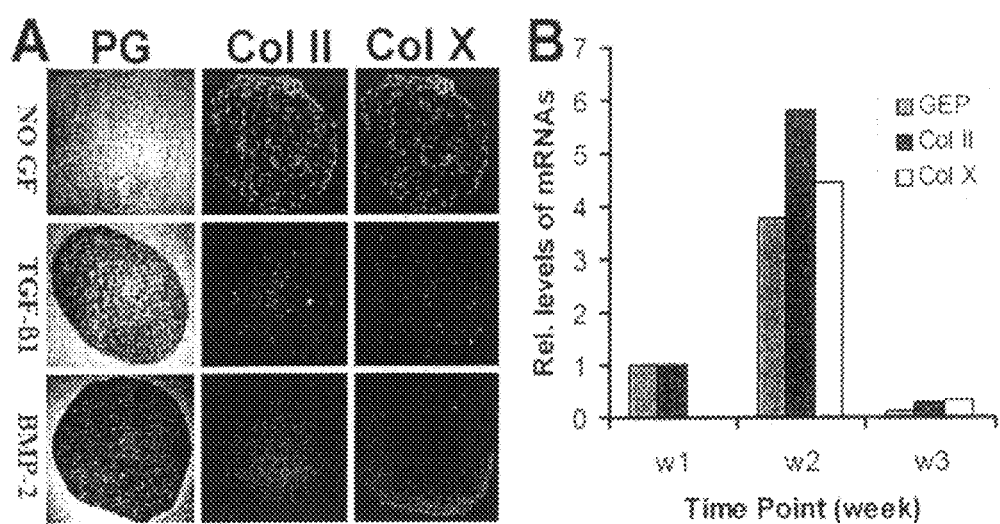
FIGS. 16A and 16B depicts (A) Chondrogenesis of hMSCs following exposure to TGF-β and BMP-2. High density aggregates of MSCs exposed to BMP-2 or TGF-b1 were sectioned and stained for the presence of chondrogenic markers using toluidine blue (proteoglycan) and immunostaining for type II and X collagen. (B) GEP expression in the chondrogenesis of hMSCs. Aggregates of MSCs exposed to BMP-2 and TGF-b1 were collected at indicated time points and expressions of GEP, collagen II and collagen X were examined by real-time PCR.

When cultured as high density aggregates postnatal mesenchymal stem cells also undergo chondrogenesis (Johnstone B et al (1998) Exp Cell Res 238(1):265-272). Following exposure to chondrogenic growth factors, cultures exhibit metachromatic staining with toluidine blue and corresponding immunostaining for type II collagen, characteristic of cartilage extracellular matrix. In preliminary studies, we have found that adult bone marrow-derived MSCs undergo chondrogenesis in aggregate cultures following exposure to TGF-β1 and BMP-2 in agreement with the findings of others (Johnstone B et al (1998) Exp Cell Res 238(1):265-272; Barry F et al (2001) Exp Cell Res 268:189-200; Palmer G D et al (2005) Mol Ther 12(2):219-228). Upon histological examination we noted important differences between TGF-β1 and BMP-2-treated cultures (FIG. 16A). BMP-2-treated cultures were typically larger, more cellular and showed more intense staining for proteoglycan, type II and type X collagen, whereas staining in TGF-β1-treated aggregates was generally lower. These findings suggest that TGF-β1 and BMP-2 modulate chondrocyte differentiation to differing extents. We examined the expression of GEP during this process induced by a combination of 50 ng/ml BMP-2 and 5 ng/ml of TGF-beta (FIG. 16B). GEP is detectable at week 1, but reaches highest level by week 2, at which time point collagen X, a specific marker for hypertrophic chondrocyte, was also highly expressed; it is almost undetectable by week 3. These findings support our in vivo observations revealing highest expression of GEP in growth plate hypertrophic chondrocytes (see FIG. 9). This model can be used to investigate the role of GEP in chondrogenesis via "gain-of-function" and "loss-of-function" assays in the absence or presence of known chondroinductive factors.

EXAMPLE 7

Ectopic Expression of GEP Affects Proliferation of MSCs

Figure 17:
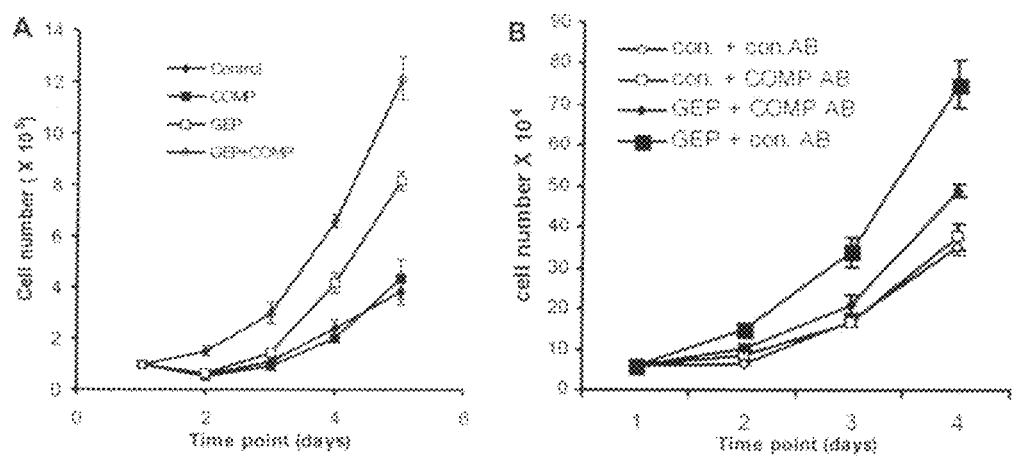
FIGS. 17A and 17B depicts the effects of GEP over expression on the proliferation of C3H10T1/2 mesenchymal stem cells. (A) Cell number assay. Stable lines, as indicated, were counted every day until day 4. (B) MTT assay. Stable lines, as indicated, were measured every day until day 4. Both control (CTR) and GEP group were repeated three times.

Since GEP was reported to have potent mitogenic effects on cancer cells (Zanocco Marani, T et al (1999) Cancer Res 59(20):5331-5340; Davidson, B et al (2004) Cancer 100(10): 2139-2147; Bateman, A et al (1990) Biochem Biophys Res Comm 173(3):1161-1168; Gonzalez, E. M. et al (2003) J Biol Chem 278(40):38113-38116; He, Z and A. Bateman (2003) J Mol Med 81(10):600-12; He, Z., et al (2003) Nat Med 9(2): 225-229; Jones, M. B., M. Spooner, and E. C. Kohn (2003) Gynecol Oncol 88(1 Pt 2):S136-139; Wang, W., et al. (2003) Clin Cancer Res 9(6):2221-2228; Zhang, H. and G. Serrero (1998) Proc Natl Acad Sci U.S.A. 95(24):14202-14207; Xu, S. Q., et al. (1998) J Biol Chem 273(32):20078-20083), we next evaluated the proliferative function of GEP in C3H10T1/2 mesemchymal stem cells. We first generated GEP and control stable lines in 10T1/2 cells and with them performed cell growth assays. Cell counting results showed that overexpression of GEP clearly increased the growth of 10T1/2 cells (FIG. 17A) and MTT assay that measures the cell proliferation rate further verify the stimulation of GEP on the proliferation of stem cells. These observations demonstrate that GEP is capable of expanding the number and stimulating the proliferation rate of mesemchymal stem cells, which eventually contributes to enhance cartilage formation.

EXAMPLE 8

Figure 18:
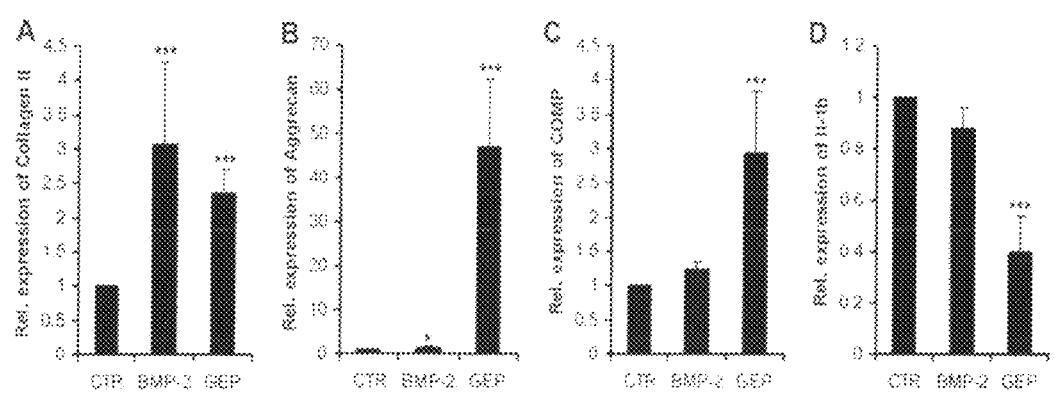
FIG. 18A-18D provides the effect of GEP-conditioned medium on chondrocyte metabolism as analyzed by Real-time PCR. Expression was normalized against the 18S rRNA. The normalized values were then calibrated against the control (CTR), given a value of 1. *p<0.05; ***p<0.001.

Effects of GEP on Expression of Anabolic and Catabolic Marker Genes in Human Chondrocytes We next examined whether GEP affects chondrocyte metabolism using monolayer culture of isolated human chondrocytes exposed to control, BMP-2- or GEP-conditioned medium. As shown in FIG. 18 (panel A, B and C), GEP-conditioned medium resulted in robust increases in the expressions of type II collagen, aggrecan and COMP relative to control, specially aggrecan that was increased approximately 45 fold by GEP. Addition of BMP-2-conditioned medium to the cultures also resulted in an approximately 3-fold increase in the mRNA level of type II collagen, and a doubling of the level of aggrecan mRNA relative to control, whereas the expression of the COMP gene was only slightly upregulated (19.8%). The effects of GEP and BMP-2 on the expression of the catabolic marker IL-1β was also examined (FIG. 21D). Cultures exposed to BMP-2-conditioned medium demonstrated only a slight decrease (14.6%), whereas GEP-conditioned medium led to a dramatic decrease in the level of IL-1β mRNA (61.6%), relative to controls (FIG. 21D). The data revealed that GEP strongly increased the expression of anabolic molecules (type II collagen, aggrecan and COMP) and decreased the expression of catabolic molecule IL-113. In this small pilot group, the findings suggest that GEP may be chondroprotective.

EXAMPLE 9

Comparison of GEP and BMP-2 in the Induction of Chondrogenesis

Figure 19:
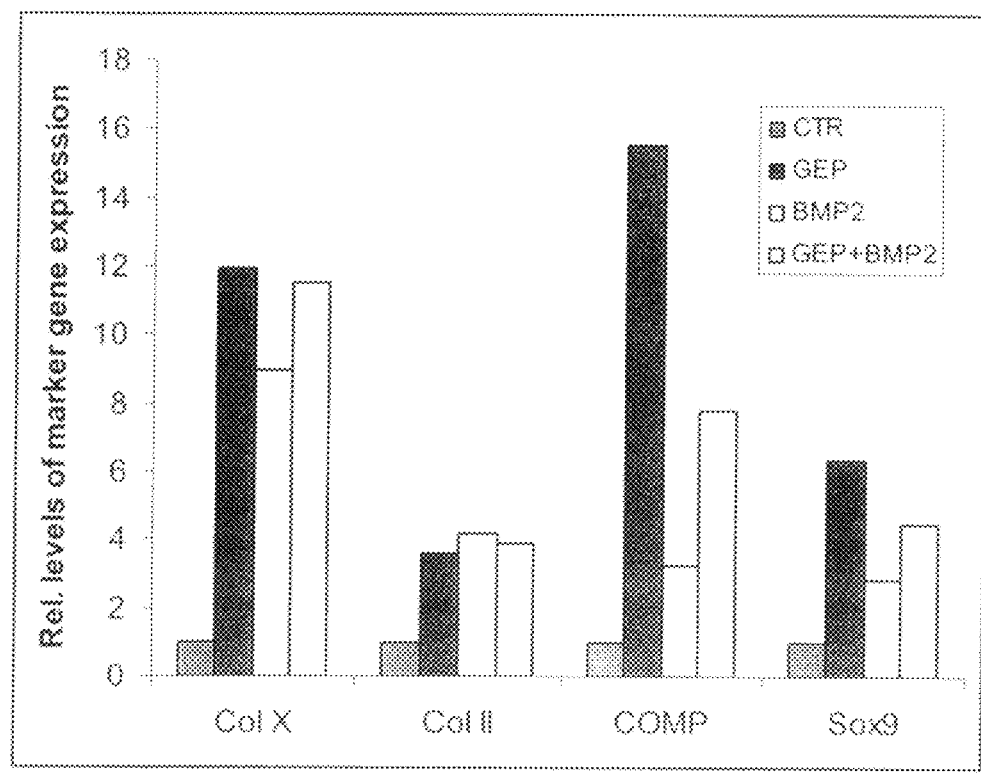
FIG. 19 depicts a comparison of GEP and BMP-2 in the induction of chondrogenesis. Mesenchymal 10T1/2 cells were treated with GEP, BMP-2, GAP and BMP-2 or nothing (CTR) and the relative levels of collagen X, collagen II, COMP and Sox9 mRNA determined by real-time PCR.

Mensenchymal stem 10T1/2 cells were treated with GEP, BMP-2 or both for 6 days and the expression of genes specific for chondrocyte were measured with real-time PCR. As shown in FIG. 19, GEP strongly induced the expression of all marker genes tested, including Collagen X, collagen II, COMP and Sox9. In addition to the induction of collagen II, GEP appears to be a stronger inducer for collagen X, a specific marker for hypertrophic chondrocyte. COMP and Sox9 are two early markers of chondrogenesis. GEP induced higher levels of expression of each of collagen X, collagen II, COMP and Sox9 than did BMP-2. Combinations of GEP and BMP-2 did not induce greater expression than did GEP alone.

EXAMPLE 10

Evaluation of GEP as a Chondrogenic Factor for Osteochondral Defect Repair

This study examines for the first time the chondrogenic potential of granulin (GEP). Our recently published gene therapy approach for treating damaged cartilage will be utilized (Di Cesare et al. (2006) J Orthop Res 24(5):1118-1127). Endotoxin-free cDNA containing the gene for granulin (see for example SEQ ID NO:1 and Genbank sequences NM002087 and gi183612) is placed in type I collagen sponges and then transfer the naked plasmid DNA construct to the injury site. The DiCesare et al published study demonstrated that a full-thickness cartilaginous defect in rabbits implanted with plasmid containing a marker gene (beta-galactosidase) showed expressed protein as detected by immunostaining. At 1 week postimplantation, mesenchymal cells subjacent to the defect had incorporated the implanted naked plasmid DNA and, once transfected, served as local bioreactors, transiently producing the gene product. In that study, plasmids containing the gene for BMP-2 implanted in collagen sponges in cartilage lesions stimulated hyaline-like articular cartilage repair at 12 weeks postimplantation, nearly equivalent in quality to that induced by collagen sponges with BMP-2 protein. Granulin is tested against BMP-2 and empty collagen sponges as controls.

Introduction

Normal joint function requires a smooth articular surface composed of hyaline cartilage. The response of normal articular cartilage to injury or damage often results in suboptimal repair because of the tissue's limited regenerative and reparative capabilities (Mankin H. J. (1982) J Bone Joint Surg Am 64:460-6; Mankin H J, et al (1994) "Form and function of articular cartilage" in SR Simon (ed): Orthopaedic Basic Science, Rosemont, Ill., American Academy of Orthopaedic Surgeons 1-44). Many of the current treatment options are aimed at stimulating extrinsic repair from cells deep to the tidemark. These techniques may temporarily alleviate clinical symptoms, but do not result in regeneration of tissue with structural, biochemical, and biomechanical properties resembling those of normal hyaline cartilage (Buckwalter J A and Lohmander S (1994) J Bone Joint Surg Am 76:1405-1418; Buckwalter J A, Mow V C, and Ratcliffe A (1994) J Am Acad Orthop Surg 2:192-201). Several peptide growth and differentiation factors have been identified that appear to control cellular events associated with cartilage formation and repair, including transforming growth factor-beta (TGF-β) (Hunziker E B (2001) Osteoarthritis Cartilage 9:22-32; Hunziker E B and Rosenberg L C (1996) J Bone Joint Surg Am 78:721-733; Joyce M E et al (1990) J Cell Biol 110:2195-2207), fibroblastic growth factor (Kato Y and Gospodarowicz D (1985) J Cell Biol 100:477-485), insulin-like growth factor (Osborn K D et al (1989) J Orthop Res 7:35-42), and bone morphogenetic proteins (BMPs) (Reddi A H (1995) Matrix Biol 14:599-606; Sumner D R, et al (1995) J Bone Joint Surg Am 77:1135-1147). In the above studies of the in vitro effects of the protein granulin, we have found that it has the following growth factor-like effects on cartilage: 1) expression of GEP is exclusively restricted to chondrocytes of musculoskeletal tissues and stimulates human chondrocyte proliferation; 2) It enhances the chondrogenesis in a micromass culture of pluripotent murine mesemchymal stem cells; and 3) its level is significantly elevated in the cartilage of patients with arthritis. These findings provide the first evidence that GEP is a novel chondrogenic growth factor and plays a previously unrecognized critical role in cartilage formation and possibly in the pathology of arthritis.

The purpose of this pilot study is to test the ability of granulin to enhance repair of full-thickness articular cartilage lesions, and to test its efficacy against that of a recognized chondrogenic agent, BMP-2 protein, and against a control, irrelevant gene plasmid.

Methods

Surgical Approach:

After induction of anesthesia with an intramuscular injection of ketamine and xylazine, full-thickness articular cartilage defects will be created bilaterally in the distal femora of four skeletally mature (9-month-old) male New Zealand White rabbits. A midline longitudinal incision and medial arthrotomy with lateral subluxation of the patella will be followed by the creation of a full-thickness (2-mm-deep), 3-mm-diameter femoral trochlear osteochondral defect using a Dremel power tool under steady irrigation. Each defect will then be grafted, the patella reduced, and the wound closed. Rabbits will be allowed unrestricted cage movement.

Defects will be treated with one of three implants:
(1) collagen sponge only (N=2);
(2) sponge containing 70 μg pc.hGranulin —HA (N=3);
(3) sponge containing 6 μg of rhBMP-2 protein (R & D Systems, Minneapolis, Minn.; dosage based on our previous studies) (N=3).

Data Analysis:

At 12 weeks postoperatively, animals will be sacrificed and specimens processed for routine histology with Hematoxylin and eosin (H&E) stain. Additional sections will be stained with toluidine blue (or Safranin-O) to highlight glycosaminoglycan distribution in the repair. Quality of repair will be evaluated blindly using a modified O'Driscoll histological grading system for cartilage repair (Frenkel S R, et al (1997) J Bone Joint Surg Br 79:831-836; O'Driscoll S W, Keeley F W and Salter R B (1986) J Bone Joint Surg Am 68:1017-1035). Analysis of variance will be used to analyze the data (with $p<0.05$ considered significant); Scheffe's test will be used for post hoc multiple comparisons.

EXAMPLE 11

Isolation of Human GEP Upstream Promoter Sequence and Promoter-Directed Expression of Reporter in Various Cell Lines The availability of the completed sequence of GEP gene in the GenBank allowed us to retrieve the 5' upstream sequence of GEP gene. We have now cloned approximately 1.6 kb of the 5'-flanking regulatory region of GEP gene by PCR using human genomic DNA as template. The sequence of upstream GEP promoter sequence is provided in FIG. 20 (SEQ ID NO: 13). Consensus sequences for transcription binding factors Smad3, AMUCBFA2, Smad4, E2F and NF-κB are indicated.

A roughly 1.6-kb segment from the 5"-flanking region of the human GEP gene (−1573 to +325) was linked to the upstream end of a region encoding luciferase in the pGL2 basic vector to generate a GEP-specific reporter gene plasmid pGL2-GEP-luc (FIG. 21A). This reporter plasmid and empty control were transfected into RCS (chondrosarcoma), 10T1/2 cells (pluripotent murine mesenchymal cell line), C2C12 cells (pluripotent murine mesenchymal cell line) and Saos-2 cells (osteosarcoma) and the luciferase activity was determined. As shown in the FIG. 21B, GEP-specific reporter gene was strongly active in RCS chondrocytes and also in 10T1/2 and C2c12 mesenchymal stem cells. The GEP-driven luciferase reporter gene was totally inactive in Saos-2 osteoblasts. These findings are in consistent with the expression pattern of endogenous GEP gene, i.e. GEP is specifically expressed in chondrocytes but absent in osteoblasts.

EXAMPLE 12

Inhibition of GEP with siRNA

Figure 22:
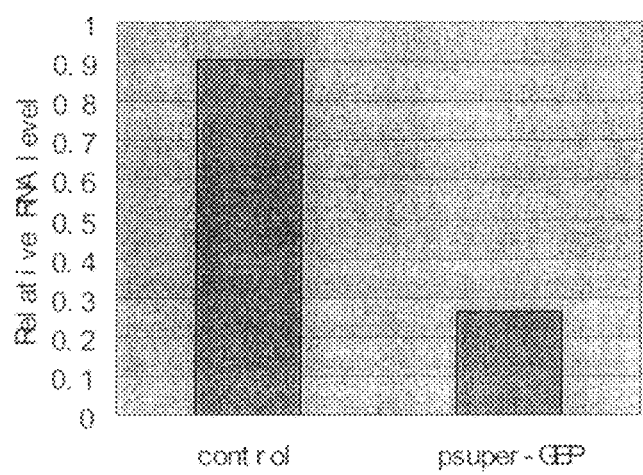
FIG. 22 depicts expression of GEP as assessed by RNA levels in 10T1/2 cells transfected with control or pSuper-GEP encoding siRNA.

GEP-specific siRNA was constructed against the target sequence GCCUAUCCAAGAACUACAC (SEQ ID NO: 14). This target sequence is located 775 bp downstream of the start code. Plasmid pSuper-GEP expressing siRNA (5'-GAT CCC CGC CTA TCC AAG AAC TAC ACT TCA AGA GAG TGT AGT TCT TGG ATA GGC TTT TTA—3' (SEQ ID NO:23)) was transfected into 10T1/2 cells and expression of GEP was dramatically inhibited (FIG. 22).

EXAMPLE 13

GEP Knockdown Transgenic Mice Demonstrate GEP Role in Cartilage and Bone Development Methods
Immunohistochemistry:

4 μm thick formalin fixed paraffin sections of 19 day-old embryonic murine limbs were immunostained for GEP. The sections were pretreated with chondroitinase (Sigma) for 30 mins at 37° C. followed by protein block (Dako Serum-Free Protein Block) for 10 minutes at room temperature to reduce non-specific staining. Polyclonal goat anti-human GEP (Santa Cruz) was diluted at 1:200 and incubated overnight at 4° C. Binding of primary antibodies was detected using biotinylated anti-goat secondary antibody (Jackson Labs) diluted at 1:800 and incubated for 30 minutes at 37° C., followed by alkaline-phosphatase (Vector) at 37° C. for 30 min, and developed with Vector Red (Vector) for 2 min at room temperature. Sections were counterstained with Mayer's Hematoxylin (Dako). The primary antibody was substituted with Negative Control SuperSensitive Goat Serum (BioGenex) for negative control sections.

Safranin O Staining:

Slides were placed in: xylene 10 min; 100% ethanol 10 min; 90% ethanol 10 min; 70% ethanol 10 min; Water; 0.02% Fast Green 3 minutes; 1% Acetic Acid 30 seconds; 0.1% Safranin O 5 minutes; Water; 70% ethanol 10 dips; 90% ethanol 10 dips; 100% ethanol 10 dips; Xylene 10 dips. Slides were then mounted with coverslips.

Results and Discussion

Generation of U6-ploxPneo-GEP Transgenic Mice and Crossing U6-ploxPneo-GEP Transgenic Mice to Sox2-Cre Mice.

To define the in vivo role of GEP during chondrogenesis, we created GEP knockdown mice via combining the small interfering RNA (siRNA) technique and the Cre/loxP system. siGEP (as described above in Example 12) is driven by U6 promoter that is disturbed by a loxP-flanked neomycin cassette. Briefly, we first generated U6-ploxPneo-GEP transgenic mice bearing the same target sequence against GEP. U6-ploxPneo-GEP transgenic lines were then crossed to Sox2-Cre transgenic mice, in which the Cre enzyme is driven by Sox2 promoter activated in earlier stage during embryonic development, in order to generate siGEP/Sox2-Cre knockdown (KD).

Initial Analyses of siGEP/Sox2-Cre Knockdown Mice.

Figure 24:
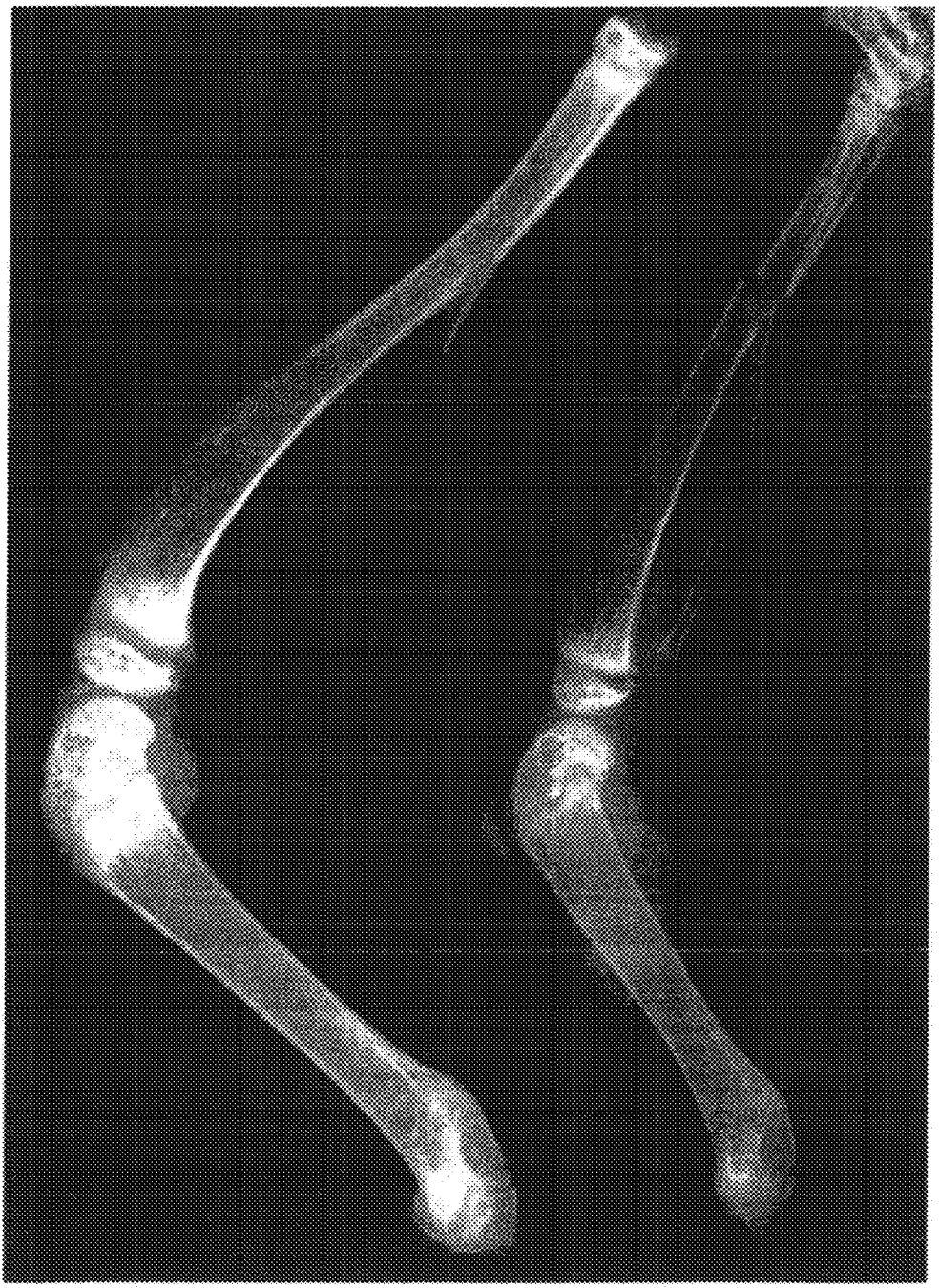
FIG. 24 shows reductions of skeleton length of tibia in 3 week old animals with knockdown (KD) versus wildtype (WT). Bone fracture in KD tibia is evident.

Immunohistochemistry with anti-GEP antibodies showed that the GEP level in growth plate chondrocytes in GEP knockdown lines (KD) was dramatically reduced when compared to the corresponding control (WT) (FIG. 23). GEP knockdown mice are viable but are smaller in size. X-ray analyses of whole animals and hind legs of 3-week-old KD and WT mice revealed that knockdown of GEP led to delayed skeletal development, short bone (osteopenia due to the reduction in bone volume), thinner cortical bone, and bone fracture (FIG. 24). Safranin O staining demonstrated that GEP knockdown resulted in abnormally narrow growth plates (reduction of growth plate width observed) and a dramatically diminished hypertrophic zone (FIG. 25), indicating that GEP plays an essential role in chondrogenesis in vivo, especially in chondrocyte hypertrophy. Collectively, these exciting, pilot studies clearly show that GEP is a novel chondrogenic growth factor and plays critical roles in cartilage and bone development.

EXAMPLE 14

Expression of Collagen II and X in Growth Plates in GEP Knockdown Mice

Materials and Methods
In Situ Hybridization (ISH):

The specimens of the femur from mouse 3-week wildtype (WT) and siGEP-Sox2-Cre knockdown knockdown (KD) mice are fixed in 4% paraformaldehyde, embedded in paraffin, and sectioned (5 μm thick). Sections are rehydrated with grated ethanol followed by DEPC-treated distilled water. Sections are permeabilized with 100 mM Tris-HCl, 50 mM EDTA, pH 8.0 (TE Buffer) containing RNase-free proteinase-K (1 μg/ml). Postfixation is performed with D-PBS containing 4% paraformaldehyde followed by D-PBS washes. Each section is then washed in prehybridization buffer (4× salt-sodium citrate [SSC] [1×SSC=150 mM NaCl, 15 mM sodium citrate, pH 7.2]) containing 50% v/v deionized formamide. Each section is probed with hybridization buffer (94% deionized formamide, 10% dextran sulfate, 1×Denhardt's solution [0.02% Ficoll, 0.02% polyvinylpyrrolidone, 10 mg/ml RNase-free bovine serum albumin], 4×SSC, 10 mM DTT, 1 mg/ml yeast RNA, 1 mg/ml denatured and sheared salmon sperm DNA) containing 10 ng of either sense or antisense digoxigenin-labeled Col II or Col X riboprobe at 42° C. overnight in a humid chamber. For posthybridization, slides are washed in 2×SSC, unbound single-stranded probe digested in NTE buffer (500 mM NaCl, 10 mM Tris, 1 mM EDTA, pH 8.0) containing 20 μg/ml RNase A. Sections are washed with 0.1×SSC buffer followed by 100 mM Tris/HCl, 150 mM NaCl, pH 7.5, and blocked with the last buffer containing 2% sheep serum, 0.1% Triton X-100, 100 mM Tris/HCl, 150 mM NaCl, pH 7.5, for 30 min at room temperature. Bound probe is detected by an alkaline phosphatase-linked sheep antidigoxigenin antibody and the addition of nitroblue tetrazolium and 5-bromo-4-chloro-3-indolyphosphate as a substrate (Genius Nucleic Acid Detection Kit, Indianapolis, Ind.). Cells expressing ADAMTS-7 mRNA exhibit a dark blue-black reaction product as visualized by light microscopy.

Results and Discussion

Figure 26:
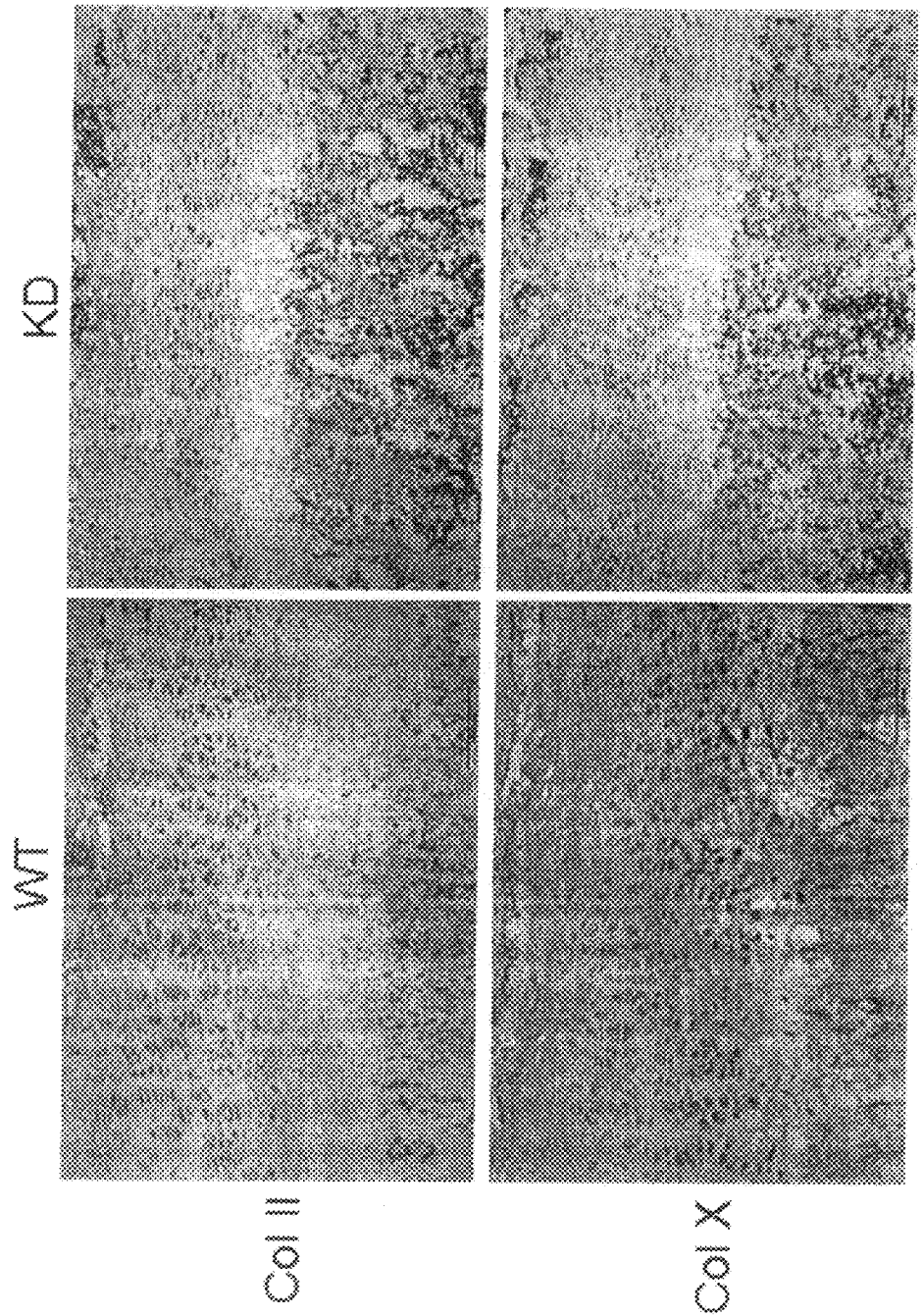
FIG. 26 depicts ISH of Col II, Col X and AP in the sections of the femur from mouse 3-week wildtype (WT) and siGEP-Sox2-Cre knockdown knockdown (KD) mice.

Since GEP induces Col II, Col X expression and knockdown of GEP dramatically inhibits their expression, in in vitro chondrogenesis, we examined their expression in the growth plate in GEP knockdown mice using ISH. As shown in FIG. 26, both Col II and Col X were markedly reduced in the growth plates in GEP knockdown mice although high expressions of Col II in the proliferating zone and Col X in the hypertrophic chondrocytes in wildtype mice were observed. Note that Col X was almost undetectable in the growth plates chondrocytes in GEP KD mice. In addition, GEP KD mice also exhibit reduced alkaline phosphatase (AP) expression in growth plates (FIG. 26). Collectively, these exciting studies clearly show that GEP is novel chondrogenic growth factor and plays critical roles in cartilage and bone development.

EXAMPLE 15

Defining the Minimal Promoter and the Regulatory Elements in the 5'-Flanking Region of the GEP Gene Materials and Methods Reporter Gene Assay RCS cells grown to approximately 50% confluence in 35-mm culture dishes were transfected with 1 μg of the various reporter constructs along with 1 μg of pSVGal plasmid (internal control) in the absence or presence of 100 ng/ml of BMP-2 or expression plasmids encoding Smad4, Smad1, Smad5 or various combinations. At 48 h after transfection, the cultures were harvested and lysed. Luciferase assays were performed using 20 μl of cell extract and 100 μl of luciferin substrate (Promega). β-Galactosidase assays were performed using a β-galactosidase assay kit (Tropix, Foster City, Calif.) per the manufacturer's protocol. β-Galactosidase and luciferase activities were measured using a Mini-Lum luminometer (Bioscan, Washington, CD).

Preparation of Nuclear Extracts

Nuclear extracts were prepared from RCS cells without or with 300 ng/ml BMP-2. Cells were harvested by trypsinization, washed in phosphate-buffered saline (PBS), pelleted, and resuspended in lysis buffer (10 mM Tris-HCl [pH 8.0], 60 mM KCl, 1 mM EDTA, 1 mM dithiothreitol, proteinase inhibitors, and 0.3% NP-1-40). After 5 mM on ice, the lysates were centrifuged at 1,000 g at 4° C. for 5 min, and the pelleted nuclei were washed in lysis buffer without NP-40. The nuclear pellet was resuspended in an equal volume of nuclear extraction buffer (20 mM Tris-HCl [pH 8.0], 420 mM NaCl, 1.5 mM $MgCl_2$, 0.2 mM EDTA, and 25% glycerol), and NaCl was added to obtain a final concentration of 400 mM. After incubation at 4° C. for 10 min, the nuclei were centrifuged at 25,000 g for 5 min. The supernatant fraction was used as nuclear extract.

Electrophoretic Mobility Shift Assay (EMSA)

The binding reaction was achieved by preincubating nuclear extracts with 1 μg poly (dI-dC)/poly (dI-dC) (Pharmacia Biotech, Piscataway, N.J.) in buffer containing 20 mmol/L HEPES, pH 7.9, 70 mmol/L NaCl, 5 mmol/L $MgCl_2$, 0.05% Nonidet P-40, 10% glycerol, 0.5 mmol/L dithiothreitol, and 5 mmol/L p-amidino phenylmethylsulfonyl fluoride (PMSF) at room temperature for 20 min. Three nanograms of end-labeled probes were added to the reaction mixture containing the nuclear extract and incubated for 15 min at room temperature. For competition experiments, excess unlabeled DNA was incubated with the reaction mixture for 15 min before the addition of the probe. In supershift assays, anti-SAMD4 IgG (0.5 μg) was included. After 15 min of incubation, the DIG-labeled probe was added, and the reaction mixture was incubated for a further 15 min and analyzed by gel electrophoresis.

Chromatin Immunoprecipitation (ChIP)

In vivo binding of SMAD4 to the GEP promoter was investigated using the ChIP assay kit (Upstate Biotechnology, Lake Placid, N.Y.). RCS cells treated with or without 300 ng/ml BMP-2 for 12 hours were cross-linked by formaldehyde treatment. Cells were washed with cold PBS and lysed with SDS lysis buffer (1% SDS, 10 mM EDTA, 50 mM Tris-HCl, pH 8.1). The lysate was sonicated to shear DNA to a length between 200 and 1000 bp. The sonicated supernatant was diluted 10-fold with ChIP dilution buffer (0.01% SDS, 1% Triton X-100, 2 mM Tris-HCl, pH 8.1, 150 mM NaCl) and incubated with either control or anti-SMAD4 antibody overnight at 4° C. with rotation. To collect DNA-SMAD4-antibody complex, salmon sperm DNA/protein A-agarose slurry was added to the mixture, incubated for 1 h at 4° C. with rotation, and the DNA/protein A agarose complex was pelleted by centrifugation. After extensive washing of the pellet in a series of washing buffers, the pellet was dissolved with 250 μl of elution buffer and centrifuged to remove agarose. The supernatant was treated with 20 μl of 5M NaCl and heated to 65° C. for 4 h to reverse the SMAD4-DNA cross-link. After treatment with EDTA and proteinase K, the supernatant was extracted with phenol/chloroform and precipitated with ethanol to recover the DNA. For PCR of the GEP promoter region using the chromatin-immunoprecipitated DNA, one-tenth of the DNA was PCR-amplified using primers spanning SMAD4-binding elements. Thirty-five cycles of PCR at 94° C. for 30 s, 55° C. for 30 s, and 72° C. for 30 s were performed. PCR products were analyzed by 1% agarose gel.

Results and Discussion

Figure 27:
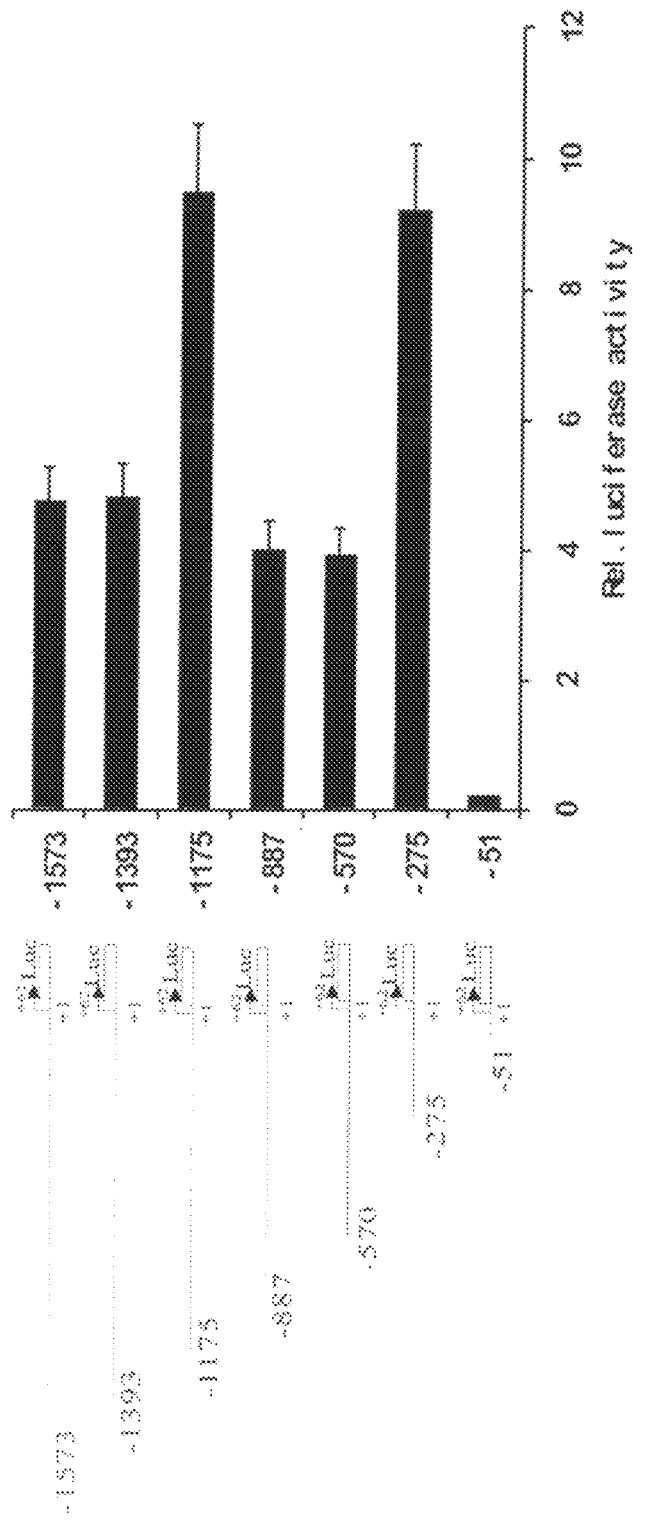
FIG. 27 provides 5' deletion analysis of the 5'-flanking region of GEP gene identifies a GEP minimal promoter (−275 to −51) and two putative negative regulatory regions (−1393 to −1175; −570 to −275). RCS cells were transfected with the above-shown deletion plasmids, which contain fragments of the GEP promoter from the respective 5' numbered nucleotide to +62, and luciferase and □-galactosidase assays were performed.

Deletion analysis of the 5'-flanking region of GEP gene identifies a GEP minimal promoter (−275 to −51): To delineate the GEP minimal promoter, we chose to use the chondrocytic cell line RCS which stably expresses several cartilage-specific genes including type II collagen and aggrecan and has been used by others to delineate elements in the promoters of col2a1 and col11a2. We first amplified various deletion mutants of 5'-flanking region of GEP gene and cloned them into pGL2 basic vector in order to generate various GEP-specific reporter constructs (FIG. 27). RCS cells were transfected with these deletion plasmids, which contain fragments of the GEP promoter from the respective 5' numbered nucleotide to +62, and luciferase and β-galactosidase assays were performed. A GEP minimal promoter (−275 to −51) and two putative negative regulatory regions (−1393 to −1175; −570 to −275) were isolated based on the activities in RCS cells.

Figure 28:
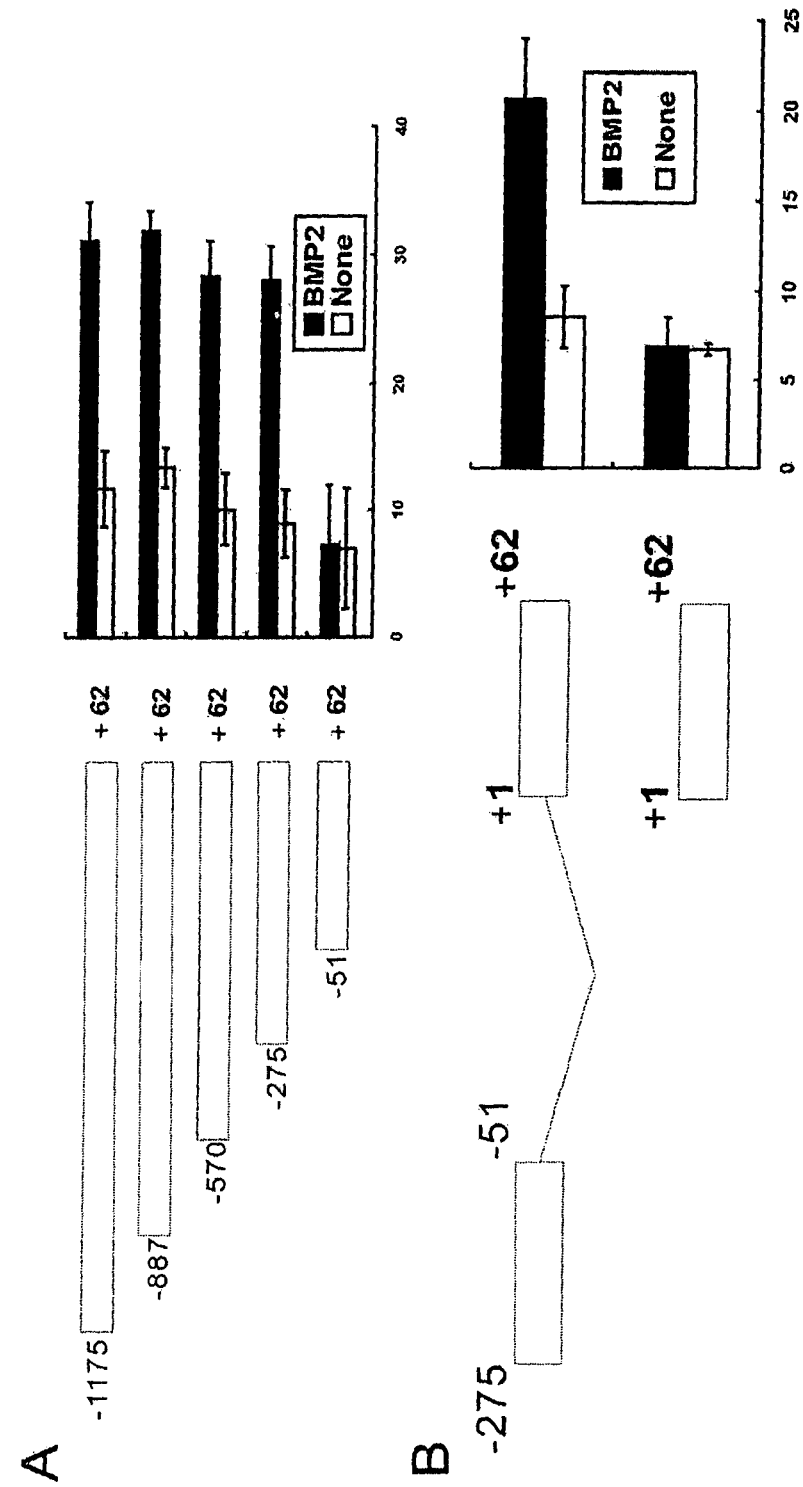
FIG. 28 shows that minimal promoter of GEP gene (−275 to −51) contains BMP-2 responsive elements. RCS cells were transfected with either 5'-deletion (A) or internal deletion (B)

Identification of BMP-Responsive Elements in the Human GEP Minimal Promoter:

Since we previously showed that BMP-2 induced the expression of GEP, we next determined the BMP-responsive elements in the 5'-flanking regulatory region of GEP gene using reporter gene assays. Briefly, RCS cells were transfected with above mentioned 5'-deletion reporter constructs, and luciferase and β-galactosidase assays were performed (FIG. 28A). All reporter constructs except −51GEPluc responded to BMP2 treatment, indicating that the BMP-responsive elements are located between −275 and −51, namely, in the minimal promoter of GEP gene. This finding was further verified with an internal deletion reporter construct, as revealed in FIG. 28B.

Sequence analyses revealed that the GEP minimal promoter (−275 to −51) contains several putative BMP-2 responsive motifs, including CAGC boxes, SMAD-binding site (SBE) and GC-rich sequence elements. To determine whether these motifs are involved in the response to BMP2, various mutants in these consensus elements were generated by site-directed mutagenesis in the GEP-specific reporter construct GEP-(−275/−51). The wild-type CGCC elements were replaced by AGAC mutated sequence, SBE (GTCT) sites were mutated GTAT, and the wild type GGCGCC palindrome sequence element (GC-pal) was replaced with GAAGCC, respectively. Wild-type and mutated GEP promoter luciferase constructs were transfected into RCS cells and subsequently treated with or without BMP-2 (100 ng/ml). As shown in FIG. 29, these mutants led to reduced response to BMP-2 treatment, indicating that all these elements are important for the BMP2 activation of GEP.

BMP2-Activated SMAD4 Binds to GEP Minimal Promoter:

Since BMP2 exerts its role through activating its downstream SMAD transcription factors, including Co-SMAD, SMAD4, we next examined whether SMAD4 was able to bind to the GEP minimal promoter, we first did EMSA assay. Incubation of GEP promoter probe with the nuclear extracts prepared from RCS cells in the absence or presence of BMP2 resulted in a specific SMAD4/DNA complex in the BMP-treated cells (FIG. 30A). The binding of probe to SMAD4 in vitro was completely competed by excess cold oligodeoxy-nucleotide. The SMAD4/DNA band was supershifted with antibodies to SMAD4.

To determine whether SMAD4 also binds to the GEP minimal promoter in vivo, we performed ChIP assays, which are important for defining interactions of factors with specific DNA elements in living cells. ChIP was carried out in RCS cells treated with or without 300 ng/ml BMP-2 for 12 hours. After cross-linking with formaldehyde, cell lysates were immunoprecipitated with control IgG (negative control), or anti-SMAD4 antibodies, and the DNA purified from this coprecipitation was analyzed by PCR with PCR primers that spanned the SMAD4 binding elements in the GEP promoter. As shown in FIG. 30B, we observed a clear PCR product using DNA isolated from immunoprecipitated complexes with anti-SMAD4 antibodies but not with control IgG (lane 1) from BMP2-treated RCS cells, indicating that the SMAD4 binds to the GEP promoter in response to BMP2 treatment.

BMP2 downstream transcription factor Smads Activate the GEP-Specific Reporter Genes:

Once we established that SMAD4 directly associated with the GEP promoter, we next determined whether SMAD transcription factors, including SMAD1, SMAD4 and SMAD5, could activate GEP-specific reporter genes, as did BMP2. Briefly, the GEP-specific reporter construct—1575GEPluc and a pSVgal internal control plasmid were transfected into RCS cells in the presence or absence of 300 ng/ml of BMP-2 (FIG. 31A) or the indicated Smad expression plasmids (i.e., Smad1, Smad4, and Smad5, FIG. 31B), and reporter genes activities were measured. Smad transcription factors, including SMAD1, SMAD4 and SMAD5, could activate the GEP-specific reporter gene; in addition, SMAD4 further enhanced SMAD1- or SMAD5-activated GEP activation.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A composition for modulating chondrogenesis comprising an isolated Granulin/epithelin precursor (GEP) polypeptide, and further comprising isolated cells selected from chondrocyte progenitors, mesenchymal stem cells, and stem cells capable of differentiating along the mesenchymal lineage, wherein said GEP polypeptide comprises an amino acid sequence selected from:

(a) SEQ ID NO: 2, or a chondrogenic fragment thereof;
(b) SEQ ID NO: 4, or a chondrogenic fragment thereof; and
(c) SEQ ID NO: 22, or a chondrogenic fragment thereof.

2. A composition for modulating chondrogenesis comprising an isolated Granulin/epithelin precursor (GEP) polypeptide, and further comprising cartilage oligomeric matrix protein (COMP), wherein said GEP polypeptide comprises an amino acid sequence selected from:

(a) SEQ ID NO: 2, or a chondrogenic fragment thereof;
(b) SEQ ID NO: 4, or a chondrogenic fragment thereof; and
(c) SEQ ID NO: 22, or a chondrogenic fragment thereof.

3. A composition for modulating chondrogenesis comprising an isolated Granulin/epithelin precursor (GEP) polypeptide, and further comprising one or more of a growth factor selected from bone morphogenetic protein-2 (BMP-2), transforming growth factor-beta (TGF (3), tumor necrosis factor-alpha (TNF α), fibroblast growth factor (FGF) and interleukin-1 beta (IL-1β), wherein said GEP polypeptide comprises an amino acid sequence selected from:

(a) SEQ ID NO: 2, or a chondrogenic fragment thereof;
(b) SEQ ID NO: 4, or a chondrogenic fragment thereof; and
(c) SEQ ID NO: 22, or a chondrogenic fragment thereof.

4. The composition of claim 1, 2, or 3, which is a pharmaceutical composition and further comprises a pharmaceutically acceptable carrier, vehicle, diluent or excipient.

* * * * *

UNITED STATES PATENT AND TRADEMARK OFFICE
CERTIFICATE OF CORRECTION

PATENT NO. : 8,536,128 B2
APPLICATION NO. : 12/932876
DATED : September 17, 2013
INVENTOR(S) : Chuan-Ju Liu and Sally Frenkel Page 1 of 1

It is certified that error appears in the above-identified patent and that said Letters Patent is hereby corrected as shown below:

In the Claims

Column 90, Line 31 of Claim 3:

In Column 90, Line 31 of Claim 3, delete "(TGF (3)" and insert --(TGF β)--.

Signed and Sealed this
Twentieth Day of May, 2014

Michelle K. Lee
*Deputy Director of the United States Patent and Trademark Office*

SEQUENCE LISTING

```
<160> NUMBER OF SEQ ID NOS: 24

<210> SEQ ID NO 1
<211> LENGTH: 2095
<212> TYPE: DNA
<213> ORGANISM: Homo sapiens

<400> SEQUENCE: 1
cgcaggcaga  ccatgtggac  cctggtgagc  tgggtggcct  taacagcagg  gctggtggct      60
ggaacgcggt  gcccagatgg  tcagttctgc  cctgtggcct  gctgcctgga  ccccggagga     120
gccagctaca  gctgctgccg  tccccttctg  gacaaatggc  ccacaacact  gagcaggcat     180
ctgggtggcc  cctgccaggt  tgatgccccac  tgctctgccg  gccactcctg  catctttacc     240
gtctcaggga  cttccagttg  ctgcccctte  ccagaggccg  tggcatgcgg  ggatggccat     300
cactgctgcc  cacggggctt  ccactgcagt  gcagacgggc  gatcctgctt  ccaaagatca     360
ggtaacaact  ccgtgggtgc  catccagtgc  cctgatagtc  agttcgaatg  cccggacttc     420
tccacgtgct  gtgttatggt  cgatggctcc  tgggggtgct  gccccatgcc  ccaggcttcc     480
tgctgtgaag  acagggtgca  ctgctgtccg  cacggtgcct  tctgcgacct  ggttcacacc     540
cgctgcatca  cacccacggg  cacccacccc  ctggcaaaga  agctccctgc  ccagaggact     600
```

```
aacagggcag tggccttgtc cagctcggtc atgtgtccgg acgcacggtc ccggtgccct    660
gatggttcta cctgctgtga gctgccagt  gggaagtatg gctgctgccc aatgcccaac    720
gccacctgct gctccgatca cctgcactgc tgccccaag  acactgtgtg tgacctgatc    780
cagagtaagt gcctctccaa ggagaacgct accacggacc tcctcactaa gctgcctgcg    840
cacacagtgg gcgatgtgaa atgtgacatg gaggtgagct gcccagatgg ctatacctgc    900
tgccgtctac agtcggggc  ctggggctgc tgcccttta  cccaggctgt gtgctgtgag    960
gaccacatac actgctgtcc cgcggggttt acgtgtgaca cgcagaaggg tacctgtgaa   1020
cagggggccc accaggtgcc ctggatggag aaggccccag ctcacctcag cctgccagac   1080
ccacaagcct tgaagagaga tgtcccctgt gataatgtca gcagctgtcc ctcctccgat   1140
acctgctgcc aactcacgtc tggggagtgg ggctgctgtc caatcccaga ggctgtctgc   1200
tgctcggacc accagcactg ctgcccccag cgatacacgt gtgtagctga ggggcagtgt   1260
cagcgaggaa gcgagatcgt ggctggactg gagaagatgc ctgcccgccg cggttcctta   1320
tcccacccca gagacatcgg ctgtgaccag cacaccagct gcccggtggg cggaacctgc   1380
tgcccgagcc agggtgggag ctgggcctgc tgccagttgc cccatgctgt gtgctgcgag   1440
gatcgccagc actgctgccc ggctggctac acctgcaacg tgaaggctcg atcctgcgag   1500
aaggaagtgg tctctgccca gcctgccacc ttcctggccc gtagccctca cgtgggtgtg   1560
aaggacgtgg agtgtgggga aggacacttc tgccatgata accagacctg ctgccgagac   1620
aaccgacagg gctgggcctg ctgtcccta  gcccagggcg tctgttgtgc tgatcggcgc   1680
cactgctgtc ctgctggctt ccgctgcgca cgcagggta  ccaagtgttt gcgcagggag   1740
gccccgcgct gggacgcccc tttgaggac  ccagccttga cagctgctgc tgagggaca    1800
gtactgaaga ctctgcagcc ctcgggaccc cactcggagg gtgccctctg ctcaggcctc   1860
cctagcacct ccccctaacc aaattctccc tggaccccat tctgagctcc ccatcaccat   1920
gggaggtggg gcctcaatct aaggcccttc cctgtcagaa gggggttgag gcaaaagccc   1980
attacaagct gccatcccct ccccgtttca gtggaccctg tggccaggtg cttttcccta   2040
tccacagggg tgtttgtgtg ttgggtgtgc tttcaataaa gtttgtcact ttctt         2095
```

<210> SEQ ID NO 2
<211> LENGTH: 593
<212> TYPE: PRT
<213> ORGANISM: Homo sapiens

<400> SEQUENCE: 2

```
Met Trp Thr Leu Val Ser Trp Val Ala Leu Thr Ala Gly Leu Val Ala
 1               5                  10                  15

Gly Thr Arg Cys Pro Asp Gly Gln Phe Cys Pro Val Ala Cys Cys Leu
             20                  25                  30

Asp Pro Gly Gly Ala Ser Tyr Ser Cys Cys Arg Pro Leu Leu Asp Lys
         35                  40                  45

Trp Pro Thr Thr Leu Ser Arg His Leu Gly Gly Pro Cys Gln Val Asp
     50                  55                  60

Ala His Cys Ser Ala Gly His Ser Cys Ile Phe Thr Val Ser Gly Thr
 65                  70                  75                  80

Ser Ser Cys Cys Pro Phe Pro Glu Ala Val Ala Cys Gly Asp Gly His
                 85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
```

-continued

```
            115                 120                 125
Ser Gln Phe Glu Cys Pro Asp Phe Ser Thr Cys Cys Val Met Val Asp
130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Val Met Cys
        195                 200                 205

Pro Asp Ala Arg Ser Arg Cys Pro Asp Gly Ser Thr Cys Cys Glu Leu
210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
        275                 280                 285

Ser Cys Pro Asp Gly Tyr Thr Cys Cys Arg Leu Gln Ser Gly Ala Trp
290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
        355                 360                 365

Val Ser Ser Cys Pro Ser Ser Asp Thr Cys Cys Gln Leu Thr Ser Gly
370                 375                 380

Glu Trp Gly Cys Cys Pro Ile Pro Glu Ala Val Cys Cys Ser Asp His
385                 390                 395                 400

Gln His Cys Cys Pro Gln Arg Tyr Thr Cys Val Ala Glu Gly Gln Cys
                405                 410                 415

Gln Arg Gly Ser Glu Ile Val Ala Gly Leu Glu Lys Met Pro Ala Arg
            420                 425                 430

Arg Gly Ser Leu Ser His Pro Arg Asp Ile Gly Cys Asp Gln His Thr
        435                 440                 445

Ser Cys Pro Val Gly Gly Thr Cys Cys Pro Ser Gln Gly Gly Ser Trp
450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
            500                 505                 510

His Val Gly Val Lys Asp Val Glu Cys Gly Glu Gly His Phe Cys His
        515                 520                 525

Asp Asn Gln Thr Cys Cys Arg Asp Asn Arg Gln Gly Trp Ala Cys Cys
530                 535                 540
```

```
Pro Tyr Ala Gln Gly Val Cys Cys Ala Asp Arg His Cys Cys Pro
545                 550                 555                 560

Ala Gly Phe Arg Cys Ala Arg Arg Gly Thr Lys Cys Leu Arg Glu
            565                 570                 575

Ala Pro Arg Trp Asp Ala Pro Leu Arg Asp Pro Ala Leu Arg Gln Leu
            580                 585                 590

Leu

<210> SEQ ID NO 3
<211> LENGTH: 2145
<212> TYPE: DNA
<213> ORGANISM: Mus musculus

<400> SEQUENCE: 3
gagatgcctc ccagggagcc cggaccccga cgcaggcaga ccatgtgggt cctgatgagc      60
tggctggcct tcgcggcagg gctggtagcc ggaacacagt gtccagatgg gcagttctgc    120
cctgttgcct gctgccttga ccagggagga gccaactaca gctgctgtaa ccctcttctg    180
gacacatggc ctagaataac gagccatcat ctagatggct cctgccagac ccatggccac    240
tgtcctgctg gctattcttg tcttctcact gtgtctggga cttccagctg ctgcccgttc    300
tctaagggtg tgtcttgtgg tgatggctac cactgctgcc ccagggcttc cactgtagt     360
gcagatggga atcctgcttc cagatgtca gataacccct gggtgctgt ccagtgtcct      420
gggagccagt ttgaatgtcc tgactctgcc acctgctgca ttatggttga tggttcgtgg    480
ggatgttgtc ccatgcccca ggcctcttgc tgtgaagaca gagtgcattg ctgtccccat    540
ggggcctcct gtgacctggt tcacacacga tgcgtttcac ccacgggcac ccacacccta    600
ctaaagaagt tccctgcaca aaagaccaac agggcagtgt cttttgcctt ttctgtcgtg    660
tgccctgatg ctaagaccca gtgtcccgat gattctacct gctgtgagct acccactggg    720
aagtatggct gctgtccaat gcccaatgcc atctgctgtt ccgaccacct gcactgctgc    780
ccccaggaca ctgtatgtga cctgatccag agtaagtgcc tatccaagaa ctacaccacg    840
gatctcctga ccaagctgcc tggataccca gtgaaggagg tgaagtgcga catggaggtg    900
agctgccctg aaggatatac ctgctgccgc ctcaacactg gggcctgggg ctgctgtcca    960
tttgccaagg ccgtgtgttg tgaggatcac attcattgct gcccggcagg gtttcagtgt   1020
cacacagaga aggaacctg cgaaatgggt atcctccaag taccctggat gaagaaggtc    1080
atagccccc ccgcctgcc agacccacag atcttgaaga gtgatacacc ttgtgatgac    1140
ttcactaggt gtcctacaaa caatacctgc tgcaaactca attctgggga ctggggctgc   1200
tgtcccatcc cagaggctgt ctgctgctca gacaaccagc attgctgccc tcagggcttc   1260
acatgtctgg ctcaggggta ctgtcagaag ggagacacaa tggtggctgg cctggagaag   1320
atacctgccc gccagacaac cccgctccaa attggagata tcggttgtga ccagcatacc   1380
agctgcccag tagggcaaac ctgctgccca agcctcaagg gaagttgggc ctgctgccag   1440
ctgccccatg ctgtgtgctg tgaggaccgg cagcactgtt gcccggccgg gtacacctgc   1500
aatgtgaagg cgaggacctg tgagaaggat gtcgatttta tccagcctcc cgtgctcctg   1560
accctcggcc ctaaggttgg aatgtggag tgtggagaag gcatttctg ccatgataac    1620
cagacctgtt gtaaagacag tgcaggagtc tgggcctgct gtccctacct aaagggtgtc   1680
tgctgtagag atggacgtca ctgttgcccc ggtggcttcc actgttcagc aggggaacc    1740
aagtgtttgc gaaagaagat tcctcgctgg gacatgtttt tgagggatcc ggtcccaaga   1800
ccgctactgt aaggaagggc tacagactta aggaactcca cagtcctggg aaccctgttc   1860
```

-continued

```
cgagggtacc cactactcag gcctccctag cgcctcctcc cctaacgtct ccccggccta    1920
ctcatcctga gtcaccctat caccatggga ggtggagcct caaactaaaa ccttcttta     1980 tggaaagaag gctgtggcca aaagccccgt atcaaactgc catttcttcc ggtttctgtg    2040
gaccttgtgg ccaggtgctc ttcccgagcc acaggtgttc tgtgagcttg cttgtgtgtg    2100
tgtgcgcgtg tgcgtgtgtt gctccaataa agtttgtaca ctttc                   2145
```

<210> SEQ ID NO 4
<211> LENGTH: 589
<212> TYPE: PRT
<213> ORGANISM: Mus musculus

<400> SEQUENCE: 4

```
Met Trp Val Leu Met Ser Trp Leu Ala Phe Ala Ala Gly Leu Val Ala
 1               5                  10                  15

Gly Thr Gln Cys Pro Asp Gly Gln Phe Cys Pro Val Ala Cys Cys Leu
            20                  25                  30

Asp Gln Gly Gly Ala Asn Tyr Ser Cys Cys Asn Pro Leu Leu Asp Thr
        35                  40                  45

Trp Pro Arg Ile Thr Ser His His Leu Asp Gly Ser Cys Gln Thr His
    50                  55                  60

Gly His Cys Pro Ala Gly Tyr Ser Cys Leu Leu Thr Val Ser Gly Thr
65                  70                  75                  80

Ser Ser Cys Cys Pro Phe Ser Lys Gly Val Ser Cys Gly Asp Gly Tyr
                85                  90                  95

His Cys Cys Pro Gln Gly Phe His Cys Ser Ala Asp Gly Lys Ser Cys
            100                 105                 110

Phe Gln Met Ser Asp Asn Pro Leu Gly Ala Val Gln Cys Pro Gly Ser
        115                 120                 125

Gln Phe Glu Cys Pro Asp Ser Ala Thr Cys Cys Ile Met Val Asp Gly
    130                 135                 140

Ser Trp Gly Cys Cys Pro Met Pro Gln Ala Ser Cys Cys Glu Asp Arg
145                 150                 155                 160

Val His Cys Cys Pro His Gly Ala Ser Cys Asp Leu Val His Thr Arg
                165                 170                 175

Cys Val Ser Pro Thr Gly Thr His Thr Leu Leu Lys Lys Phe Pro Ala
            180                 185                 190

Gln Lys Thr Asn Arg Ala Val Ser Leu Pro Phe Ser Val Val Cys Pro
        195                 200                 205

Asp Ala Lys Thr Gln Cys Pro Asp Ser Thr Cys Cys Glu Leu Pro
    210                 215                 220

Thr Gly Lys Tyr Gly Cys Cys Pro Met Pro Asn Ala Ile Cys Cys Ser
225                 230                 235                 240

Asp His Leu His Cys Cys Pro Gln Asp Thr Val Cys Asp Leu Ile Gln
                245                 250                 255

Ser Lys Cys Leu Ser Lys Asn Tyr Thr Thr Asp Leu Leu Thr Lys Leu
            260                 265                 270

Pro Gly Tyr Pro Val Lys Glu Val Lys Cys Asp Met Glu Val Ser Cys
        275                 280                 285

Pro Glu Gly Tyr Thr Cys Cys Arg Leu Asn Thr Gly Ala Trp Gly Cys
    290                 295                 300

Cys Pro Phe Ala Lys Ala Val Cys Cys Glu Asp His Ile His Cys Cys
305                 310                 315                 320

Pro Ala Gly Phe Gln Cys His Thr Glu Lys Gly Thr Cys Glu Met Gly
```

```
                          325                 330                 335
Ile Leu Gln Val Pro Trp Met Lys Lys Val Ile Ala Pro Leu Arg Leu
            340                 345                 350

Pro Asp Pro Gln Ile Leu Lys Ser Asp Thr Pro Cys Asp Asp Phe Thr
            355                 360                 365

Arg Cys Pro Thr Asn Asn Thr Cys Cys Lys Leu Asn Ser Gly Asp Trp
370                 375                 380

Gly Cys Cys Pro Ile Pro Glu Ala Val Cys Cys Ser Asp Asn Gln His
385                 390                 395                 400

Cys Cys Pro Gln Gly Phe Thr Cys Leu Ala Gln Gly Tyr Cys Gln Lys
                405                 410                 415

Gly Asp Thr Met Val Ala Gly Leu Glu Lys Ile Pro Ala Arg Gln Thr
            420                 425                 430

Thr Pro Leu Gln Ile Gly Asp Ile Gly Cys Asp Gln His Thr Ser Cys
            435                 440                 445

Pro Val Gly Gln Thr Cys Cys Pro Ser Leu Lys Gly Ser Trp Ala Cys
            450                 455                 460

Cys Gln Leu Pro His Ala Val Cys Cys Glu Asp Arg Gln His Cys Cys
465                 470                 475                 480

Pro Ala Gly Tyr Thr Cys Asn Val Lys Ala Arg Thr Cys Glu Lys Asp
                485                 490                 495

Val Asp Phe Ile Gln Pro Pro Val Leu Leu Thr Leu Gly Pro Lys Val
            500                 505                 510

Gly Asn Val Glu Cys Gly Glu Gly His Phe Cys His Asp Asn Gln Thr
            515                 520                 525

Cys Cys Lys Asp Ser Ala Gly Val Trp Ala Cys Cys Pro Tyr Leu Lys
            530                 535                 540

Gly Val Cys Cys Arg Asp Gly Arg His Cys Cys Pro Gly Gly Phe His
545                 550                 555                 560

Cys Ser Ala Arg Gly Thr Lys Cys Leu Arg Lys Lys Ile Pro Arg Trp
                565                 570                 575

Asp Met Phe Leu Arg Asp Pro Val Pro Arg Pro Leu Leu
            580                 585

<210> SEQ ID NO 5
<211> LENGTH: 53
<212> TYPE: PRT
<213> ORGANISM: Artificial Sequence
<220> FEATURE:
<221> NAME/KEY: variation
<222> LOCATION: 2,3,4,5,6,9,10,11,12,13,16,17,18,19,20,21,22,23,26,27,
      28,29,30,31,34,36,37,42,43,44,45,47,48,49,50,51
<223> OTHER INFORMATION: Xaa can be any amino acid
<221> NAME/KEY: variation
<222> LOCATION: 7,52
<223> OTHER INFORMATION: Xaa can be no amino acid or any amino acid
<223> OTHER INFORMATION: consensus sequence

<400> SEQUENCE: 5

Cys Xaa Xaa Xaa Xaa Xaa Cys Xaa Xaa Xaa Xaa Xaa Cys Cys Xaa
1               5                   10                  15

Xaa Xaa Xaa Xaa Xaa Xaa Xaa Cys Cys Xaa Xaa Xaa Xaa Xaa Cys
                20                  25                  30

Cys Xaa Asp Xaa Xaa His Cys Cys Pro Xaa Xaa Xaa Xaa Cys Xaa Xaa
            35                  40                  45

Xaa Xaa Xaa Xaa Cys
    50
```

-continued

```
<210> SEQ ID NO 6
<211> LENGTH: 51
<212> TYPE: PRT
<213> ORGANISM: Artificial Sequence
<220> FEATURE:
<221> NAME/KEY: VARIANT
<222> LOCATION: 1,2,5,6,7,8,9,13,14,15,16,17,18,19,20,23,24,25,26,27,28,
      31,32,33,34,35,38,39,40,41,43,44,45,46,47,48,50,51
<223> OTHER INFORMATION: Xaa can be any amino acid
<221> NAME/KEY: VARIANT
<222> LOCATION: 3,10,48
<223> OTHER INFORMATION: Xaa can be no amino acid or any amino acid
<223> OTHER INFORMATION: consensus sequence

<400> SEQUENCE: 6

Xaa Xaa Xaa Cys Xaa Xaa Xaa Xaa Xaa Xaa Cys Cys Xaa Xaa Xaa Xaa
 1               5                  10                  15

Xaa Xaa Xaa Xaa Cys Cys Xaa Xaa Xaa Xaa Xaa Xaa Cys Cys Xaa Xaa
             20                  25                  30

Xaa Xaa Xaa Cys Cys Xaa Xaa Xaa Xaa Cys Xaa Xaa Xaa Xaa Xaa Xaa
         35                  40                  45

Cys Xaa Xaa
     50

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gtgccttctg cgacctggtt                                              20

<210> SEQ ID NO 8
<211> LENGTH: 40
<212> TYPE: DNA
<213> ORGANISM: Artificial Sequence
<220> FEATURE:
<223> OTHER INFORMATION: primer

<400> SEQUENCE: 8
aggtccgtgg tagcgttctc aggtccgtgg tagcgttctc                        40

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tccgatacct gctgccaact                                              20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ctcgcttcct cgctgacact                                              20

<210> SEQ ID NO 11
<211> LENGTH: 25
<212> TYPE: DNA
```

<213> ORGANISM: Artificial Sequence
<220> FEATURE:
<223> OTHER INFORMATION: primer

<400> SEQUENCE: 11
cactgtcctg ctggctattc ttgtc                                              25

<210> SEQ ID NO 12
<211> LENGTH: 25
<212> TYPE: DNA
<213> ORGANISM: Artificial Sequence
<220> FEATURE:
<223> OTHER INFORMATION: primer

<400> SEQUENCE: 12
atgtcgcact tcacctcctt cactg                                              25

<210> SEQ ID NO 13
<211> LENGTH: 1950
<212> TYPE: DNA
<213> ORGANISM: Homo sapiens

<400> SEQUENCE: 13
ggcacagact agtactaggt cctcagcagg ccaggtgtct tatccgctgt ctgggtctgc        60
tctagctcca ggcttagaac ccctgccaca cgactccaca gctcggttgg cacccttccc       120
ctcctccgac ttctgctgcc tcgagcttgg ttagccatcc cctgcccct gcctcatcct        180 cagctccagt tccttgctca ggctgcagca gtctccatcc cctgtgcaga cactgccgtt       240
cctccacggc ccagtatcag gctttccctg ggcctctcct ctctcctggc ccatctccca       300
tcatccatct ctgcctggcc caggcccttt ggcaccaagc aggctgactc ttgtcactgg       360
ctaatctgtt ctgtggtaca ttttctctcc tcaccctccc atatcaattc ctcgaaggca       420
gggccgatct ggagactagg aagccacttc tctttcgaca gccccacca cagcccagcc        480 cgtgccaggc acccagcagc tcctgaagcc cactggcatt gaacatggca ttcaatccct       540
gccaagcctg cccttcccat ctggtttccc agggctcttc ccaacacctc ctcctccacc       600
tgccagttaa atcttccca gactcagctc aaggagatgc tcctaaggtg gaatgaaatc        660
tcttcttccc cacctggaga caatctactt cctctcccta cacctggcaa ctggcgcaca       720
accttgtatc ttaaattaga ttcagcctga gactgtctcc caccaatccc tgctccctgt      780
cctgctgagc accttgagga aagggctttg gggctgttta tctttgtcct ggaaaccatc      840
cttcaactca ctctggggcc tgcctagcat gtcaaccgag tttggagaat agggcagaat      900
agggcaggac aggacaggac aagacagggc aggataggat aggagcgagc cagctcagta      960
gctcacattt gtaatcccag cgccttgggg ggctgcggta ggagaatcgc tttgggagca     1020
ggagttgcag gccgcagtga gctatgatca gcttgggcga ctgagcgaga ccctgtctct     1080
aaaacaaaca cacaagtccg ggcgcggtgg ctcatgcctg taatcttagc actttgggag     1140
gccgaggtgg gcggatcacg aggtcaagaa atcgagacca tcctggccaa catggtgaaa     1200
ccccgtctct actaaaaata caaaaattag ctgggcgtgg tggtgcgcgc ctgtagtccc     1260
agctactcgg gaggctgagg caggagaatc gcttgaaccc gggaggcaga ggttgcagtg     1320
agccgagatc gtgccactgc actccagcct ggcgacagag tgagactccg tctcagaaca     1380
aacaaacaaa aggatagaaa ggcgagcaca atattccca attcataaca ctccctcgca      1440
ctgtcaatgc cccagacacg cgctatcatc tctagcaaac tccccaggc gcctgcagga      1500 tgggttaagg aaggcgacga gcaccagctg ccctgctgag gctgtcccga cgtcacatga     1560

```
ttctccaatc acatgatccc tagaaatggg gtgtggggcg agaggaagca gggaggagag    1620
tgatttgagt agaaaagaaa cacagcattc caggctggcc ccacctctat attgataagt    1680
agccaatggg agcgggtagc cctgatccct ggccaatgga aactgaggta ggcgggtcat    1740
cgcgctgggg tctgtagtct gagcgctacc cggttgctgc tgcccaagga ccgcggagtc    1800
ggacgcaggt aggagagcgg ccgcgcagac ctctcgcctg ctcctgccca ggggcccgcc    1860
agggccatgt gagcttgagg ttcccctgga gtctcagccg agacaacag aagaaccgct     1920 tactgaaact ccttgggggt tctgatacac                                    1950
```

<210> SEQ ID NO 14
<211> LENGTH: 19
<212> TYPE: DNA
<213> ORGANISM: Artificial Sequence
<220> FEATURE:
<223> OTHER INFORMATION: siRNA target sequence

<400> SEQUENCE: 14

```
gccuauccaa gaacuacac                                                  19
```

<210> SEQ ID NO 15
<211> LENGTH: 56
<212> TYPE: PRT
<213> ORGANISM: Rattus norvegicus

<400> SEQUENCE: 15

```
Glu Val Lys Cys Asp Leu Glu Val Ser Cys Pro Asp Gly Tyr Thr Cys
 1               5                  10                  15

Cys Arg Leu Asn Thr Gly Ala Trp Gly Cys Cys Pro Phe Thr Lys Ala
                20                  25                  30

Val Cys Cys Glu Asp His Ile His Cys Cys Pro Ala Gly Phe Gln Cys
            35                  40                  45

His Thr Glu Thr Gly Thr Cys Glu
        50                  55
```

<210> SEQ ID NO 16
<211> LENGTH: 53
<212> TYPE: PRT
<213> ORGANISM: Rattus norvegicus

<400> SEQUENCE: 16

```
Val Pro Cys Asp Asp Phe Ser Ser Cys Pro Ser Asn Asn Thr Cys Cys
 1               5                  10                  15

Arg Leu Ser Ser Gly Asp Trp Gly Cys Cys Pro Met Pro Glu Ala Val
                20                  25                  30

Cys Cys Leu Asp His Gln His Cys Cys Pro Gln Gly Phe Lys Cys Met
            35                  40                  45

Asp Glu Gly Tyr Cys
        50
```

<210> SEQ ID NO 17
<211> LENGTH: 55
<212> TYPE: PRT
<213> ORGANISM: Rattus norvegicus

<400> SEQUENCE: 17

```
Asp Ile Gly Cys Asp Gln His Thr Ser Cys Pro Val Gly Gln Thr Cys
 1               5                  10                  15

Cys Pro Ser Leu Lys Gly Ser Trp Ala Cys Cys Gln Leu Pro His Ala
                20                  25                  30
```

```
Val Cys Cys Glu Asp Arg Gln His Cys Cys Pro Ala Gly Tyr Thr Cys
         35                  40                  45

Asn Val Lys Ala Arg Thr Cys
         50                  55

<210> SEQ ID NO 18
<211> LENGTH: 56
<212> TYPE: PRT
<213> ORGANISM: Rattus norvegicus

<400> SEQUENCE: 18

Gly Asn Val Glu Cys Gly Ala Gly His Phe Cys His Asp Asn Gln Ser
  1               5                  10                  15

Cys Cys Lys Asp Ser Gln Gly Gly Trp Ala Cys Cys Pro Tyr Val Lys
             20                  25                  30

Gly Val Cys Cys Arg Asp Gly His Cys Cys Pro Ile Gly Phe His
         35                  40                  45

Cys Ser Ala Lys Gly Thr Lys Cys
         50                  55

<210> SEQ ID NO 19
<211> LENGTH: 311
<212> TYPE: PRT
<213> ORGANISM: Rattus norvegicus

<400> SEQUENCE: 19

Glu Val Lys Cys Asp Leu Glu Val Ser Cys Pro Asp Gly Tyr Thr Cys
  1               5                  10                  15

Cys Arg Leu Asn Thr Gly Ala Trp Gly Cys Cys Pro Phe Thr Lys Ala
             20                  25                  30

Val Cys Cys Glu Asp His Ile His Cys Cys Pro Ala Gly Phe Gln Cys
         35                  40                  45

His Thr Glu Thr Gly Thr Cys Glu Leu Gly Val Leu Gln Val Pro Trp
         50                  55                  60

Met Lys Lys Val Thr Ala Ser Leu Ser Leu Pro Asp Pro Gln Ile Leu
 65                  70                  75                  80

Lys Asn Asp Val Pro Cys Asp Asp Phe Ser Ser Cys Pro Ser Asn Asn
                 85                  90                  95

Thr Cys Cys Arg Leu Ser Ser Gly Asp Trp Gly Cys Cys Pro Met Pro
            100                 105                 110

Glu Ala Val Cys Cys Leu Asp His Gln His Cys Cys Pro Gln Gly Phe
            115                 120                 125

Lys Cys Met Asp Glu Gly Tyr Cys Gln Lys Gly Asp Arg Met Val Ala
        130                 135                 140

Gly Leu Glu Lys Met Pro Val Arg Gln Thr Thr Leu Leu Gln His Gly
145                 150                 155                 160

Asp Ile Gly Cys Asp Gln His Thr Ser Cys Pro Val Gly Gln Thr Cys
                165                 170                 175

Cys Pro Ser Leu Lys Gly Ser Trp Ala Cys Cys Gln Leu Pro His Ala
            180                 185                 190

Val Cys Cys Glu Asp Arg Gln His Cys Cys Pro Ala Gly Tyr Thr Cys
        195                 200                 205

Asn Val Lys Ala Arg Thr Cys Glu Lys Asp Ala Gly Ser Val Gln Pro
        210                 215                 220

Ser Met Asp Leu Thr Phe Gly Ser Lys Val Gly Asn Val Glu Cys Gly
225                 230                 235                 240

Ala Gly His Phe Cys His Asp Asn Gln Ser Cys Cys Lys Asp Ser Gln
```

```
                       245                 250                 255
Gly Gly Trp Ala Cys Cys Pro Tyr Val Lys Gly Val Cys Cys Arg Asp
            260                 265                 270

Gly Arg His Cys Cys Pro Ile Gly Phe His Cys Ser Ala Lys Gly Thr
            275                 280                 285

Lys Cys Leu Arg Lys Lys Thr Pro Arg Trp Asp Ile Leu Leu Arg Asp
            290                 295                 300

Pro Ala Pro Arg Pro Leu Leu
305                 310

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
ccactgtcct gctggctatt                                                  20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
cactgccctg ttggtctttt                                                  20

<210> SEQ ID NO 22
<211> LENGTH: 588
<212> TYPE: PRT
<213> ORGANISM: Rattus norvegicus

<400> SEQUENCE: 22

Met Trp Ile Leu Val Ser Trp Leu Ala Leu Ala Arg Leu Val Ala
 1               5                  10                  15

Gly Thr Gln Cys Pro Asp Gly Gln Phe Cys Pro Val Ala Cys Cys Leu
                20                  25                  30

Asp Gln Gly Gly Ala Asn Tyr Ser Cys Cys Asn Pro Leu Leu Asp Thr
            35                  40                  45

Trp Pro Ile Ile Thr Ser Arg Arg Leu Asp Gly Ser Cys Gln Ile Arg
        50                  55                  60

Asp His Cys Pro Asp Gly Tyr Ser Cys Leu Leu Thr Val Ser Gly Thr
65                  70                  75                  80

Ser Ser Cys Cys Pro Phe Ser Glu Gly Val Ser Cys Asp Asp Gly Gln
                85                  90                  95

His Cys Cys Pro Arg Gly Phe His Cys Ser Ala Asp Gly Lys Ser Cys
            100                 105                 110

Ser Gln Ile Ser Asp Ser Leu Leu Gly Ala Val Gln Cys Pro Gly Ser
        115                 120                 125

Gln Phe Glu Cys Pro Asp Ser Ala Thr Cys Cys Ile Met Ile Asp Gly
    130                 135                 140

Ser Trp Gly Cys Cys Pro Met Pro Gln Ala Ser Cys Cys Glu Asp Arg
145                 150                 155                 160

Val His Cys Cys Pro His Gly Ala Ser Cys Asp Leu Val His Thr Arg
                165                 170                 175

Cys Ile Ser Pro Thr Gly Thr His Pro Leu Leu Lys Lys Phe Pro Ala
```

```
                        180             185             190
Gln Arg Thr Asn Arg Ala Val Ala Ser Phe Ser Val Cys Pro Asp
                195                 200                 205
Ala Lys Thr Gln Cys Pro Asp Asp Ser Thr Cys Cys Glu Leu Pro Thr
210                 215                 220
Gly Lys Tyr Gly Cys Cys Pro Met Pro Asn Ala Ile Cys Cys Ser Asp
225                 230                 235                 240
His Leu His Cys Cys Pro Gln Asp Thr Val Cys Asp Leu Ile Gln Ser
                245                 250                 255
Lys Cys Ile Ser Lys Asp Tyr Thr Thr Asp Leu Met Thr Lys Leu Pro
            260                 265                 270
Gly Tyr Pro Val Asn Glu Val Lys Cys Asp Leu Glu Val Ser Cys Pro
            275                 280                 285
Asp Gly Tyr Thr Cys Cys Arg Leu Asn Thr Gly Ala Trp Gly Cys Cys
            290                 295                 300
Pro Phe Thr Lys Ala Val Cys Cys Glu Asp His Ile His Cys Cys Pro
305                 310                 315                 320
Ala Gly Phe Gln Cys His Thr Glu Thr Gly Thr Cys Glu Leu Gly Val
                325                 330                 335
Leu Gln Val Pro Trp Met Lys Lys Val Thr Ala Ser Leu Ser Leu Pro
            340                 345                 350
Asp Pro Gln Ile Leu Lys Asn Asp Val Pro Cys Asp Asp Phe Ser Ser
            355                 360                 365
Cys Pro Ser Asn Asn Thr Cys Cys Arg Leu Ser Ser Gly Asp Trp Gly
    370                 375                 380
Cys Cys Pro Met Pro Glu Ala Val Cys Cys Leu Asp His Gln His Cys
385                 390                 395                 400
Cys Pro Gln Gly Phe Lys Cys Met Asp Glu Gly Tyr Cys Gln Lys Gly
                405                 410                 415
Asp Arg Met Val Ala Gly Leu Glu Lys Met Pro Val Arg Gln Thr Thr
            420                 425                 430
Leu Leu Gln His Gly Asp Ile Gly Cys Asp Gln His Thr Ser Cys Pro
            435                 440                 445
Val Gly Gln Thr Cys Cys Pro Ser Leu Lys Gly Ser Trp Ala Cys Cys
450                 455                 460
Gln Leu Pro His Ala Val Cys Cys Glu Asp Arg Gln His Cys Cys Pro
465                 470                 475                 480
Ala Gly Tyr Thr Cys Asn Val Lys Ala Arg Thr Cys Glu Lys Asp Ala
                485                 490                 495
Gly Ser Val Gln Pro Ser Met Asp Leu Thr Phe Gly Ser Lys Val Gly
            500                 505                 510
Asn Val Glu Cys Gly Ala Gly His Phe Cys His Asp Asn Gln Ser Cys
            515                 520                 525
Cys Lys Asp Ser Gln Gly Gly Trp Ala Cys Cys Pro Tyr Val Lys Gly
            530                 535                 540
Val Cys Cys Arg Asp Gly Arg His Cys Cys Pro Ile Gly Phe His Cys
545                 550                 555                 560
Ser Ala Lys Gly Thr Lys Cys Leu Arg Lys Lys Thr Pro Arg Trp Asp
                565                 570                 575
Ile Leu Leu Arg Asp Pro Ala Pro Arg Pro Leu Leu
            580                 585

<210> SEQ ID NO 23
<211> LENGTH: 60
```

```
<212> TYPE: DNA
<213> ORGANISM: Artificial Sequence
<220> FEATURE:
<223> OTHER INFORMATION: siRNA sequence

<400> SEQUENCE: 23
gatccccgcc tatccaagaa ctacacttca agagagtgta gttcttggat aggcttttta      60

<210> SEQ ID NO 24
<211> LENGTH: 227
<212> TYPE: DNA
<213> ORGANISM: Homo sapiens

<400> SEQUENCE: 24
agccgagatc gtgccactgc actccagcct ggcgacagag tgagactccg tctcagaaca      60
aacaaacaaa aggatagaaa ggcgagcaca aatattccca attcataaca ctccctcgca     120
ctgtcaatgc cccagacacg cgctatcatc tctagcaaac tcccccaggc gcctgcagga     180
tgggttaagg aaggcgacga gcaccagctg ccctgctgag gctgtcc                   227
```